(12) United States Patent
Woodard et al.

(10) Patent No.: US 9,883,853 B2
(45) Date of Patent: Feb. 6, 2018

(54) INTRAOSSEOUS DEVICE COUPLERS, DRIVERS, KITS, AND METHODS

(71) Applicant: Vidacare LLC, Shavano Park, TX (US)

(72) Inventors: Steven Paul Woodard, Cupertino, CA (US); Michel Yoon, Fremont, CA (US)

(73) Assignee: TELEFLEX MEDICAL DEVICES S.À.R.L., Luxembourg (LU)

( * ) Notice: Subject to any disclaimer, the term of this patent is extended or adjusted under 35 U.S.C. 154(b) by 780 days.

(21) Appl. No.: 13/835,383

(22) Filed: Mar. 15, 2013

(65) Prior Publication Data

US 2014/0276206 A1 Sep. 18, 2014

(51) Int. Cl.
*A61B 10/02* (2006.01)
*B23B 31/113* (2006.01)

(52) U.S. Cl.
CPC .......... *A61B 10/025* (2013.01); *B23B 31/113* (2013.01); *B23B 2231/04* (2013.01); *Y10T 279/17888* (2015.01); *Y10T 279/3412* (2015.01)

(58) Field of Classification Search
CPC .............. B23B 31/113; B23B 2231/04; Y10T 279/3406; Y10T 279/3412; Y10T 279/3418; Y10T 279/17863; Y10T 279/17897; Y10T 279/17888; A61B 10/025
See application file for complete search history.

(56) References Cited

U.S. PATENT DOCUMENTS

| | | | | |
|---|---|---|---|---|
| 684,951 A | * | 10/1901 | Rothkranz | A61C 1/16 279/93 |
| 1,418,184 A | * | 5/1922 | Trunick | B25G 1/00 279/93 |
| 1,479,583 A | * | 1/1924 | Carey | F16C 1/08 211/183 |
| 1,494,859 A | * | 5/1924 | Miller | B23B 31/113 279/93 |
| 2,337,402 A | * | 12/1943 | Mills | B23B 31/113 279/83 |
| 6,638,235 B2 | * | 10/2003 | Miller | A61B 10/025 600/564 |
| 7,997,837 B2 | * | 8/2011 | Furusawa | B23Q 3/12 279/144 |
| 8,220,367 B2 | * | 7/2012 | Hsu | B23B 51/126 279/144 |
| 8,641,715 B2 | | 2/2014 | Miller et al. | |
| 9,131,924 B2 | * | 9/2015 | Faccioli | A61B 10/025 |
| 9,510,910 B2 | | 12/2016 | Miller et al. | |
| 9,717,564 B2 | | 8/2017 | Miller et al. | |
| 2008/0045860 A1 | | 2/2008 | Miller et al. | 600/567 |

(Continued)

FOREIGN PATENT DOCUMENTS

| DE | 29621130 U1 | * | 2/1997 | .......... B23B 31/113 |
|---|---|---|---|---|
| JP | 2792836 B2 | * | 9/1998 | .......... B23B 31/113 |

(Continued)

OTHER PUBLICATIONS

International Search Report and Written Opinion issued in PCT/US2014/028915, dated Sep. 25, 2014.

*Primary Examiner* — Eric A Gates

(74) *Attorney, Agent, or Firm* — Baker & Hostetler LLP

(57) ABSTRACT

This disclosure includes various embodiments of couplers for coupling intraosseous (IO) devices and drivers, and various embodiments of drivers and kits.

12 Claims, 41 Drawing Sheets

(56) References Cited

U.S. PATENT DOCUMENTS

| | | | |
|---|---|---|---|
| 2009/0112168 A1 | 4/2009 | Miller et al. .................. | 604/181 |
| 2009/0248029 A1 | 10/2009 | Paulos ......................... | 606/104 |
| 2010/0298784 A1 | 11/2010 | Miller et al. .................. | 604/272 |
| 2011/0184425 A1 | 7/2011 | Cheraux ....................... | 606/104 |
| 2013/0319706 A1* | 12/2013 | Nicholas .................. | B25F 3/00 |
| | | | 173/29 |

FOREIGN PATENT DOCUMENTS

| | | | | |
|---|---|---|---|---|
| WO | WO 9221469 A1 * | 12/1992 | .......... | B23B 31/113 |
| WO | 2008/033874 A2 | 3/2008 | | |

\* cited by examiner

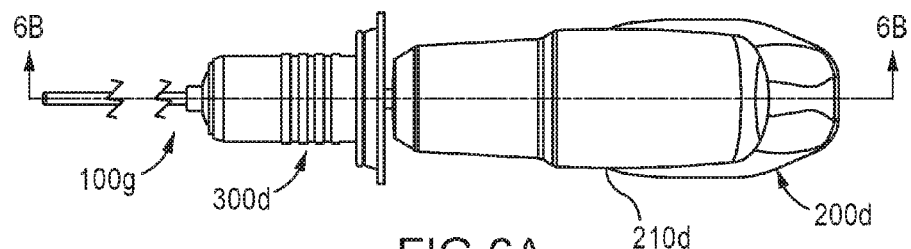
FIG.6A
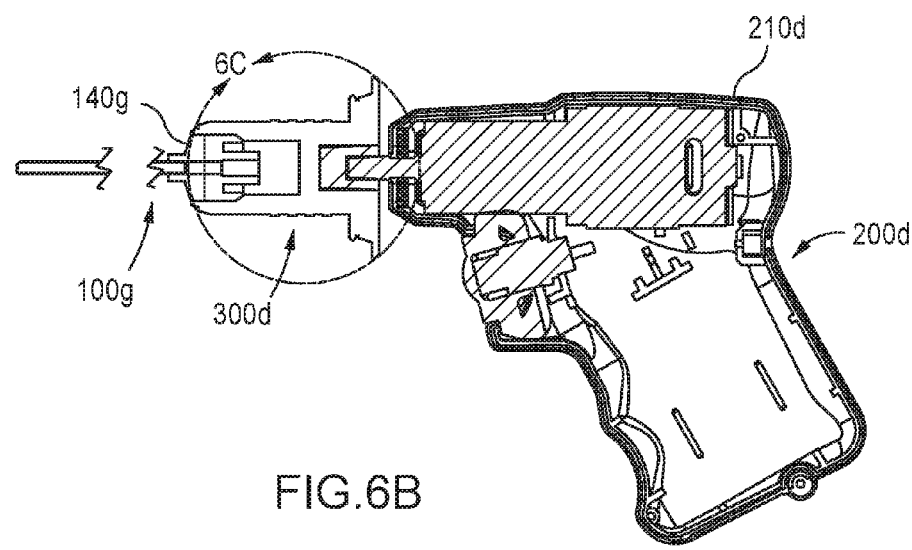
FIG.6B
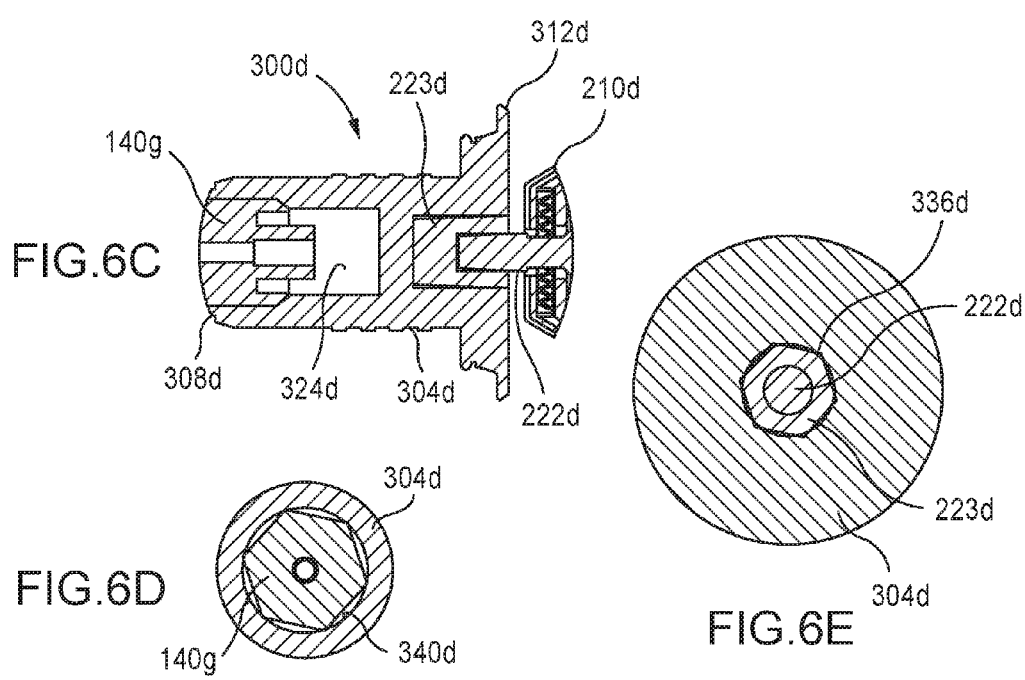
FIG.6C
FIG.6D
FIG.6E

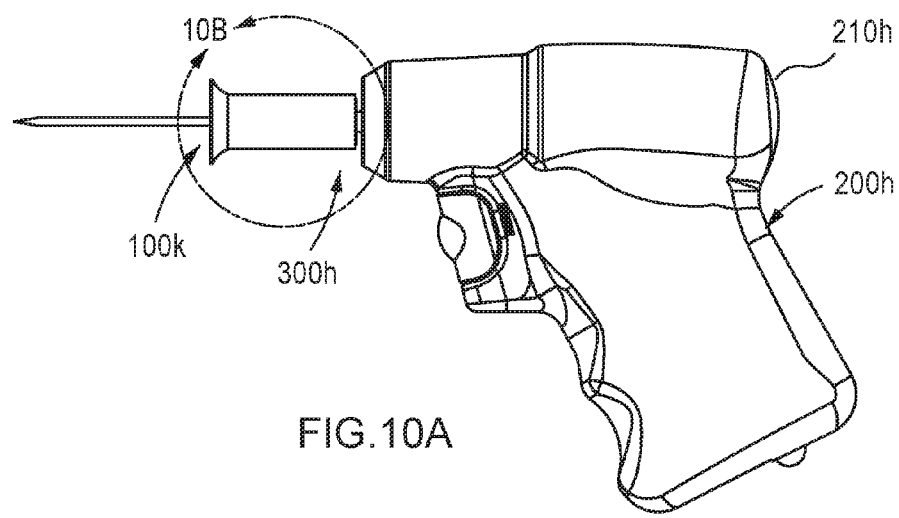
FIG.10A
FIG.10B
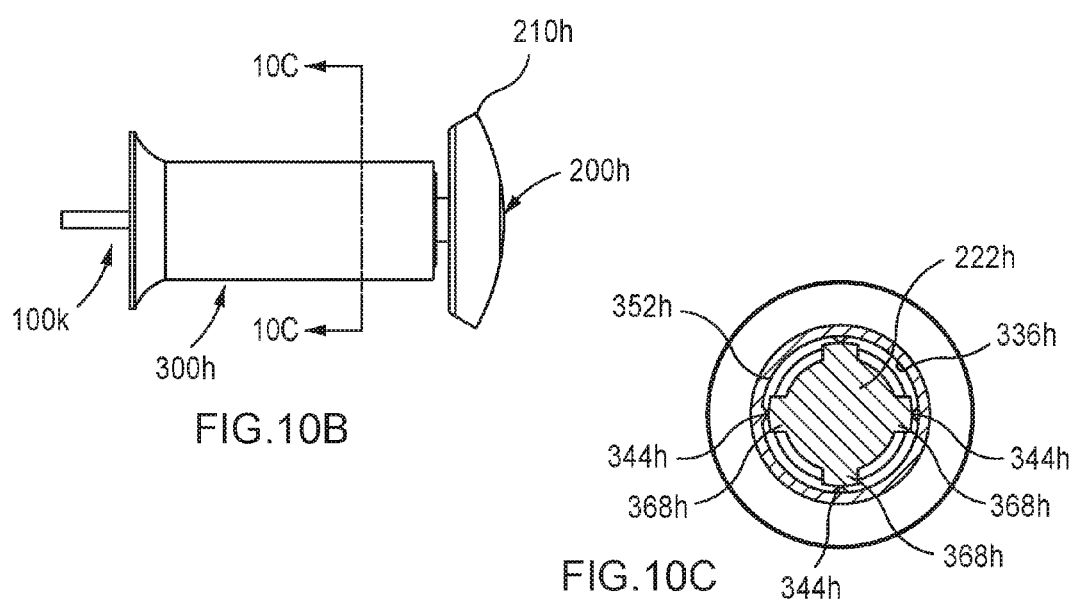
FIG.10C
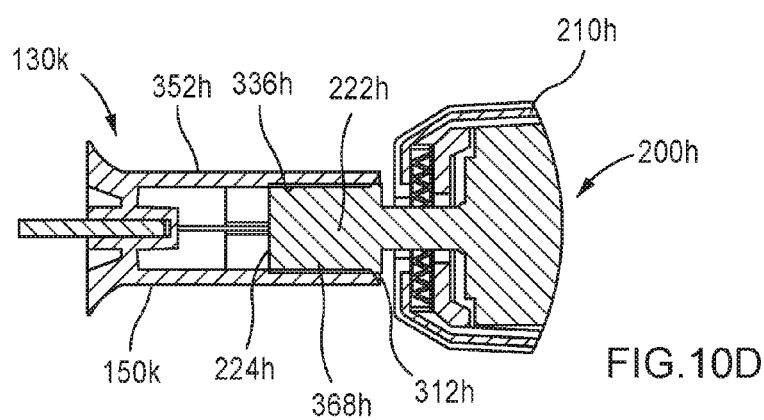
FIG.10D

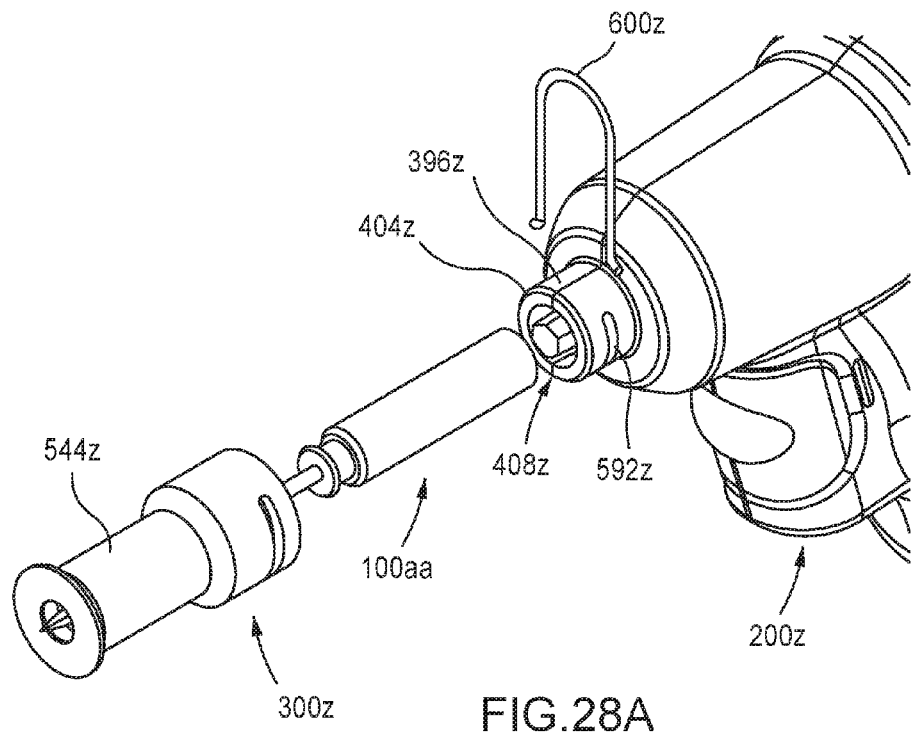
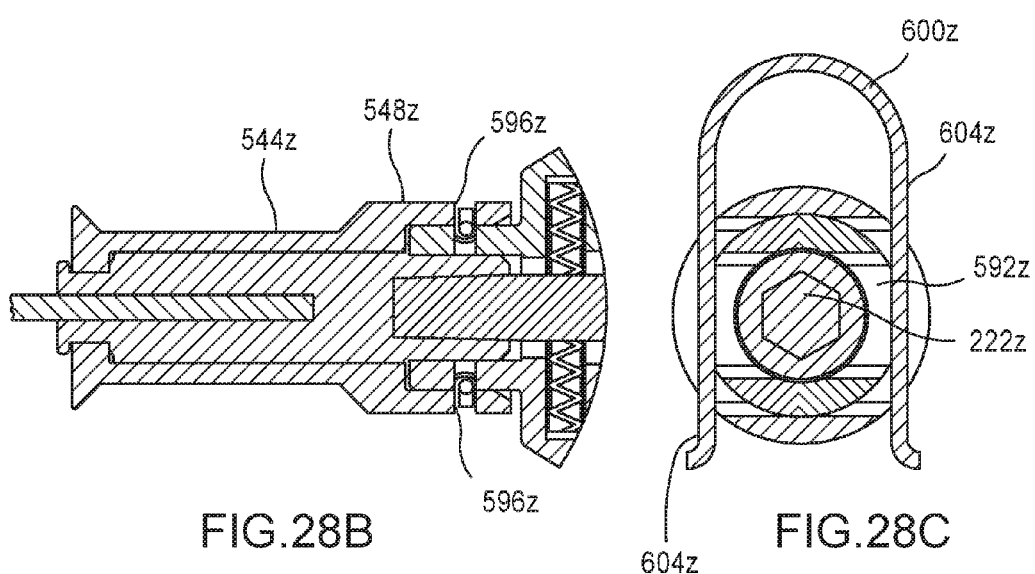

INTRAOSSEOUS DEVICE COUPLERS, DRIVERS, KITS, AND METHODS

BACKGROUND

1. Field of the Invention

The present invention relates generally to intraosseous (IO) access and, more particularly, but not by way of limitation, to couplers, drivers, IO devices (e.g., needle sets), and methods that can be used to facilitate IO access (e.g., to obtain bone marrow from the bone of a patient for biopsy and/or transplantation).

2. Description of Related Art

Examples of couplers, drivers, IO devices, and kits are disclosed, for example, in International Patent Application No. PCT/US2007/078207 (published as WO 2008/033874).

SUMMARY

This disclosure includes embodiments of couplers, drivers, IO devices, and kits.

Some embodiments of the present couplers comprise a drive hub having a first end and a second end configured to be coupled in fixed relation to a driveshaft of a driver having a housing such that at least a portion of the hub is disposed outside the housing of the driver; where the first end of the drive hub includes female threads configured to be coupled to an intraosseous (IO) device. In some embodiments, the second end of the drive hub comprises female threads configured to be coupled to the driveshaft of a driver. In some embodiments, the female threads in the second end of the drive hub are configured to tighten if a driver rotates the drive hub and an IO device coupled to the drive hub in a clockwise direction.

Some embodiments of the present couplers comprise a drive hub having a first end and a second end including a recess configured to receive a driveshaft of a driver; where the first end of the drive hub is configured to be coupled to an intraosseous (IO) device to resist rotation of the IO device relative to the drive hub; and where the second end of the drive hub is configured such that if a driveshaft is inserted into the recess, an interference fit between the drive hub and the driveshaft will resist rotation of the drive hub relative to the driveshaft. In some embodiments, the recess has a circular cross-sectional shape. In some embodiments, the recess is defined by a cylindrical wall. In some embodiments, the second end further includes a second recess surrounding at least a portion of the cylindrical wall. In some embodiments, the second end of the hub includes a plurality of tabs extending into the recess, the plurality of tabs being configured to deform if the driveshaft is inserted into the recess. In some embodiments, the plurality of tabs each has a triangular cross-sectional shape. In some embodiments, the recess has a circular central portion and one or more peripheral portions extending outwardly from the circular central portion. In some embodiments, the plurality of tabs extend into the peripheral portions of the openings. In some embodiments, the first end of the drive hub includes a recess and is configured such that if a hub of an IO device is inserted into the recess, an interference fit between the drive hub and the IO device will resist rotation of the IO device relative to the drive hub.

Some embodiments of the present couplers comprise a drive hub having a first end and a second end configured to be coupled in fixed relation to a driveshaft of a driver; where the first end of the drive hub has a recess configured to receive a portion of an intraosseous (IO) device; and where the first end of the drive hub is configured such that if a portion of the IO device is inserted into the recess, an interference fit between the drive hub and the IO device will resist rotation of the IO device relative to the drive hub. In some embodiments, the recess has a circular cross-sectional shape. In some embodiments, the recess is defined by a cylindrical wall. In some embodiments, the first end further includes a second recess surrounding at least a portion of the cylindrical wall. In some embodiments, the first end of the hub includes a plurality of tabs extending into the recess, the plurality of tabs configured to deform if the driveshaft is inserted into the recess. In some embodiments, the plurality of tabs each has a triangular cross-sectional shape. In some embodiments, the recess has a circular central portion and one or more peripheral portions extending outwardly from the circular central portion. In some embodiments, the plurality of tabs extend into the peripheral portions of the openings. In some embodiments, the second end of the drive hub includes a recess and is configured such that if the driveshaft is inserted into the recess, an interference fit between the drive hub and the driveshaft will resist rotation of the drive hub relative to the driveshaft.

Some embodiments of the present couplers comprise a drive hub having a first end and a second end including a recess configured to receive a driveshaft of a driver; and an adhesive disposed in the recess and configured to adhere to a driveshaft inserted into the recess; where the first end of the drive hub is configured to be coupled to an intraosseous (IO) device to resist rotation of the IO device relative to the drive hub; and where the recess has a cross-sectional shape corresponding to the cross-sectional shape of the driveshaft such that if the driveshaft is inserted into the second recess, the drive hub will resist rotating relative to the driveshaft. In some embodiments, the recess has a non-circular cross-sectional shape. In some embodiments, the first end of the drive hub includes a second recess configured to receive a hub of an IO device; the second recess has a cross-sectional shape corresponding to a cross-sectional shape of the hub of the IO device such that if the portion of the IO device is inserted into the recess, the drive hub will resist rotation of the IO device relative to the drive hub; and the coupler further comprises a second adhesive disposed in the second recess and configured to adhere to an IO device inserted into the second recess.

Some embodiments of the present couplers comprise a drive hub having a first end and a second end configured to be coupled in fixed relation to a driveshaft of a driver; where the first end of the drive hub has a recess configured to receive a portion of an intraosseous (IO) device; and where the recess has a cross-sectional shape corresponding to a cross-sectional shape of the portion of the IO device such that if the portion of the IO device is inserted into the recess, the drive hub will resist rotation of the IO device relative to the drive hub.

Some embodiments of the present couplers comprise a drive hub having a first end and a second end including a recess configured to receive a driveshaft of a driver; and a resilient clip biased toward an axis of rotation of the drive hub; where the first end of the drive hub is configured to be coupled to an intraosseous (IO) device to resist rotation of the IO device relative to the drive hub; and where the recess has a cross-sectional shape corresponding to a cross-sectional shape of the driveshaft such that if the driveshaft is inserted into the recess, the drive hub will resist rotating relative to the driveshaft. In some embodiments, the couplers comprise a hollow sleeve configured to be disposed around the recess such that a driveshaft inserted into the recess will be disposed in the hollow sleeve; where the resilient clip is unitary with the hollow sleeve. In some embodiments, the hollow sleeve and resilient clip comprise a single piece of sheet metal. In some embodiments, the distal end of the driveshaft has a non-circular cross-section.

Some embodiments of the present couplers comprise a drive hub having a first end and a second end including a recess configured to receive a driveshaft of a driver, the drive hub having a sidewall with at least one opening extending through the sidewall in communication with the recess, the at least one opening having an inner cross-sectional area at the recess that is smaller than an outer cross-sectional area spaced apart from the inner cross-sectional area; at least one ball movably disposed in the at least one opening in the drive hub; a resilient c-clip disposed around the drive hub such that the c-clip biases the at least one ball toward a rotational axis of the drive hub; where the first end of the drive hub is configured to be coupled to an intraosseous (IO) device to resist rotation of the IO device relative to the drive hub; and where the second end of the drive hub is configured such that if a driveshaft having at least one detent is inserted into the recess, the c-clip will (i) allow the at least one ball to move away from the rotational axis of the drive hub until the at least one detent aligns with the at least one ball, and (ii) press the at least one ball into the at least one detent when the at least one detent is aligned with the at least one ball to resist removal of the driveshaft from the recess. In some embodiments, the driveshaft and the recess each has a non-circular cross-sectional shape. In some embodiments, the drive hub has a circular outer cross-sectional shape. In some embodiments, the first end of the drive hub includes a second recess configured to receive a hub of an IO device, and the drive hub has at least one second opening extending through the sidewall in communication with the second recess, the at least one second opening having an inner cross-sectional area at the second recess that is smaller than an outer cross-sectional area spaced apart from the inner cross-sectional area; the coupler further comprising: at least one second ball movably disposed in the at least one second opening in the drive hub; a second resilient c-clip disposed around the drive hub such that the c-clip biases the at least one second ball toward a rotational axis of the drive hub; where the first end of the drive hub is configured such that if a hub of an IO device having at least one second detent is inserted into the recess, the second c-clip will (i) allow the at least one ball to move away from the rotational axis of the drive hub until the at least one second detent aligns with the at least one second ball, and (ii) press the at least one second ball into the at least one second detent when the at least one second detent is aligned with the at least one second ball to resist removal of the IO device from the recess.

Some embodiments of the present couplers comprise a drive hub having a first end and a second end configured to be coupled in fixed relation to a driveshaft of a driver, the first end including a recess configured to receive a hub of an IO device, the drive hub having a sidewall with at least one opening extending through the sidewall in communication with the recess, the at least one opening having an inner cross-sectional area at the recess that is smaller than an outer cross-sectional area spaced apart from the inner cross-sectional area; at least one ball movably disposed in the at least one opening in the drive hub; a resilient c-clip disposed around the drive hub such that the c-clip biases the at least one ball toward a rotational axis of the drive hub; where the second end of the drive hub is configured such that if a hub of an intraosseous (IO) device having at least one detent is inserted into the recess, the c-clip will (i) allow the at least one ball to move away from the rotational axis of the drive hub until the at least one detent aligns with the at least one ball, and (ii) press the at least one ball into the at least one detent when the at least one detent is aligned with the at least one ball to resist removal of the driveshaft from the recess. In some embodiments, the hub of the IO device and the recess each has a non-circular cross-sectional shape. In some embodiments, the drive hub has a circular outer cross-sectional shape.

Some embodiments of the present couplers comprise a drive hub having a first end and a second end configured to be coupled in fixed relation to a driveshaft of a driver, the first end including a recess configured to receive a hub of an IO device, the drive hub having a sidewall with at least one opening extending through the sidewall in communication with the recess, the at least one opening having an inner cross-sectional area at the recess that is smaller than an outer cross-sectional area spaced apart from the inner cross-sectional area; at least one ball movably disposed in the at least one opening in the drive hub; a collar movably disposed around the drive hub and having an interior surface defining at least one detent adjacent the drive hub; where the collar is movable between (i) a first position in which the at least one detent of the collar is aligned with the at least one opening such that the at least one ball can move away from the rotational axis of the drive hub to permit a hub of an intraosseous (IO) device having a detent to be inserted into or removed from the recess, and (ii) a second position in which the at least one detent of the collar is not aligned with the at least one opening such that if a hub of an IO device having at least one detent is disposed in the recess such that the at least one detent of the hub is aligned with the opening, the IO device is prevented from being removed from the recess. In some embodiments, the collar is biased toward the second position. In some embodiments, the hub of the IO device and the recess each has a non-circular cross-sectional shape. In some embodiments, the second end of the drive hub includes a second recess configured to receive a driveshaft of a driver, and the drive hub has at least one second opening extending through the sidewall in communication with the second recess, the at least one second opening having an inner cross-sectional area at the second recess that is smaller than an outer cross-sectional area spaced apart from the inner cross-sectional area; the coupler further comprising at least one second ball movably disposed in the at least one second opening in the drive hub; a second collar movably disposed around the drive hub and having an interior surface defining at least one second detent adjacent the drive hub; where the second collar is movable between (i) a first position in which the at least one second detent of the second collar is aligned with the at least one second opening such that the at least one second ball can move away from the rotational axis of the drive hub to permit a driveshaft having a detent to be inserted into or removed from the second recess, and (ii) a second position in which the at least one second detent of the collar is not aligned with the at least one second opening such that if driveshaft of a driver having at least one second detent is disposed in the second recess such that the at least one second detent is aligned with the opening, the driveshaft is prevented from being removed from the recess.

Some embodiments of the present couplers comprise a drive hub having a first end and a second end including a recess configured to receive a driveshaft of a driver, the drive hub having a sidewall with at least one opening extending through the sidewall in communication with the recess; at least one set screw with a spring-loaded ball, the at least one set screw disposed in the at least one opening in the drive hub such that the ball is biased in a direction toward an axis of rotation of the drive hub; where the first end of the drive hub is configured to be coupled to an intraosseous (IO) device to resist rotation of the IO device relative to the drive hub; and where the second end of the drive hub is configured such that if a driveshaft having at least one detent is inserted into the recess (i) the spring-loaded ball of the at least one set screw will move away from the rotational axis of the drive hub until the at least one detent aligns with the at least one ball, and (ii) the spring-loaded ball of the at least one set screw will move into the at least one detent when the at least one detent is aligned with the at least one ball to resist removal of the driveshaft from the recess. In some embodiments, the driveshaft and the recess each has a non-circular cross-sectional shape. In some embodiments, where the first end of the drive hub includes a second recess configured to receive a hub of an IO device, and the drive hub has at least one second opening extending through the sidewall in communication with the second recess; the coupler further comprising at least one second set screw with a spring-loaded ball, the at least one second set screw disposed in the at least one second opening in the drive hub such that the ball is biased in a direction toward an axis of rotation of the drive hub; where the second end of the drive hub is configured such that if a hub of an IO device having at least one second detent is inserted into the recess (i) the spring-loaded ball of the at least one second set screw will move away from the rotational axis of the drive hub until the at least one second detent aligns with the at least one ball, and (ii) the spring-loaded ball of the at least one second set screw will move into the at least one second detent when the at least one detent is aligned with the at least one second ball to resist removal of the IO device from the recess.

Some embodiments of the present couplers comprise a drive hub having a first end and a second end configured to be coupled in fixed relation to a driveshaft of a driver, the first end including a recess configured to receive a hub of an intraosseous (IO) device, the drive hub having a sidewall with at least one opening extending through the sidewall in communication with the recess; at least one set screw with a spring-loaded ball, the at least one set screw disposed in the at least one opening in the drive hub such that the ball is biased in a direction toward an axis of rotation of the drive hub; where the first end of the drive hub is configured such that if a hub of an IO device having at least one detent is inserted into the recess (i) the spring-loaded ball of the at least one set screw will move away from the rotational axis of the drive hub until the at least one detent aligns with the at least one ball, and (ii) the spring-loaded ball of the at least one set screw will move into the at least one detent when the at least one detent is aligned with the at least one ball to resist removal of the IO device from the recess. In some embodiments, the hub of the IO device and the recess each has a non-circular cross-sectional shape.

Some embodiments of the present couplers comprise a drive hub having a first end and a second end including a recess configured to receive a driveshaft of a driver, the drive hub having a sidewall with an opening extending through the sidewall in communication with the recess; a screw having an enlarged head and a threaded shaft with a distal end, the screw threaded into the opening with the distal end facing in a direction toward an axis of rotation of the drive hub; where the first end of the drive hub is configured to be coupled to an intraosseous (IO) device to resist rotation of the IO device relative to the drive hub; and where the screw is rotatable between (i) a first position in which the distal end does not extend into the recess to permit a driveshaft having a detent to be inserted into or removed from the recess, and (ii) a second position in which the distal end extends into the recess such that if a driveshaft having a detent is disposed in the recess such that the detent of the driveshaft is aligned with the opening, the driveshaft is prevented from being removed from the recess. In some embodiments, the driveshaft and the recess each has a non-circular cross-sectional shape. In some embodiments, the first end of the drive hub includes a second recess configured to receive a hub of an IO device, and the drive hub has a second opening extending through the sidewall in communication with the second recess; the coupler further comprising a second screw having an enlarged head and a threaded shaft with a distal end, the screw threaded into the second opening with the distal end facing in a direction toward an axis of rotation of the drive hub; where the second screw is rotatable between (i) a first position in which the distal end does not extend into the second recess to permit a hub of an IO device having a detent to be inserted into or removed from the recess, and (ii) a second position in which the distal end extends into the second recess such that if a hub of an IO device having a detent is disposed in the recess such that the detent of the hub is aligned with the opening, the IO device is prevented from being removed from the recess.

Some embodiments of the present couplers comprise a drive hub having a first end and a second end configured to be coupled in fixed relation to a driveshaft of a driver, the first end including a recess configured to receive a hub of an intraosseous (IO) device, the drive hub having a sidewall with an opening extending through the sidewall in communication with the recess; a screw having an enlarged head and a threaded shaft with a distal end, the screw threaded into the opening with the distal end facing in a direction toward an axis of rotation of the drive hub; where the screw is rotatable between (i) a first position in which the distal end does not extend into the recess to permit a hub of an IO device having a detent to be inserted into or removed from the recess, and (ii) a second position in which the distal end extends into the recess such that if a hub of an IO device having a detent is disposed in the recess such that the detent of the hub is aligned with the opening, the IO device is prevented from being removed from the recess.

Some embodiments of the present couplers comprise a drive hub having a first end and a second end including a recess configured to receive a driveshaft of a driver, the drive hub having a sidewall with an opening extending through the sidewall in communication with the recess; a pin having a distal end configured to be inserted into the opening such that the pin extends across a majority of a width of the recess; where the first end of the drive hub is configured to be coupled to an intraosseous (IO) device to resist rotation of the IO device relative to the drive hub; and where the pin is movable between (i) a first position in which the distal end does not extend into the recess to permit a driveshaft having a transverse passageway to be inserted into or removed from the recess, and (ii) a second position in which the pin extends into and across a majority of the recess such that if a driveshaft having a transverse passageway is disposed in the recess such that the transverse passageway is aligned with the opening, the pin extends into the transverse passageway to prevent the driveshaft from being removed from the recess. In some embodiments, the driveshaft and the recess each has a non-circular cross-sectional shape. In some embodiments, the first end of the drive hub includes a second recess configured to receive a hub of an IO device, and the drive hub has a second opening extending through the sidewall in communication with the second recess; the coupler further comprising a second pin having a distal end configured to be inserted into the second opening such that the pin extends across a majority of a width of the second recess; where the second pin is movable between (i) a first position in which the distal end does not extend into the second recess to permit a driveshaft having a transverse passageway to be inserted into or removed from the second recess, and (ii) a second position in which the second pin extends into and across a majority of the second recess such that if a hub of an IO device having a transverse passageway is disposed in the second recess such that the transverse passageway is aligned with the opening, the pin extends into the transverse passageway to prevent the IO device from being removed from the second recess.

Some embodiments of the present couplers comprise a drive hub having a first end and a second end configured to be coupled in fixed relation to a driveshaft of a driver, the first end including a recess configured to receive a hub of an intraosseous (IO) device, the drive hub having a sidewall with an opening extending through the sidewall in communication with the recess; a pin having a distal end configured to be inserted into the opening such that the pin extends across a majority of a width of the recess; where the pin is movable between (i) a first position in which the distal end does not extend into the recess to permit a hub of an IO device having a transverse passageway to be inserted into or removed from the recess, and (ii) a second position in which the pin extends into and across a majority of the recess such that if a hub of an IO device having a transverse passageway is disposed in the recess such that the transverse passageway is aligned with the opening, the pin extends into the transverse passageway to prevent the IO device from being removed from the recess.

Some embodiments of the present couplers comprise a drive hub having a first end and a second end configured to be coupled in fixed relation to a driveshaft of a driver; a resilient clamp having a substantially circular interior, the clamp configured to be movable between (i) a contracted position in which the interior has a first transverse dimension, and (ii) an expanded position in which the interior has a second transverse dimension that is larger than the first transverse dimension, where the resilient clamp is biased toward the contracted position; where the first end of the drive hub has a transverse dimension that is larger than the first transverse dimension of the clamp, and that is larger than a transverse dimension of the driveshaft; where the first end of the drive hub is configured to abut an intraosseous (IO) device such that the clamp can be disposed around the drive hub and the IO device to resist separation of the IO device from to the drive hub. In some embodiments, the drive hub has a cross-section with a circular central portion and a projection extending from the central portion in a direction away from a rotational axis of the drive hub. In some embodiments, the drive hub is not configured to receive a portion of the IO device. In some embodiments, the drive hub is configured to abut an IO device such that the clamp can be disposed around and in contact with the drive hub and the IO device to resist separation of the IO device from the drive hub. In some embodiments, the first end of the drive hub includes a sidewall defining a recess configured to receive a hub of the IO device, the sidewall having at least one slot extending through the sidewall in communication with the recess in the first end. In some embodiments, the second end of the drive hub includes a sidewall defining a recess configured to receive a driveshaft of a driver, the sidewall having at least one slot extending through the sidewall in communication with the recess in the second end, the coupler further comprising a second resilient clamp having a substantially circular interior, the second clamp configured to be movable between (i) a contracted position in which the interior has a first transverse dimension, and (ii) an expanded position in which the interior has a second transverse dimension that is larger than the first transverse dimension, where the second resilient clamp is biased toward the contracted position; where the second end of the drive hub has a transverse dimension that is larger than the first transverse dimension of the clamp, and that is larger than a transverse dimension of the driveshaft; where the recess in the second end of the drive hub is configured to receive a driveshaft of a driver such that the clamp can be disposed around the drive hub and the driveshaft to resist separation of the drive hub from the driveshaft.

Some embodiments of the present couplers comprise a drive hub having a first end and a second end including a sidewall defining a recess configured to receive a driveshaft of a driver, the sidewall having at least one slot extending through the sidewall in communication with the recess in the second end; a resilient clamp having a substantially circular interior, the clamp configured to be movable between (i) a contracted position in which the interior has a first transverse dimension, and (ii) an expanded position in which the interior has a second transverse dimension that is larger than the first transverse dimension, where the resilient clamp is biased toward the contracted position; where the second end of the drive hub has a transverse dimension that is larger than the first transverse dimension of the clamp; and where the recess is configured to receive a driveshaft of a driver such that the clamp can be disposed around the drive hub and the driveshaft to resist separation of the drive hub from the driveshaft. In some embodiments, the recess is configured to receive a driveshaft of a driver such that the clamp can be disposed around and in contact with the drive hub and the driveshaft to resist separation of the drive hub from the driveshaft.

Some embodiments of the present couplers comprise a drive hub having a first end and a second end configured to be coupled in fixed relation to a driveshaft of a driver, the first end including a plurality of movable prongs configured to grasp a hub of an intraosseous (IO) device; a collar movably disposed around the drive hub; where the collar is movable between (i) a first position in which the plurality of prongs can move away from the rotational axis of the drive hub to permit an IO device to be inserted into or removed from the plurality of prongs, and (ii) a second position in which the collar constrains the plurality of prongs such that if a hub of an IO device is disposed between the plurality of prongs, the prongs resist removal of the IO device from the plurality of prongs. In some embodiments, the collar is biased toward the second position. In some embodiments, the second end of the drive hub includes including a second plurality of movable prongs configured to grasp a driveshaft of a driver, the coupler further comprising a second collar movably disposed around the drive hub; where the second collar is movable between (i) a first position in which the second plurality of prongs can move away from the rotational axis of the drive hub to permit a driveshaft to be inserted into or removed from the second plurality of prongs, and (ii) a second position in which the second collar constrains the second plurality of prongs such that if a hub of an IO device is disposed between the second plurality of prongs, the second plurality of prongs resists removal of IO device from the second plurality of prongs.

Some embodiments of the present couplers comprise a drive hub having a first end and a second end including a recess configured to receive a driveshaft of a driver, the recess having a proximal end and a distal end; a magnetic ring disposed around a perimeter of the recess between the proximal end of the recess and the distal end of the recess; where the first end of the drive hub is configured to be coupled to an intraosseous (IO) device to resist rotation of the IO device relative to the drive hub. In some embodiments, the recess has a non-circular cross-sectional shape. In some embodiments, the magnetic ring defines a step within the recess. In some embodiments, the first end of the drive hub includes a second recess configured to receive a driveshaft of a driver, the recess having a proximal end and a distal end, the coupler further comprising a second magnetic ring disposed around a perimeter of the second recess between the proximal end of the second recess and the distal end of the second recess. In some embodiments, the recess has a non-circular cross-sectional shape. In some embodiments, the second magnetic ring defines a step within the second recess. In some embodiments, the second end of the drive hub comprises a flange extending outwardly relative to an axis of rotation of the drive hub.

Some embodiments of the present drivers comprise a housing; a power source; a driveshaft coupled to the power source such that the power source can cause the driveshaft to rotate; and a coupler of having any of the disclosed features or characteristics, where the drive hub is configured to be coupled to the driveshaft such that at least a portion of the drive hub is disposed outside the housing. In some embodiments, a portion of the driveshaft is tapered. In some embodiments, the drive hub is unitary with the driveshaft. In some embodiments, the power source comprises a spring. In some embodiments, the drivers further comprise an electric motor coupled to the driveshaft and the power source. In some embodiments, the driveshaft has a distal end including male threads corresponding to the female threads in the second end of the drive hub. In some embodiments, the driveshaft has a distal end with a non-circular cross-sectional shape. In some embodiments, the distal end of the driveshaft comprises one or more projections extending outward relative to an axis of rotation of the driveshaft. In some embodiments, the distal end of the driveshaft has a cross-section that is a different shape than a cross-section of the recess in the second end of the drive hub. In some embodiments, the driveshaft comprises a cross-section with a circular central portion and a projection extending from the central portion in a direction away from a rotational axis of the driveshaft. In some embodiments, the drivers comprise an element comprising at least one of a magnet and a magnetically-attractive material, the element coupled to the driveshaft and spaced apart from the distal end of the driveshaft; where the element of the driver is configured to magnetically couple to the magnetic ring of the coupler if the driveshaft is inserted into the recess in the second end of the coupler. In some embodiments, the element is disposed within the driveshaft. In some embodiments, the element comprises a ring disposed around the driveshaft.

Some embodiments of the present drivers comprise a housing having a body portion and a shroud portion, the body portion having a sidewall defining a distal end, and the shroud portion having a cylindrical sidewall extending from the distal end of the body portion, the shroud portion having an open distal end; a power source; and a driveshaft disposed in the body portion of the housing and coupled to the power source such that the power source can cause the driveshaft to rotate, the driveshaft having a distal end extending from the body portion and into the shroud portion; where the driver is configured to be coupled to an IO device having a hub with a recess sized to receive the distal end of the driveshaft, such that the distal end of the driveshaft extends into the recess and the hub of the IO device is at least partially disposed in the shroud portion of the housing. In some embodiments, the drivers comprise a plate having an opening, the plate disposed in the shroud portion of the housing with the driveshaft aligned with the opening such that the plate is movable within the shroud along a length of the driveshaft; and a spring disposed between the plate and the distal end of the body portion of the housing such that the spring biases the plate in a direction toward the open end of the shroud portion. In some embodiments, the shroud portion comprises a lip extending inward toward the driveshaft and configured to prevent the plate from exiting the shroud portion. In some embodiments, the shroud portion of the housing has one or more projections extending in a direction away from the driveshaft. In some embodiments, the one or more projections comprise two projections extending in opposite directions. In some embodiments, the shroud portion comprises one or more resilient portions and one or more substantially rigid portions, and the one or more projections extend from the one or more resilient portions such that the one or more projections are movable relative to the driveshaft. In some embodiments, the shroud portion has two elongated grooves in an outer surface of the cylindrical sidewall, the two elongated grooves extending in a direction that is substantially perpendicular to rotational axis of the driveshaft.

Some embodiments of the present kits comprise a driver having any of the disclosed features or characteristics and an intraosseous (IO) device comprising a first hub having a cannula coupled in fixed relation to the hub, the cannula having a distal end extending from a distal of the hub; where the IO device is configured to be coupled to the first end of the drive hub of the coupler. As described below, any couplers having the disclosed features or characteristics may be included. In some embodiments, the IO device is configured to be coupled to the first end of the drive hub such that the drive hub contacts the first hub of the IO device. In some embodiments, the IO device further comprises a second hub configured to be coupled to the first hub. In some embodiments, the second hub has a trocar with a distal end extending from the second hub, and the second hub is configured to be coupled to the first hub such that the trocar extends through a longitudinal passage of the trocar. In some embodiments, the IO device is configured to be coupled to the first end of the drive hub of the coupler such that the drive hub contacts the second hub of the IO device. In some embodiments, the second hub of the IO device is unitary with the drive hub of the coupler. In some embodiments, the second hub of the IO device comprises male threads corresponding to female threads of the drive hub. In some embodiments, the second hub of the IO device has a non-circular cross-sectional shape. In some embodiments, the second hub of the IO device comprises one or more projections extending outward relative to an axis of rotation of the IO device. In some embodiments, the second end of the drive hub has a cross-section that is a different shape than a cross-section of the recess in the first end of the drive hub. In some embodiments, the first hub is configured to be inserted into the recess in the first end of the drive hub of the coupler. In some embodiments, the second hub is configured to be inserted into the recess in the first end of the drive hub. In some embodiments, the second hub comprises a projection with at least one detent. In some embodiments, the second hub comprises a projection with a transverse passageway extending transversely across at least a portion of the projection. In some embodiments, the kits can comprise a sleeve configured to be rotatably coupled to one or more of the first hub and the second hub of the IO device, the sleeve including a proximal portion configured to fit over the shroud portion of the housing to couple the IO device to the driver. In some embodiments, the proximal portion of the sleeve comprises one or more L-shaped slots configured to receive the one or more projections if the proximal portion of the sleeve is disposed over the shroud portion of the housing such that the sleeve can be rotated relative to the shroud portion to resist removal of the IO device from the driver. In some embodiments, the proximal portion of the sleeve includes an interior surface defining one or more detents configured to receive the one or more projections of the shroud portion. In some embodiments, the kits can further comprise a sleeve rotatably coupled to one or more of the first hub and the second hub of the IO device, the sleeve including a proximal portion configured to fit over the shroud portion of the housing if the IO device is coupled to the driver; and a resilient U-shaped clip having two legs; where the proximal portion of the sleeve comprises two elongated openings configured to align with the elongated grooves in the shroud portion if the proximal portion of the sleeve is disposed on the shroud portion; and where the clip is configured to extend over the proximal portion of the sleeve with the two legs extending through the elongated openings in the sleeve and into the elongated grooves to resist removal of the sleeve and IO device from the driver. In some embodiments, the second hub comprises a cross-section with a circular central portion and a projection extending from the central portion in a direction away from a rotational axis of the second hub.

Any embodiment of any of the devices, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The embodiments of the present drivers, coupler assemblies, intraosseous (IO) devices, and their components shown in the figures are drawn to scale for at least the embodiments shown.

FIGS. 6A-6E depict various views of a fourth embodiment of the present couplers in combination with a powered driver and an IO device.

FIGS. 10A-10D depict various views of an eighth embodiment of the present couplers in combination with a powered driver and an IO device.

FIGS. 28A-28C depict various views of a twenty-fourth embodiment of the present couplers in combination with a powered driver and an IO device.

DESCRIPTION OF ILLUSTRATIVE EMBODIMENTS

Figure 1A:
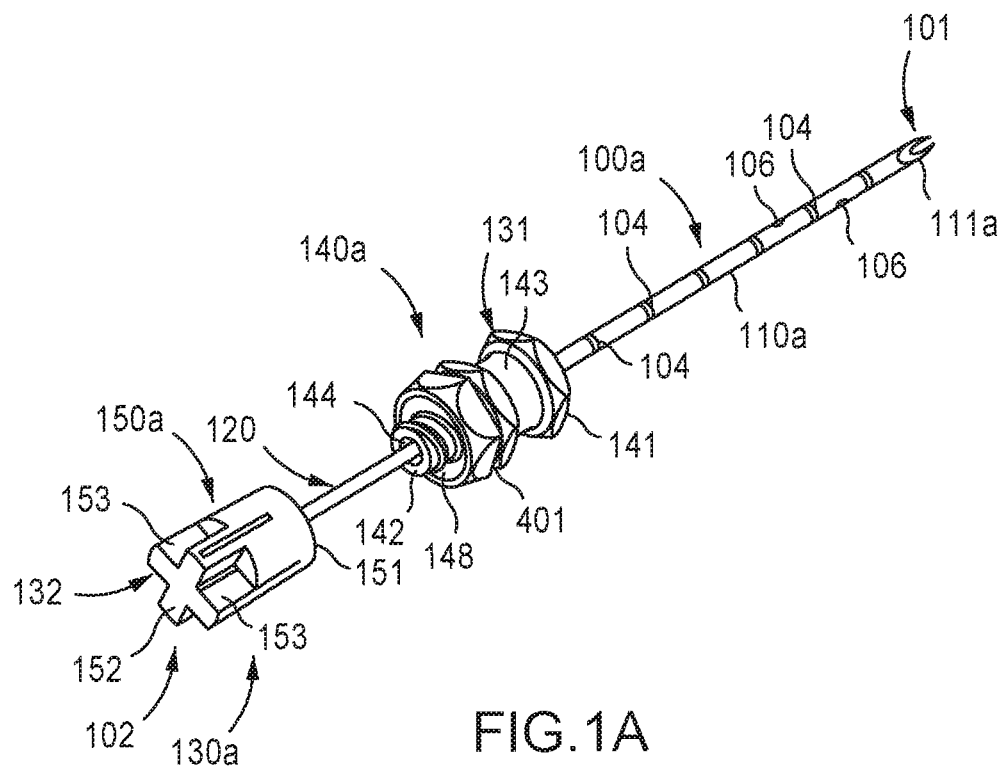
FIG. 1A depicts a perspective view of one embodiment of the present intraosseous devices having a first embodiment of a cannula and a first embodiment of a stylet.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a driver or coupler assembly that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, a device or system (or an element of a device or system) that is configured in a certain way is configured in at least that way, but it can also be configured in other ways than those specifically described.

Various types of coupler assemblies incorporating teachings of the present disclosure may be satisfactorily used to releasably engage one end of a shaft extending from a driver with one end of an intraosseous device. For some embodiments, the powered driver may include a driveshaft having one end with a non-circular (e.g., generally hexagonal) cross section operable to be releasably engaged with a latch mechanism disposed proximate (e.g., in) one end of a coupler assembly. For some embodiments, a coupler assembly incorporating teachings of the present disclosure may be referred to as a "hands free" coupler, a quick disconnect or quick release coupler, and/or a port assembly.

A powered driver may be used to insert an IO device incorporating teachings of the present disclosure into a selected target area or target site in ten seconds or less. However, various teachings of the present disclosure are not limited to use with powered drivers. Manual drivers and spring powered drivers may also be used with IO devices incorporating teachings of the present disclosure.

Examples of manual drivers are shown in co-pending patent application Ser. No. 11/042,912 entitled Manual Intraosseous Device filed Jan. 25, 2005 (published as US 2005/0165404). The term "fluid" may be used in this application to include liquids such as, but not limited to, blood, water, saline solutions, IV solutions, plasma, or any mixture of liquids, particulate matter, dissolved medication, and/or drugs associated with biopsy or aspiration of bone marrow or communication of fluids with bone marrow or other target sites. The term "fluid" may also be used in this patent application to include any body fluids and/or liquids containing particulate matter such as bone marrow and/or cells that may be withdrawn from a target area.

The terms "harvest" and "harvesting" may be used in this application to include bone and/or bone marrow biopsy and bone marrow aspiration. Bone and/or bone marrow biopsy (sometimes referred to as "needle biopsy") may be generally described as removing a relatively small piece or specimen of bone and/or bone marrow from a selected target area for biopsy purposes. Bone marrow aspiration (sometimes referred to as "bone marrow sampling") may be generally described as removing larger quantities of bone marrow from a selected target area. Relatively large quantities of bone marrow may be used for diagnostic, transplantation, and/or research purposes. For example, some stem cell research techniques may require relatively large quantities of bone marrow.

The terms "insertion site," "penetration site," and "installation site" may be used in this application to describe a location on a bone at which an intraosseous device may be inserted or drilled into the bone and associated bone marrow.

Insertion sites, penetration sites, and installation sites are generally covered by skin and soft tissue.

The term "intraosseous (IO) device" may be used in this application to include, but is not limited to, any hollow needle, hollow drill bit, penetrator assembly, bone penetrator, catheter, cannula, trocar, stylet, inner penetrator, outer penetrator, IO needle, biopsy needle, aspiration needle, IO needle set, biopsy needle set, or aspiration needle set operable to provide access to an intraosseous space or interior portions of a bone. Such IO devices may be formed, at least in part, from metal alloys such as 304 stainless steel and other biocompatible materials associated with needles and similar medical devices.

Embodiments of the present coupler assemblies can be included in medical procedure trays, such as those disclosed in International Patent Application No. PCT/US2007/078207 (published as WO 2008/033874).

Referring now to the drawings, and more particularly to FIG. 1A, shown therein and designated by the reference numeral 100 is one embodiment of the present intraosseous (IO) needle sets or aspiration needle sets. Aspiration needle set 100*a* comprises a hollow outer penetrator or cannula 110*a*, a corresponding inner penetrator or stylet (or trocar) 120, and a hub assembly 130*a*. In the embodiment shown, first end 111*a* of cannula 110*a* and first end 121 of stylet 120 are operable or configured to penetrate a bone and associated bone marrow. Various features of first end 111*a* of cannula 110*a* and first end 121 of stylet 120 are shown in more detail in FIGS. 1B-1D. First end 101 of IO needle set 100 corresponds generally with first end 111*a* of cannula 110*a* and first end 121 of stylet 120.

In the embodiment shown, cannula 110*a* includes a plurality of markings 104 disposed on exterior portions of the cannula. Markings 104 may be referred to as "positioning marks" or "depth indicators," and may be used to indicate the depth of penetration of needle set 100 into a bone and associated bone marrow. In some embodiments, cannula 110*a* may have a length of approximately sixty (60) millimeters and/or a nominal outside diameter of approximately 0.017 inches (e.g., corresponding generally to the dimensions of a sixteen (16) gauge needle). Cannula 110*a* and/or stylet 120 may be formed from stainless steel or other suitable biocompatible materials. In some embodiments, markings 104 are spaced at one (1) centimeter intervals on exterior portions of cannula 110*a*. In some embodiments, one or more side ports 106 may be formed in exterior portions of cannula 110*a* spaced from first end 111*a*.

Hub assembly 130*a* may be configured and/or used to releasably dispose stylet 120 within the longitudinal bore or lumen of cannula 110*a*. In the embodiment shown, hub assembly 130*a* includes a first hub 140*a* and a second hub 150*a*. A second end of cannula 110*a*, opposite from first end 111*a*, may be securely engaged with hub 140*a*. The second end of stylet 120, opposite from first end 121, may be securely engaged with the first end of hub 150*a*. As shown in FIG. 1A, cannula 110*a* may extend longitudinally from first end 141 of hub 140*a*. Stylet 120 may also extend from the first end of hub 150*a*. The second end of hub 140*a* may include a standard Luer lock fitting which may be releasably engaged with a corresponding Luer lock fitting disposed within the first end of second hub 150*a*. The Luer lock fitting disposed on the second end of hub 140*a* may be in fluid communication with the bore or passage in cannula 110*a*, and may be operable to be releasably engaged with a standard syringe type fitting and/or a standard intravenous (IV) connection. In the embodiment shown, hub 150*a* includes second end 152 that generally corresponds with second end 132 of hub assembly 130*a* and second end 102 of IO needle set 100. Hub 140*a* may include first end 141 which may generally correspond with first end 131 of hub assembly 130*a*. Cannula 110*a* may extend longitudinally from first end 141 of hub 140*a* and first end 131 of hub assembly 130.

In the embodiment shown, the second end of a hub assembly may be operable to be disposed within a receptacle formed in a coupler assembly, as described in more detail below. One feature of the present disclosure may include forming a hub assembly which may be releasably engaged within a first receptacle disposed in a first end of a coupler assembly (e.g., receptacle 263 proximate first end 261 of elongated core 260 as shown in FIGS. 6A-6B of International Patent Application No. PCT/US2007/078207 (published as WO 2008/033874)). The dimensions and configuration of receptacle 263 may be selected to prevent rotation of hub 150*a* relative to hub 140*a* if hub assembly 130*a* is disposed in receptacle 263 (e.g., while inserting (rotating) an IO device into a bone and associated bone marrow). A powered driver may be releasably engaged with a second receptacle disposed in a second end of the coupler assembly (e.g., receptacle 264 proximate second end 262 of elongated core 260 as shown in FIGS. 6A-6B of International Patent Application No. PCT/US2007/078207 (published as WO 2008/033874)).

In the embodiment shown, intraosseous device or aspiration needle set 100*a* includes first end 151 of hub 150*a* spaced from second end 142 of hub 140*a*. Portions of stylet 120 extending from first end 151 of hub 150*a* are shown slidably disposed within lumen or longitudinal bore 118 of cannula 110*a*. Hub assembly 130*a* may include first end 131 which may correspond generally with first end 141 of hub 140*a*. Hub assembly 130*a* may also include second end 132 which may correspond generally with second end 152 of hub 150*a* and second end 102 of hub assembly 130*a*, as shown. Cannula 110*a* may be attached to and extend from first end 141 of hub 140*a*. Second end 142 of hub 140*a* may include one-half a typical Luer lock connection or fitting operable to be releasably engaged with corresponding portions of a Luer lock connection or fitting disposed in first end 151 of second hub 150*a*. For embodiments such as the one shown in FIG. 1A, first end 131 of hub assembly 130*a* may correspond with first end 141 of first hub 140*a*. Second end 152 of second hub 150*a* may correspond with second end 132 of hub assembly 130*a* and second end 102 of aspiration needle set 100*a*.

At least one portion of hub assembly 130*a* may have a generally hexagonal cross section operable to be received within the generally hexagonal cross section of receptacle 263 disposed proximate first end 251 of coupler assembly 250, as shown in FIGS. 6A-6B of International Patent Application No. PCT/US2007/078207 (published as WO 2008/033874). For some embodiments, portions of first hub 140*a* disposed adjacent to reduced outside diameter portion 143 may have generally hexagonal cross sections, as shown in FIG. 1A. In other embodiments, various cross sections other than hexagonal may be satisfactorily used to releasably engage a powered driver with one end of a coupler assembly and an intraosseous device with an opposite end of the coupler assembly. Aspiration needle sets may include a trocar, stylet or penetrator in combination with an associated cannula, catheter or outer penetrator. However, biopsy needles formed in accordance with teachings of the present disclosure may or may not include a trocar, stylet or inner penetrator.

Hub 140a may include second end 142 with opening 144 formed therein. A passageway may extend from second end 142 towards first end 141 of hub 140a, as illustrated in FIGS. 6A-6B of International Patent Application No. PCT/US2007/078207 (published as WO 2008/033874). A passageway may be operable to communicate fluids with lumen 118 of cannula 100a. Second end 142 of hub 140 may include various features of a conventional Luer lock connection or fitting, including threads 148, and corresponding threads 158 may be formed within first end 151 of hub 150a, as shown in FIGS. 6A-6B of International Patent Application No. PCT/US2007/078207 (published as WO 2008/033874).

For some applications hub 140a and hub 150a may, for example, be formed using injection molding techniques. For such embodiments hub 140a may include reduced outside diameter portion 143 disposed between first end 141 and second end 142. In a similar manner a plurality of void spaces or cutouts 153 may be formed in hub 150a adjacent to and extending from second end 152 in the direction of first end 151. The configuration and dimensions of reduced diameter portion 143 and/or cutouts 153 may be varied to optimize associated injection molding techniques and at the same time provide required configurations, dimensions and material strength to allow associated hub assembly 130a to function as described in this disclosure.

In some embodiments, tip 123 of stylet 120 may be disposed relatively close to a tip of cannula 110a. For some applications, first end 121 of trocar 120 and first end 111a of cannula 110a may be ground at the same time to form adjacent cutting surfaces. Grinding ends 111a and 121 at the same time may result in forming a single cutting unit to form generally matching cutting edges. Other types of cutting surfaces formed in accordance with teachings of the present disclosure may be discussed later (e.g., as described with reference to FIGS. 1B-1D).

Figure 1B:
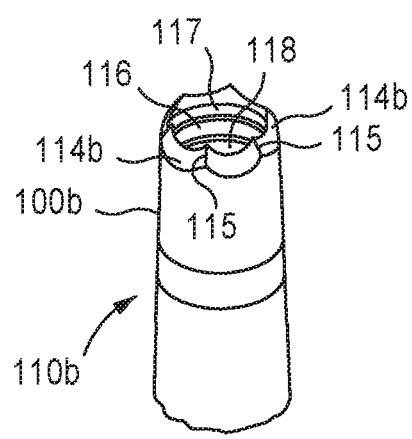
FIG. 1B depicts a perspective view of a second embodiment of the present cannulas.
Figure 1C:
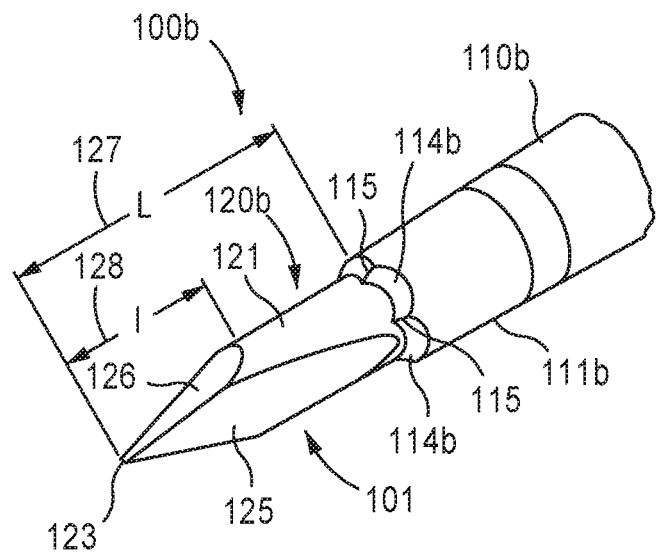
FIGS. 1C and 1D depict a perspective views of a third embodiment of the present IO devices having a second embodiment of the present stylets disposed in the cannula of FIG. 2.
Figure 1D:
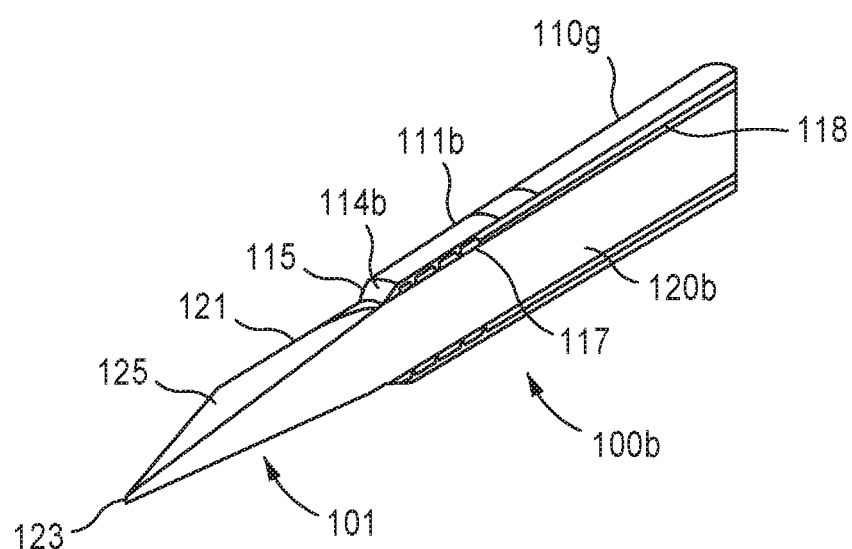

FIGS. 1B-1D show a second example of cutting surfaces and tips which may be formed adjacent to the ends of a cannula and/or an associated trocar in the present embodiments. In the embodiment shown, outer penetrator or cannula 110b may include first end 111b having a plurality of cutting surfaces 114b formed adjacent to opening 116 in first end 111. Opening 116 may communicate with and form a portion of an associated longitudinal bore or lumen 118. For some applications cutting surfaces 114b may be formed using electrical discharge machining (EDM) techniques or otherwise, as described in WO 2008/033874. In the embodiment shown, first end 111b has a generally tapered configuration or reduced outside diameter as compared with other portions of cannula 110b In other embodiments, first end 111b has an outside diameter that is equal to the outside diameter of other portions of cannula 110b (e.g., cannula 110b can have a constant outside diameter along the entire length of the cannula). Cutting surfaces 114b may, for example, be formed using machine grinding techniques. In some embodiments, such as the one shown, end 111b of cannula 110b may include six ground cutting surfaces 114b with respective crowns 115 therebetween. Forming a biopsy needle set and/or biopsy needle with tapered end 111b and a plurality of cutting surfaces 114b and crowns 115 may provide improved drilling performance (e.g., relative to others configurations) when the resulting biopsy needle set and/or biopsy needle is used with a powered driver in accordance with teachings of the present disclosure. For some applications, a helical groove 117 may be formed within longitudinal bore 118 proximate opening 116. Helical groove 117 may assist with retaining a biopsy specimen or a bone marrow specimen within longitudinal bore 118. For example, a single thread may be disposed within the longitudinal bore or lumen of the cannula such that the helical groove 117 is defined between turns of the thread. Various techniques and procedures may be satisfactorily used to place the single thread or otherwise form the helical groove, as described WO 2008/033874.

As shown in FIG. 1C, a biopsy needle set 100b may include cannula or outer penetrator 110b with stylet or inner penetrator 120b slidably disposed therein. The proximal ends of cannula 110b and stylet 120b may be similar to those of cannula 110a and stylet 120 depicted in FIG. 1A (e.g., may include hubs 140a and 150a, respectively). For some applications first end 101 of biopsy needle set 100b may minimize damage to skin and soft body tissue at an insertion site. For some applications inner penetrator or trocar 120b may include first end 121 having a plurality of cutting surfaces 125 and 126 formed on exterior portions thereof extending from associated tip 123 towards second end of trocar or inner penetrator 120b. For some applications one or more cutting surfaces 125 may be formed having length 127 extending from tip 123 to associated cutting surfaces 114b in associated cannula 110b. One or more cutting surfaces 126 may be formed adjacent to each cutting surface 125 with second length 128. First length 127 may be greater than second length 128. As shown, lengths 127 and 128 are measured parallel to the central longitudinal axis of stylet 120b. The ratio of first length 127 and second length 128 may be varied in accordance with teachings of the present disclosure to provide optimum performance for penetrating a selected bone and associated bone marrow. Additional details of some embodiments of first end 101 are described in WO 2008/033874.

Figure 1E:
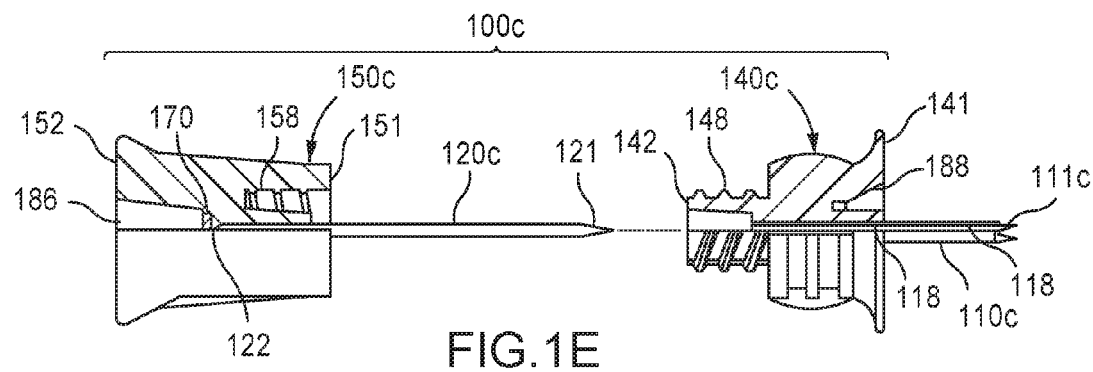
FIGS. 1E and 1F depict perspective views of a fourth embodiment of the present IO devices having a stylets, trocars, or inner penetrators disposed in a cannula or outer penetrator.
Figure 1F:
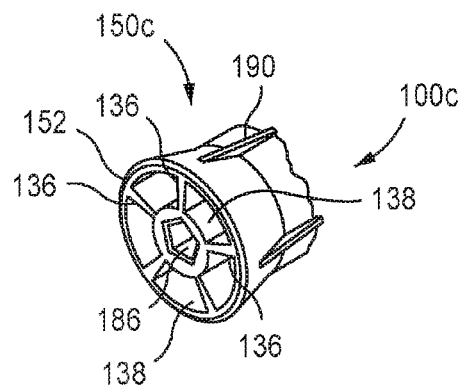

FIGS. 1E and 1F depict perspective views of a fourth embodiment of the present IO devices having a stylets, trocars, or inner penetrators disposed in a cannula or outer penetrator. In the embodiment shown, device 100a is configured to provide access to a patient's circulatory system via the patient's bone (e.g., as opposed to extracting a bone-marrow sample). In the embodiment shown, device or penetrator assembly 100c may include first hub 140c, connector or second hub 150c, outer penetrator 110c, and inner penetrator 120c. Penetrator assembly 100c may include an outer penetrator such as a cannula, hollow tube or hollow drill bit and an inner penetrator such as a stylet or trocar. Various types of stylets and/or trocars may be disposed within an outer penetrator. For some applications outer penetrator or cannula 110c may be described as a generally elongated tube sized to receive inner penetrator or stylet 120c therein. Portions of inner penetrator 120c may be disposed within longitudinal passageway 118 extending through outer penetrator 110c. The outside diameter of inner penetrator 120c and the inside diameter of longitudinal passageway 118 may be selected such that inner penetrator 120c may be slidably disposed within outer penetrator 110c.

Metallic disc 170 may be disposed within opening 186 for use in releasably attaching connector 150c with a magnet disposed on a driveshaft (e.g., driveshaft 222 of driver 200 shown in FIG. 2), such as, for example, on end of the driveshaft (e.g., end 224 of driveshaft 222). End 122 of inner penetrator 120c may be spaced from metallic disc 170 with insulating or electrically nonconductive material disposed therebetween. In other embodiments, disc 170 can be magnetic or magnetized to be attracted to a driveshaft (e.g., 222) that is metallic). Tip 111c of outer penetrator 110c and/or tip 121 of inner penetrator 120c may be operable to penetrate bone and associated bone marrow. The configuration of tips 111c and/or 121 may be selected to penetrate a bone or other body cavities with minimal trauma. First end or tip 121 of inner penetrator 120c may be trapezoid shaped and may include one or more cutting surfaces. In one embodiment outer penetrator 110c and inner penetrator 120c may be ground together as one unit during an associated manufacturing process. Providing a matching fit allows respective tips 111c and 121 to act as a single drilling unit which facilitates insertion and minimizes damage as portions of penetrator assembly 100c are inserted into a bone and associated bone marrow. Outer penetrator 110c and/or inner penetrator 120c may be formed from stainless steel, titanium or other materials of suitable strength and durability to penetrate bone.

Hub 140c may be used to stabilize penetrator assembly 100c during insertion of an associated penetrator into a patient's skin, soft tissue and adjacent bone at a selected insertion site. Second end 142 of hub 140c may be operable for releasable engagement or attachment with associated connector 150c. First end 141 of hub 140c may have a size and configuration compatible with an associated insertion site for outer penetrator 110c. Connector 150c and attached inner penetrator 120c may be releasably engaged with each other by Luer type fittings, threaded connections or other suitable fittings formed on second end 142 of hub 140c. Outer penetrator 110c extends from first end 141 of hub 140c. For some applications connector 150c may be described as a generally cylindrical tube defined in part by second end 152 and first end 151. The exterior of connector 150c may include an enlarged tapered portion adjacent to end 181. A plurality of longitudinal ridges 190 may be formed on the exterior of connector 150c to allow an operator to grasp associated penetrator assembly 100c during attachment with a driveshaft. Longitudinal ridges 190 also allow connector 150c to be grasped for disengagement from hub 140c when outer penetrator 110c has been inserted into a bone and associated bone marrow.

First end 151 of connector 150c may include opening 185 sized to receive second end 142 of hub 140c therein. Threads 158 may be formed in an opening adjacent to first end 151 of connector 150c, as shown. Threaded fitting 158 may be used in releasably attaching connector 150c with threaded fitting 148 adjacent to second end 142 of hub 140c. Second end 142 of hub 140c may include a threaded connector 148 or other suitable fittings formed on the exterior thereof. Second end 142 may have a generally cylindrical pin type configuration compatible with releasably engaging second end or box end 182 of connector 150c. For some applications end 141 of hub 140c may have the general configuration of a flange. Angular slot or groove 188 sized to receive one end of protective cover or needle cap 234 may be formed in end 202. Slot or groove 204 may be used to releasable engage a needle cover (not expressly shown) with penetrator assembly 100c.

For some applications a penetrator assembly may include only a single, hollow penetrator. For other applications a penetrator assembly may include an outer penetrator such as a cannula, hollow needle or hollow drill bit and an inner penetrator such as a stylet, trocar or other removable device disposed within the outer penetrator. Penetrator 110c is one example of a single, hollow penetrator or cannula. The size of a penetrator may vary depending upon the intended application for the associated penetrator assembly. Penetrators may be relatively small for pediatric patients, medium size for adults and large for oversize adults. By way of example, a penetrator may range in length from five (5) mm to thirty (30) mm. The diameter of a penetrator may range from eighteen (18) gauge to ten (10) gauge. The length and diameter of the penetrator used in a particular application may depend on the size of a bone to which the apparatus may be applied. Penetrators may be provided in a wide variety of configurations depending upon intended clinical purposes for insertion of the associated penetrator. For example, there may be one configuration for administering drugs and/or fluids to a patient's bone marrow and an alternative configuration for sampling bone marrow and/or blood from a patient.

For some applications connector 150c may be described as having a generally cylindrical configuration defined in part by second end 152 and first end 151. Exterior portions of connector 150c may include an enlarged tapered portion adjacent to end 181. A plurality of longitudinal ridges 190 may be formed on the exterior of connector 150c to allow an operator to grasp associated penetrator assembly 100c during attachment with a driveshaft. Longitudinal ridges 190 also allow connector 150c to be grasped for disengagement from hub 140c when outer penetrator 110c has been inserted into a bone and associated bone marrow. Second end 152 of connector of 150c may included opening 186 sized to receive portions driveshaft 52 therein. A plurality of webs 136 may extend radially outward from connector receptacle 186. Webs 136 cooperate with each other to form a plurality of openings 138 adjacent to second end 152. Opening 186 and openings 138 cooperate with each other to form portions of a connector receptacle operable to receive respective portions of a connector (not expressly shown) therein.

Figure 2:
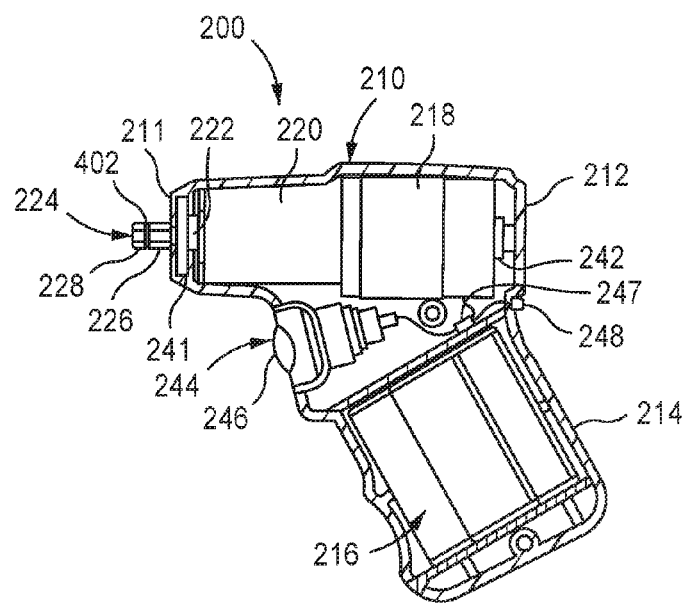
FIG. 2 depicts a cross-sectional side view of one embodiment of the present drivers.

FIG. 2 depicts a cross-sectional view of one embodiment of a driver that can be used with embodiments of the present drivers, coupler assemblies, and kits. In the embodiment shown, powered driver 200 may be used to insert one of the present intraosseous devices into a bone and associated bone marrow. Powered driver 200 may include housing 210 having a general configuration similar to a small pistol defined in part by handle 214. Various components associated with powered driver 200 may be disposed within housing 210 (e.g., handle 214). For example a power source such as battery pack 216 may be disposed within handle 214. Housing 210 may be formed from relatively strong, heavy duty polymeric materials such as polycarbonate or other satisfactory materials. For some applications housing 210 may be formed in two halves (not expressly shown) which may be joined together with a fluid tight seal to protect various components of powered driver 200 disposed therein.

Motor 218 and gear assembly 220 may be disposed within portions of housing 210 adjacent to handle 214. Motor 218 and gear assembly 220 may be generally aligned with each other. Motor 218 may be rotatably engaged with one end of gear assembly 220. Driveshaft 222 may be rotatably engaged with and extend from another end of gear assembly 220 opposite from motor 218. For some applications both motor 218 and gear assembly 220 may have generally cylindrical configurations. Distal end or first end 211 of housing 210 may include an opening with portions of driveshaft 222 extending through the opening, as shown. For some applications, end 224 or the portion of driveshaft 222 extending from first end 211 of housing 210 may have a generally hexagonal cross section with surfaces 226 disposed thereon. Receptacle 263 disposed in second end 252 of coupler assembly 250 may have a matching generally hexagonal cross section, as shown in FIGS. 6A-6C of International Patent Application No. PCT/US2007/078207 (published as WO 2008/033874).

Surfaces 226 may extend generally parallel with each other and parallel with respect to a longitudinal axis or rotational axis of driveshaft 222. One or more tapered surfaces 228 may also be formed on end 224 to assist with releasably engaging powered driver 200 with coupler assembly 250. Embodiments of powered driver 200 include speed reduction ratios, for example, of between 60:1 and 80:1, resulting in driveshaft RPMs that are reduced relative to motor RPMs. Coupler assemblies having corresponding openings or receptacles may be releasably engaged with end 224 extending from first end 211 of powered driver 200. For example, end 224 extending from first end 211 of housing 210 may be releasably engaged with receptacle 264 disposed proximate second end 252 of coupler assembly 250, as shown in FIGS. 6A-6B.

For some applications thrust bearing 241 may be disposed between first end or distal end 211 of housing 210 and adjacent portions of gear assembly 220. Thrust bearing 242 may be disposed between second end or proximal end 212 of housing 210 and adjacent portions of motor 218. Thrust bearings 241 and 242 may limit longitudinal movement of motor 218, gear assembly 220 and driveshaft 222 within associated portions of housing 210. Trigger assembly 244 may also be disposed within housing 210 proximate handle 214. Trigger assembly 244 may include trigger or contact switch 246. Motor 218 may be energized and deenergized by alternately depressing and releasing trigger 246. Electrical circuit board 247 may also be disposed within housing 210. Electrical circuit board 247 may be electrically coupled with trigger assembly 244, motor 218, power supply 216 and indicator light 248. For some applications indicator light 248 may be a light emitting diode (LED) or a small more conventional light bulb. For some applications indicator light 248 may be activated when ninety percent (90%) of electrical storage capacity of battery pack 216 has been used. The configuration and dimensions of an intraosseous device formed in accordance with teachings of the present disclosure may vary depending upon respective intended applications for each intraosseous device. For example the length of a biopsy needle formed in accordance with teachings of the present disclosure may vary from approximately five (5) millimeters to thirty (30) millimeters.

Couplers and coupler assemblies incorporating teachings of the present disclosure may function as "quick release mechanisms" operable to engage and disengage an IO device from a powered driver (e.g., a driver disposed within a flexible containment bag or sterile sleeve). In applications involving a flexible containment bag or sterile sleeve, such coupler assemblies may allow rotation of an IO device (e.g., biopsy needle or needle set) without damage to the flexible containment bag or sterile sleeve, and one end of the coupler assembly may be operable to form a fluid seal or fluid barrier with adjacent portions of the containment bag or sterile sleeve. A coupler assembly incorporating teachings of the present disclosure may also be described as a port assembly attached to a containment bag. Such port assemblies may allow easy engagement or disengagement of a powered driver from an IO device and at the same time allow the powered driver to "power in and power out" an IO device from an insertion site. FIGS. 3A-35C depict various embodiments of the present couplers in conjunction with drivers and/or IO devices; because the drivers and/or IO devices are similar in many respects to driver 200 of FIG. 2 and IO devices 100a-100c of FIGS. 1A-1F, the differences in the drivers and/or IO devices are primarily described below.

Figure 3A:
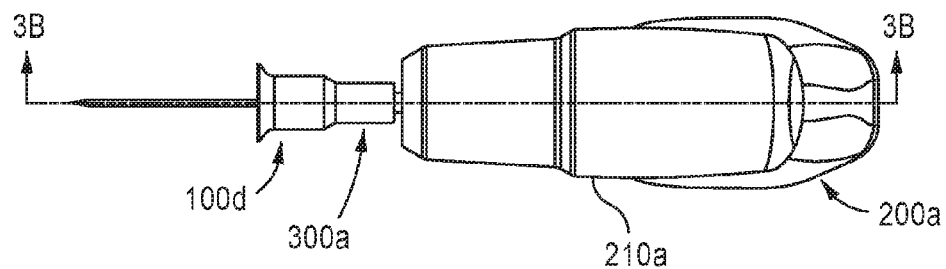
FIGS. 3A-3C depict various views of a first embodiment of the present couplers in combination with a powered driver and an IO device.
Figure 3B:
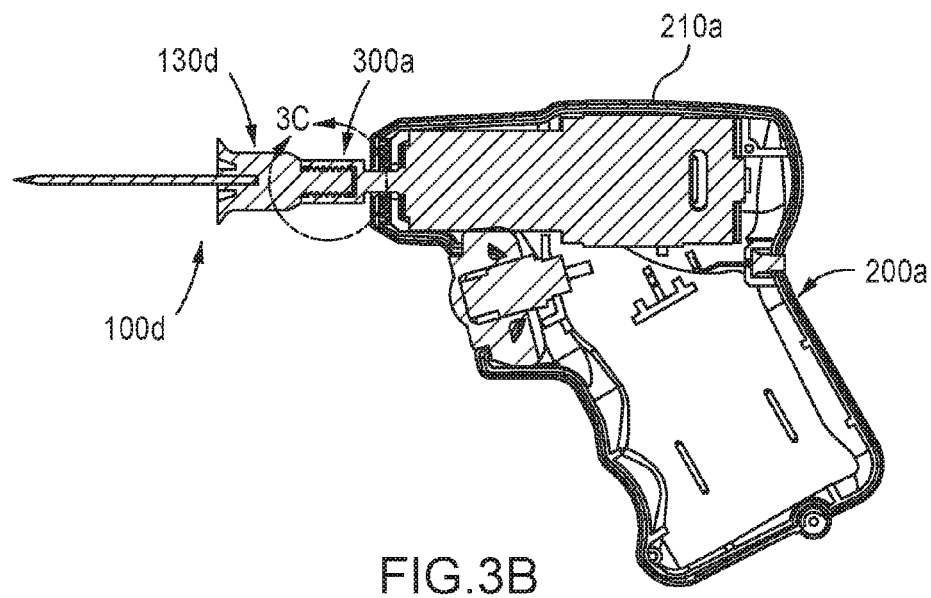
Figure 3C:
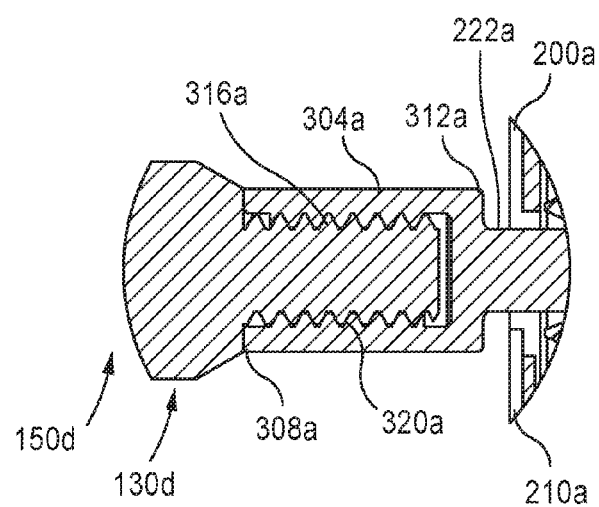

FIGS. 3A-3C depict various views of a first embodiment 300a of the present couplers in combination with a powered driver 200a and an IO device 100d that is configured to provide access to an interior of a bone (e.g., similar in some respects to IO device 100c). In the embodiment shown, coupler 300a comprises a drive hub 304a having a first end 308a and a second end 312a configured to be coupled in fixed relation to a driveshaft 222a (of a driver 200a having a housing 210a) such that at least a portion of the drive hub is disposed outside the housing of the driver. In the embodiment shown, first end 308a of drive hub 304a includes female threads 316a configured to be coupled to an intraosseous (IO) device 100d, as shown. More particularly, in the embodiment shown, hub assembly 130d (and more specifically second hub 150d, in the depicted embodiment) of IO device 100d includes male threads 320a corresponding to female threads 316a. In the embodiment shown, threads 316a (and 320a) are configured to tighten if the driver rotates drive hub 304a and IO device 100d (coupled to the drive hub) in a clockwise direction. In the embodiment shown, drive hub 304a is unitary with driveshaft 222a (drive hub 304a and driveshaft 222a comprise a single piece of material). In other embodiments, drive hub 304a may be coupled to driveshaft 222a in any manner (e.g., welding, threads, press-fit, and/or the like) that permits the function described in this disclosure.

Figure 4A:
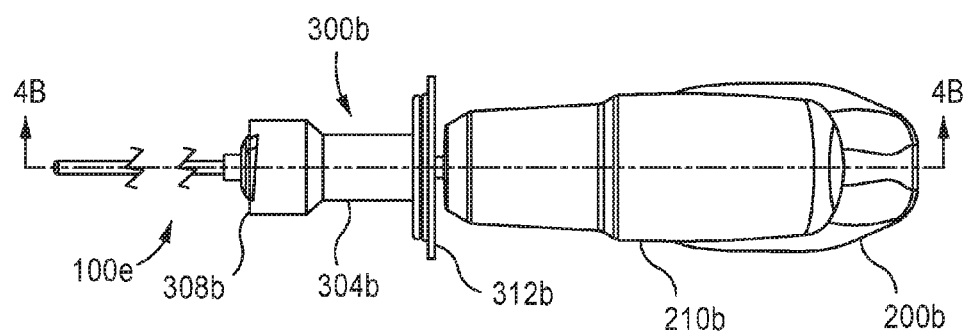
FIGS. 4A-4C depict various views of a second embodiment of the present couplers in combination with a powered driver and an IO device.
Figure 4B:
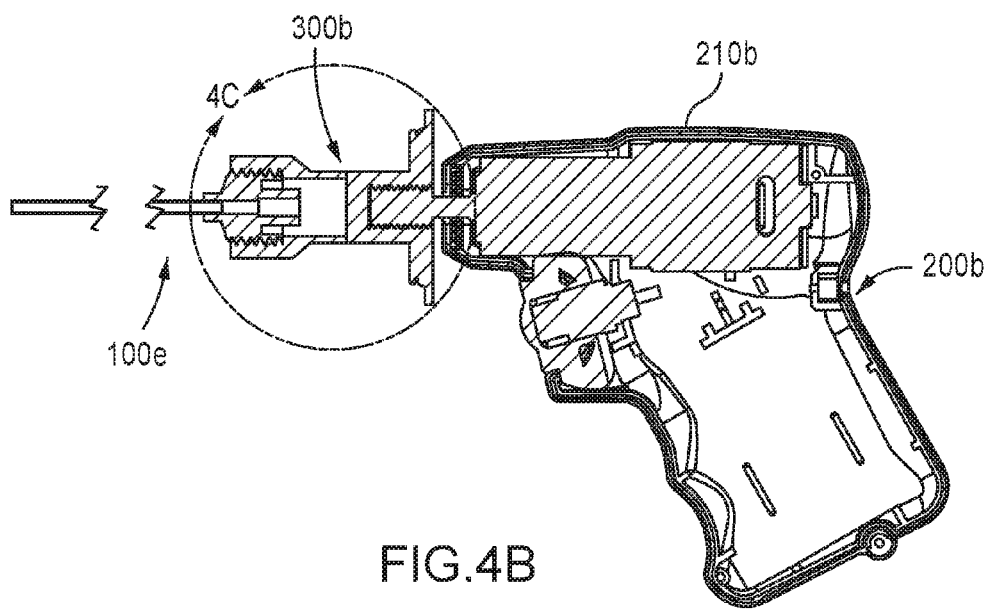
Figure 4C:
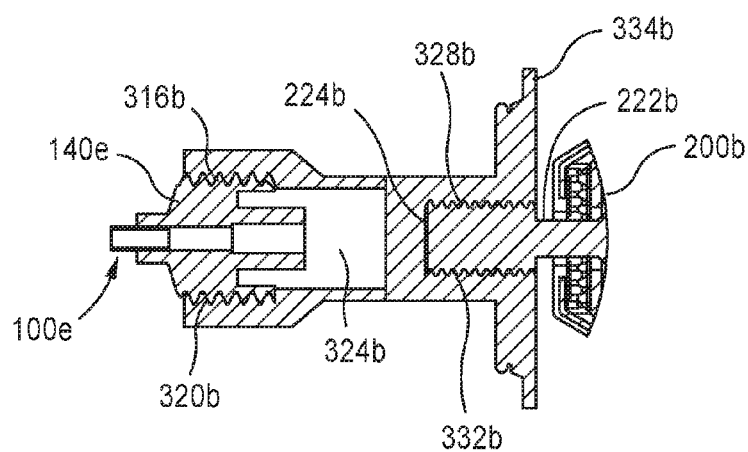
Figure 5A:
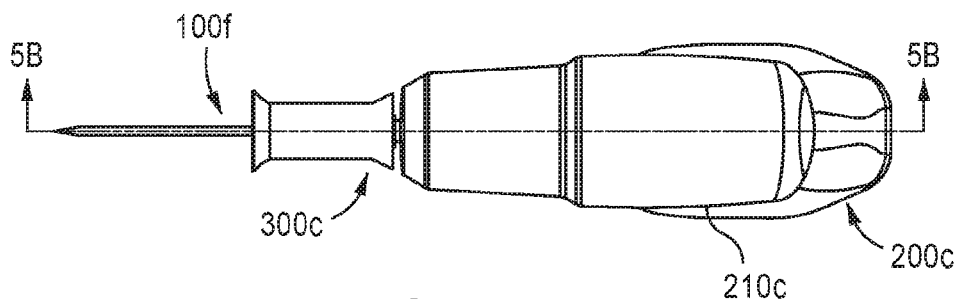
FIGS. 5A-5D depict various views of a third embodiment of the present couplers in combination with a powered driver and an IO device.
Figure 5B:
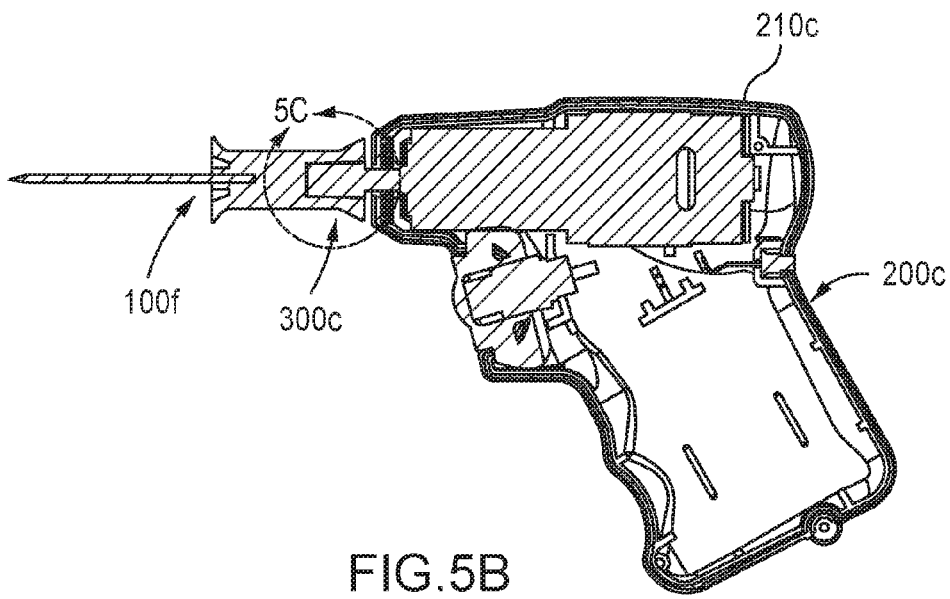
Figures 5C, 5D:
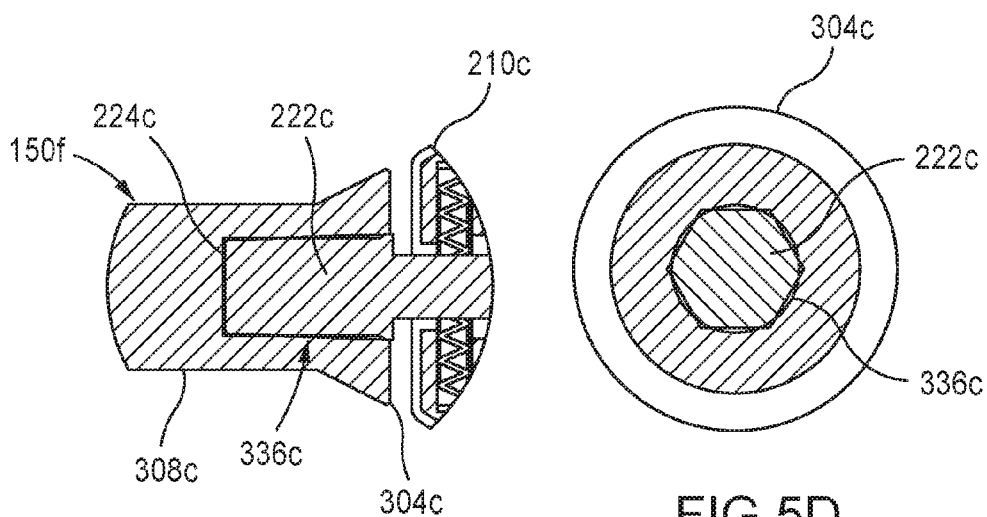

FIGS. 4A-4C depict various views of a second embodiment 300b of the present couplers in combination with a powered driver 200b and an IO device 100e that is configured for obtaining a sample of bone and/or bone marrow (e.g., similar in some respects to IO devices 100a and/or 100b). Coupler 300b is similar in some respects to coupler 300a. In the embodiment shown, coupler 300b comprises a drive hub 304b having a first end 308b and a second end 312b configured to be coupled in fixed relation to a driveshaft 222b (of a driver 200b having a housing 210b) such that at least a portion of the drive hub is disposed outside the housing of the driver. In the embodiment shown, first end 308b of drive hub 304b includes female threads 316b configured to be coupled to an intraosseous (IO) device 100e, as shown. More particularly, in the embodiment shown, hub assembly 130e (and more specifically first hub 140e, in the depicted embodiment) of IO device 100e includes male threads 320b corresponding to female threads 316b. Coupler 300b differs from coupler 300a, for example, in that drive hub 304b includes a recess 324b that is sized to receive a second hub (not shown, but similar to second hub 150a of IO device 100a). In the embodiment shown, threads 316b (and 320b) are configured to tighten if the driver rotates drive hub 304b and IO device 100e (coupled to the drive hub) in a clockwise direction. Coupler 300b further differs from coupler 300a, for example, in that second end 312b of drive hub 304b includes female threads 328a configured to be coupled to driveshaft 222b of driver 200b. In the embodiment shown, driveshaft 222b has a distal end 224b and includes male threads 332b adjacent corresponding to female threads 328b. In the embodiment shown, second end 312b of drive hub 304b comprises a flange 334b extending outwardly relative to an axis of rotation of the drive hub, as shown. Flange 334b may, for example, be used to connect coupler 300b to a containment bag or the like (e.g., as disclosed WO 2008/033874).

FIGS. 5A-5D depict various views of a third embodiment 300c of the present couplers in combination with a powered driver 200c and an IO device 100f that is configured to provide access to an interior of a bone (e.g., similar in some respects to IO device 100c). In the embodiment shown, coupler 300c comprises a drive hub 304c having a first end 308c and a second end 312c including a recess 336c configured to receive driveshaft 222c of driver 200c. In this embodiment, second end 312c is configured such that if driveshaft 222c is inserted into recess 336c, an interference fit between drive hub 304c and driveshaft 222c will resist rotation of the drive hub relative to the driveshaft (and/or resist removal of drive hub 304c from driveshaft 222c). For example, in the embodiment shown, driveshaft 222c is substantially rigid (e.g., comprises a metal such as stainless steel) and has a transverse dimension that is larger than a corresponding transverse dimension of recess 336c such that as driveshaft 222c is inserted into recess 336c, drive hub 304c will deflect slightly and impart a compressive force on driveshaft 222c. Drive hub 304c can comprise, for example, a resilient material such as a resilient polymer, or any other material permitting the described function. In some embodiments, the driveshaft and the recess have dissimilar cross-sectional shapes. For example, in the embodiment shown (FIG. 5D), driveshaft 222c has a hexagonal cross-sectional shape and recess 336c has a circular cross-sectional shape. In other embodiments, the driveshaft and recess can have similar cross-sectional shapes (e.g., driveshaft 222c can have a circular cross-sectional shape. To facilitate insertion of driveshaft 222c into recess 336c, one or both of driveshaft 222c and recess 336c can be tapered (e.g., driveshaft 222c can have a transverse dimension that is relatively smaller at distal end 224c and increases along a portion of driveshaft 222c approaching housing 210c, and/or recess 336c can have a relatively larger transverse dimension (e.g., diameter) at second end 312c that increases along a portion of recess 336c approaching first end 308c). In the embodiment shown, first end 308c is configured to be coupled to IO device 100f (e.g., to resist rotation of the IO device relative to the drive hub). For example, in the embodiment shown, drive hub 304c is unitary with a portion of hub assembly 130f (and more specifically unitary with second hub 150f, in the depicted embodiment).

FIGS. 6A-6E depict various views of a fourth embodiment 300d of the present couplers in combination with a powered driver 200d and an IO device 100g that is configured for obtaining a sample of bone and/or bone marrow (e.g., similar in some respects to IO devices 100a and/or 100b). In the embodiment shown, coupler 300d comprises a drive hub 304d having a first end 308d and a second end 312d including a recess 336d configured to receive driveshaft 222d of driver 200d. In this embodiment, second end 312d is configured such that if driveshaft 222d is inserted into recess 336d, an interference fit between drive hub 304d and driveshaft 222d will resist rotation of the drive hub relative to the driveshaft (and/or resist removal of the drive hub from driveshaft). For example, in the embodiment shown, driveshaft 222d is substantially rigid (e.g., comprises a metal such as stainless steel) and has a transverse dimension that is larger than a corresponding transverse dimension of recess 336d such that as driveshaft 222d is inserted into recess 336d, drive hub 304d will deflect slightly and impart a compressive force on driveshaft 222d. Drive hub 304d can comprise, for example, a resilient material such as a resilient polymer, or any other material permitting the described function. In some embodiments, the driveshaft and the recess have dissimilar cross-sectional shapes. For example, in the embodiment shown (FIG. 6E), driveshaft 222d has a hexagonal cross-sectional shape and recess 336d has a circular cross-sectional shape. In other embodiments, the driveshaft and recess can have similar cross-sectional shapes (e.g., driveshaft 222d can have a circular cross-sectional shape). To facilitate insertion of driveshaft 222d into recess 336d, one or both of driveshaft 222d and recess 336d can be tapered (e.g., driveshaft 222d can have a transverse dimension that is relatively smaller at distal end 224d and increases along a portion of driveshaft 222d approaching housing 210d, and/or recess 336d can have a relatively larger transverse dimension (e.g., diameter) at second end 312d that increases along a portion of recess 336d approaching first end 308d). Further, in this embodiment driveshaft 222d comprises an enlarged cap member 223d that can comprise a resilient material (e.g., a resilient polymer) to further facilitate insertion of driveshaft 222d into recess 336d.

Coupler 300d further differs from coupler 300c, for example, in that first end 308d includes a second recess 340d that is sized to receive a hub (e.g., first hub 140g) of IO device 100g, and first end 308d is configured such that if hub 140g is inserted into recess 340d, an interference fit between drive hub 308d and hub 140g will resist rotation of IO device 100g relative to the drive hub 304d. As described above for drive hub 304d and driveshaft 222, drive hub 304d can comprise, for example, a resilient material such as a resilient polymer, or any other material permitting the described function. In some embodiments, hub 140g and recess 340d have dissimilar cross-sectional shapes. For example, in the embodiment shown (FIG. 6D), hub 140g has a hexagonal cross-sectional shape and recess 340d has a circular cross-sectional shape. In other embodiments, the driveshaft and recess can have similar cross-sectional shapes (e.g., hub 140g can have a circular cross-sectional shape). To facilitate insertion of hub 140g into recess 340d, one or both of hub 140g and recess 340d can be tapered (e.g., hub 140g can have a transverse dimension that is relatively smaller at second end 142 and increases along a portion of hub 140g approaching first end 141, and/or recess 340d can have a relatively larger transverse dimension (e.g., diameter) at first end 308d that increases along a portion of recess 340d approaching second end 312d). Coupler 300d further differs from coupler 300c, for example, in that drive hub 304d includes a recess 324d that is sized to receive a second hub (not shown, but similar to second hub 150a of IO device 100a) in combination with first hub 140g of IO device 100g.

Figure 7A:
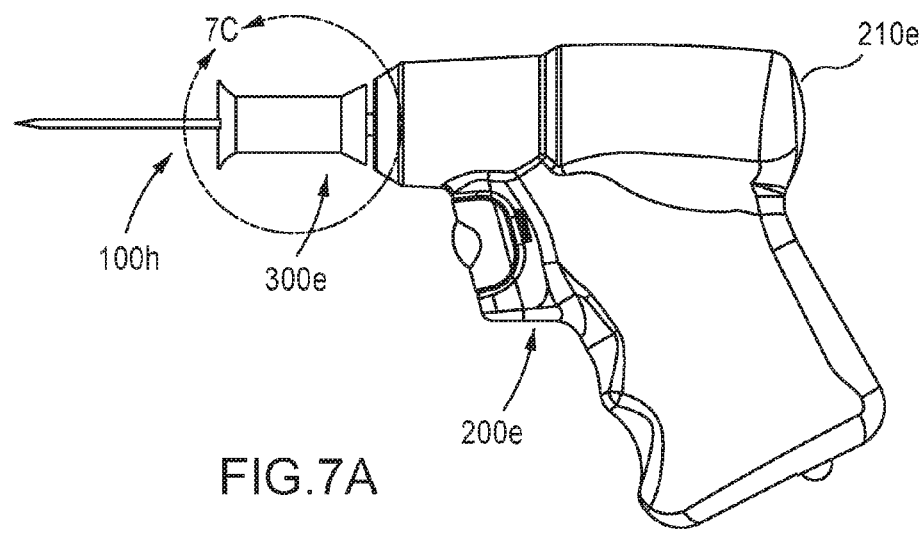
FIGS. 7A-7C depict various views of a fifth embodiment of the present couplers in combination with a powered driver and an IO device.
Figure 7B:
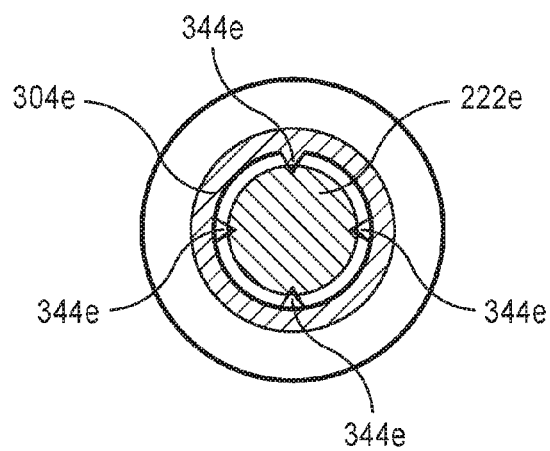
Figure 7C:
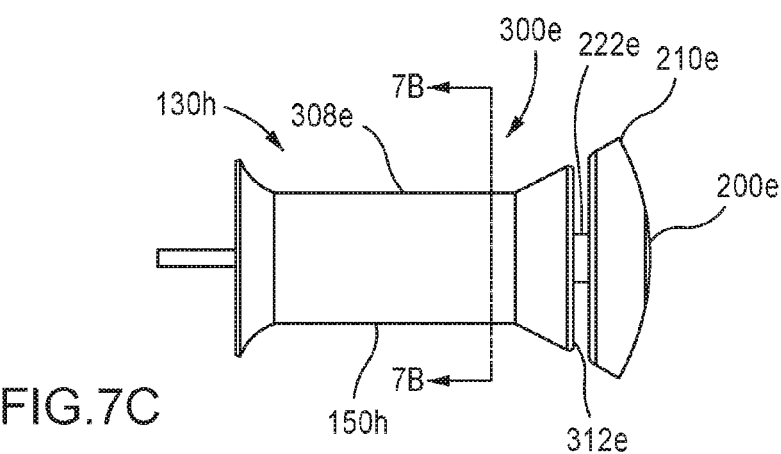

FIGS. 7A-7C depict various views of a fifth embodiment 300e of the present couplers in combination with a powered driver 200e and an IO device 100h that is configured to provide access to an interior of a bone (e.g., similar in some respects to IO device 100c). In the embodiment shown, coupler 300e comprises a drive hub 304e having a first end 308e and a second end 312e including a recess 336e configured to receive driveshaft 222e of driver 200e. In this embodiment, second end 312e is configured such that if driveshaft 222e is inserted into recess 336e, an interference fit between drive hub 304e and driveshaft 222e will resist rotation of the drive hub relative to the driveshaft (and/or resist removal of drive hub 304e from driveshaft 222e). For example, in the embodiment shown, driveshaft 222e is substantially rigid (e.g., comprises a metal such as stainless steel), and drive hub 304e includes a plurality of tabs or ribs 344e (e.g., with a triangular cross-sectional shape, as shown) extending into recess 336e. In this embodiment, tabs 344e are configured to deform if the driveshaft is inserted into the recess. In the embodiment shown, recess 336e has at least one transverse dimension that is larger than a transverse dimension of driveshaft 222e; however, tabs 344e extend inward and a transverse distance between opposing tabs 344e is less than a transverse dimension of driveshaft 222e, such that tabs 344e will deflect and/or compress and impart a compressive force on driveshaft 222e. Drive hub 304e can comprise, for example, a resilient material such as a resilient polymer, or any other material permitting the described function. In the embodiment shown, first end 308e is configured to be coupled to IO device 100h (e.g., to resist rotation of the IO device relative to the drive hub). For example, in the embodiment shown, drive hub 304e is unitary with a portion of hub assembly 130h (e.g., unitary with second hub 150h). While not shown in FIGS. 7A-7C, other embodiments can comprise a second recess in first end 308e with tabs extending into the recess to form an interference fit with a hub of an IO device (e.g., similar to coupler 100d).

Figure 8A:
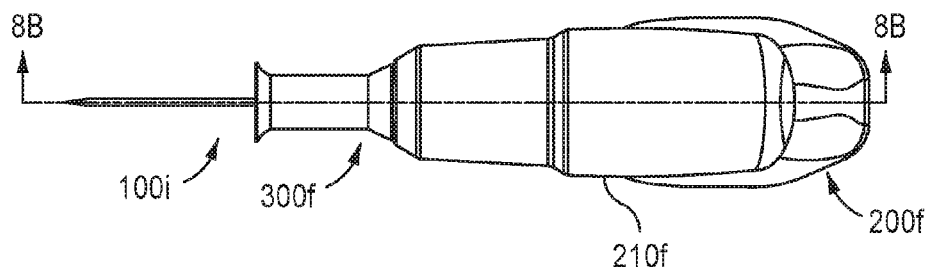
FIGS. 8A-8C depict various views of a sixth embodiment of the present couplers in combination with a powered driver and an IO device.
Figure 8B:
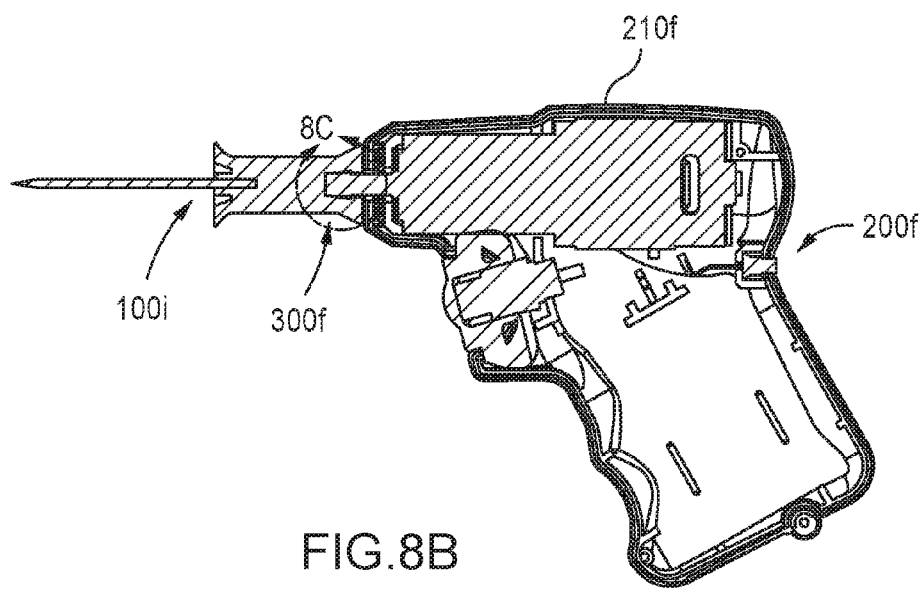
Figure 8C:
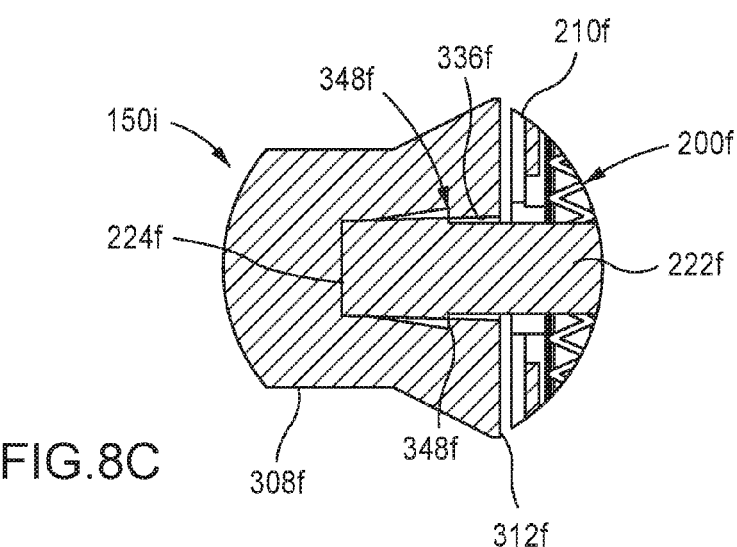

FIGS. 8A-8C depict various views of a sixth embodiment 300f of the present couplers in combination with a powered driver 200f and an IO device 100i that is configured to provide access to an interior of a bone (e.g., similar in some respects to IO device 100c). In the embodiment shown, coupler 300f comprises a drive hub 304f having a first end 308f and a second end 312f including a recess 336f configured to receive driveshaft 222f of driver 200f. In this embodiment, second end 312f is configured such that if driveshaft 222f is inserted into recess 336f, an interference fit between drive hub 304f and driveshaft 222f will resist rotation of the drive hub relative to the driveshaft (and/or resist removal of drive hub 304f from driveshaft 222f). For example, in the embodiment shown, driveshaft 222f comprises one or more barbs 348f (e.g., an annular barb surrounding the perimeter of the driveshaft, or one or more discrete barbs disposed around the driveshaft) with a transverse dimension between outermost portions of barb(s) 348f that is larger than a corresponding transverse dimension of recess 336f such that as driveshaft 222f is inserted into recess 336f, drive hub 304f will deflect slightly and impart a compressive force on barb(s) 348f. In the embodiment shown, driveshaft 222f is substantially rigid (e.g., comprises a metal such as stainless steel). Drive hub 304f can comprise, for example, a resilient material such as a resilient polymer, or any other material permitting the described function. In some embodiments, the driveshaft and the recess have similar cross-sectional shapes. For example, in the embodiment shown (FIG. 5D), driveshaft 222f has an annular barb 348f with a circular cross-sectional shape and recess 336f has a circular cross-sectional shape. In other embodiments, the driveshaft and recess can have dissimilar cross-sectional shapes (e.g., driveshaft 222f can have a plurality of discrete barbs) and recess 336f can have a circular cross-sectional shape. To facilitate insertion of driveshaft 222f into recess 336f, one or both of driveshaft 222f and recess 336f can be tapered (e.g., driveshaft 222f can have a transverse dimension that is relatively smaller at distal end 224f and increases along a portion of driveshaft 222f approaching housing 210f, as shown, and/or recess 336f can have a relatively larger transverse dimension (e.g., diameter) at second end 312f that increases along a portion of recess 336f approaching first end 308f). In the embodiment shown, first end 308f is configured to be coupled to IO device 100i (e.g., to resist rotation of the IO device relative to the drive hub). For example, in the embodiment shown, drive hub 304f is unitary with a portion of hub assembly 130i (e.g., unitary with second hub 150i).

Figure 9A:
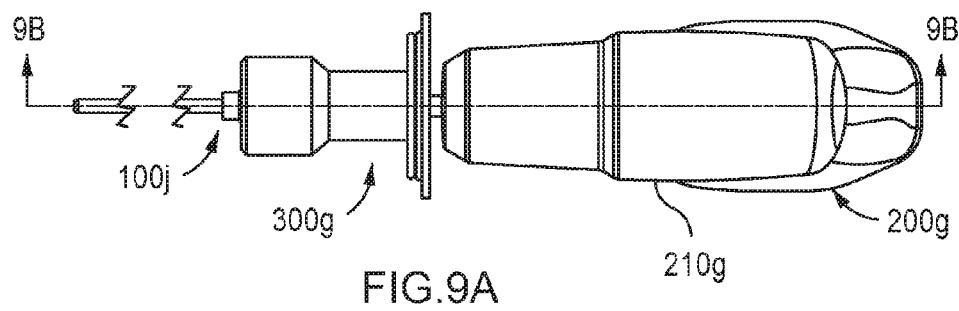
FIGS. 9A-9C depict various views of a seventh embodiment of the present couplers in combination with a powered driver and an IO device.
Figure 9B:
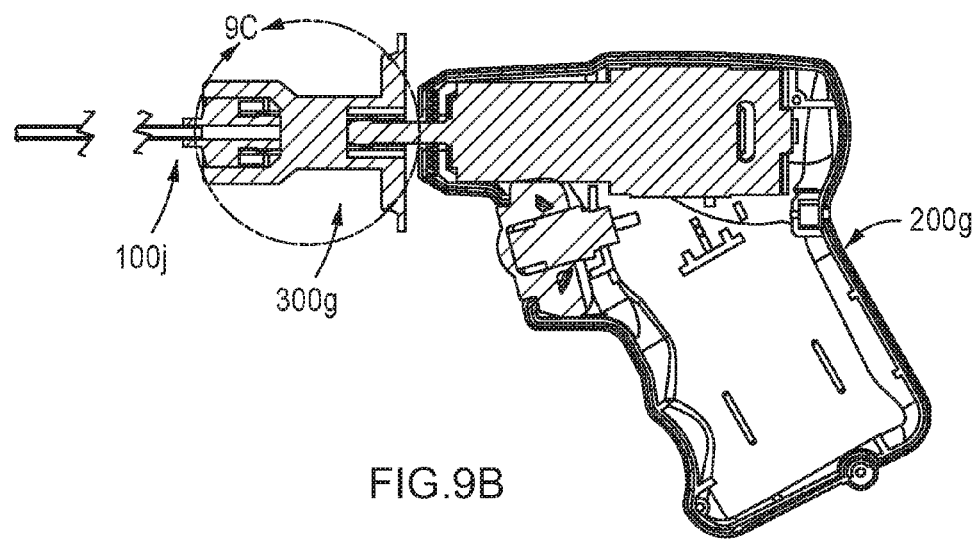
Figure 9C:
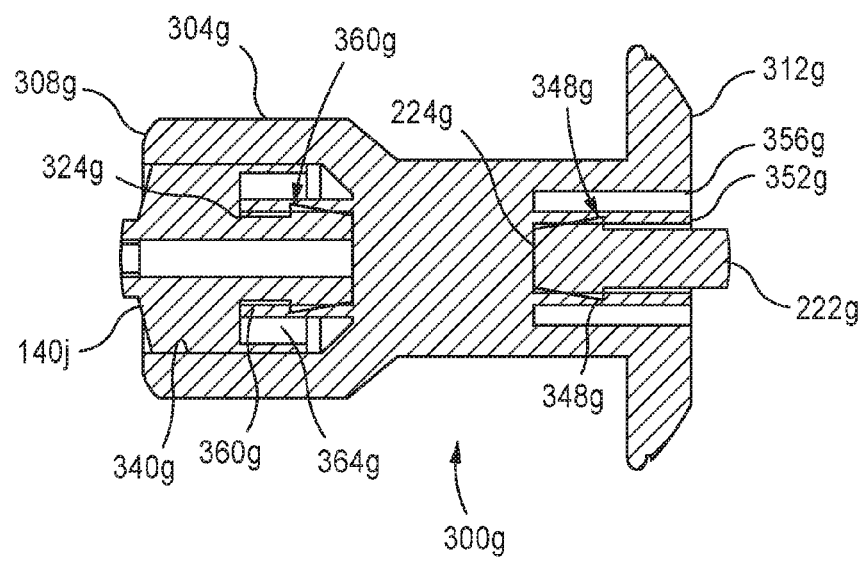
Figure 11A:
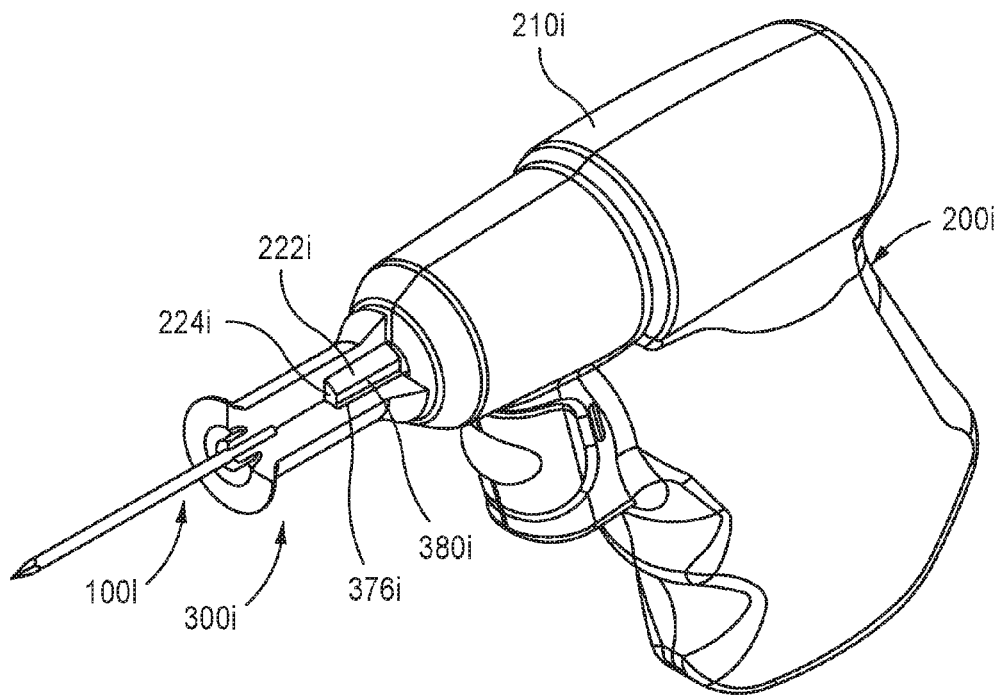
FIGS. 11A-11D depict various views of a ninth embodiment of the present couplers in combination with a powered driver and an IO device.
Figure 11B:
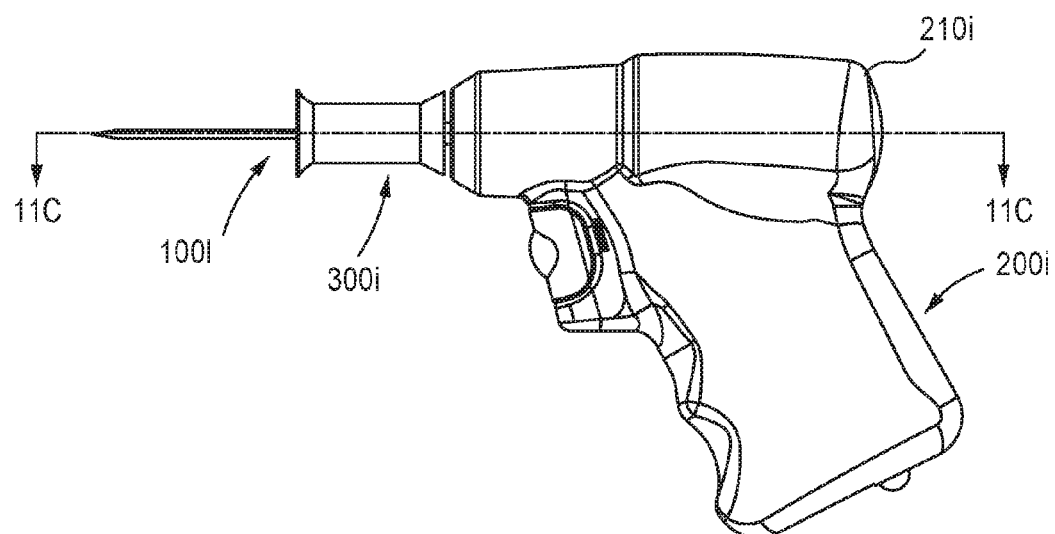
Figure 11C:
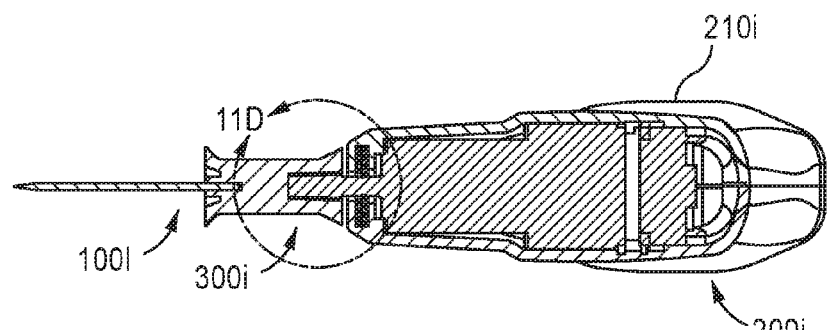
Figure 11D:
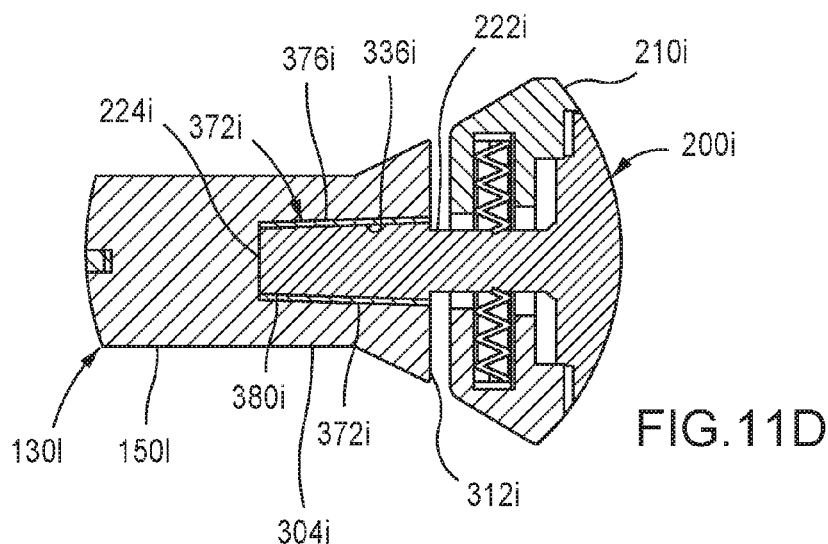
Figure 12A:
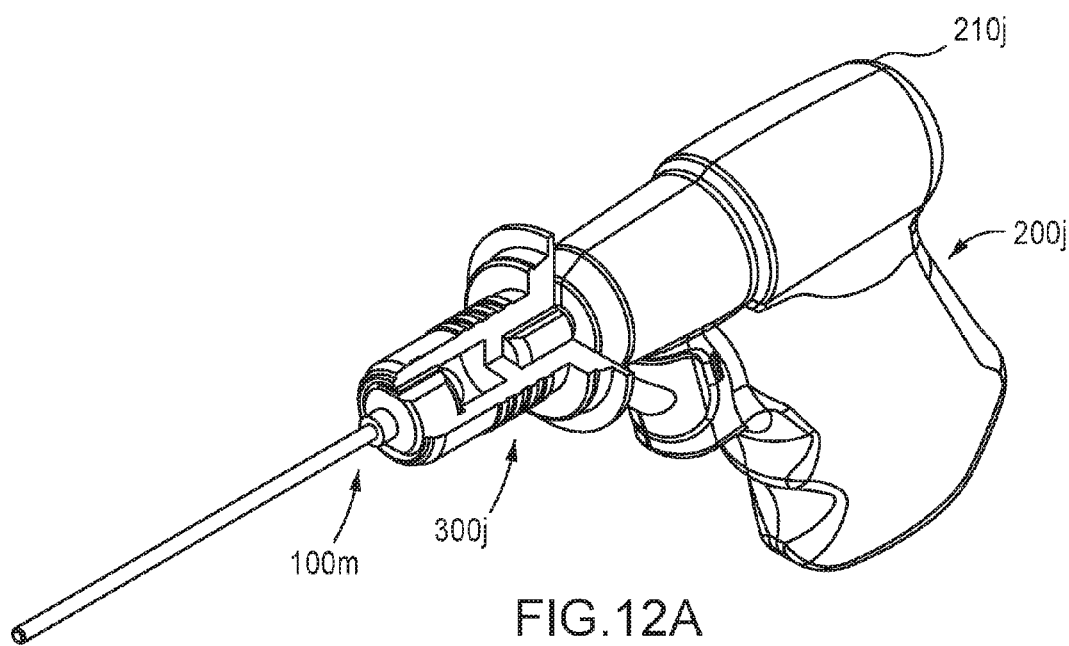
FIGS. 12A-12D depict various views of a tenth embodiment of the present couplers in combination with a powered driver and an IO device.
Figure 12B:
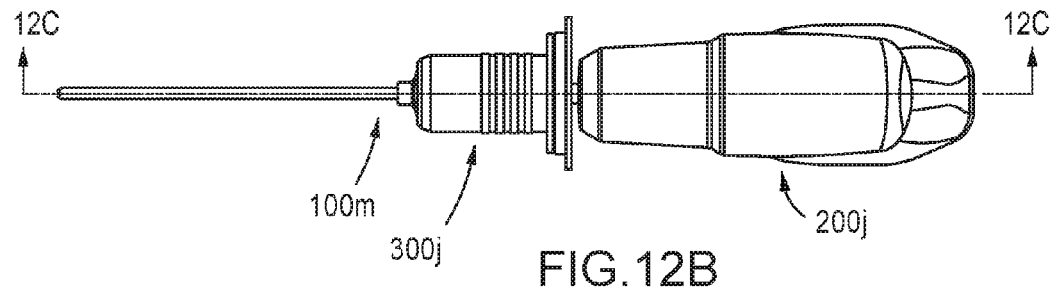
Figure 12C:
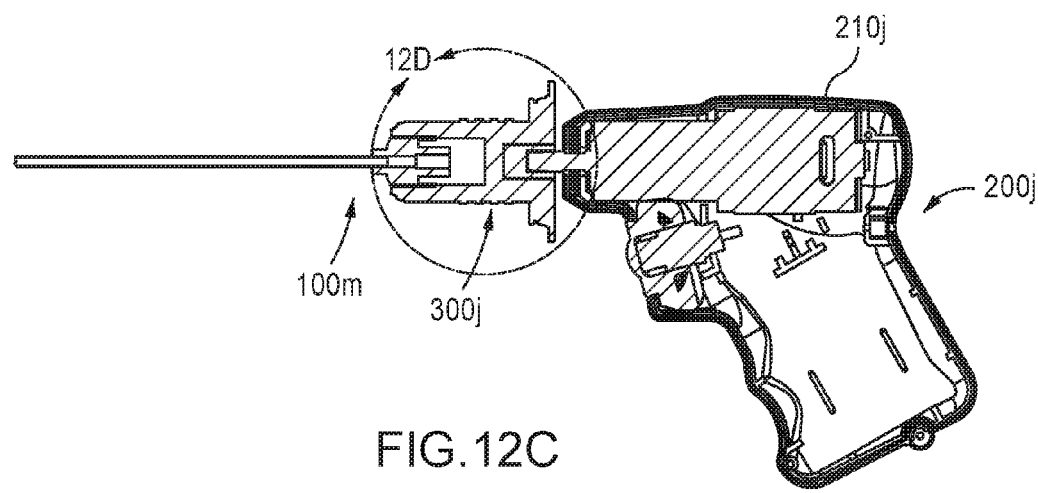
Figure 12D:
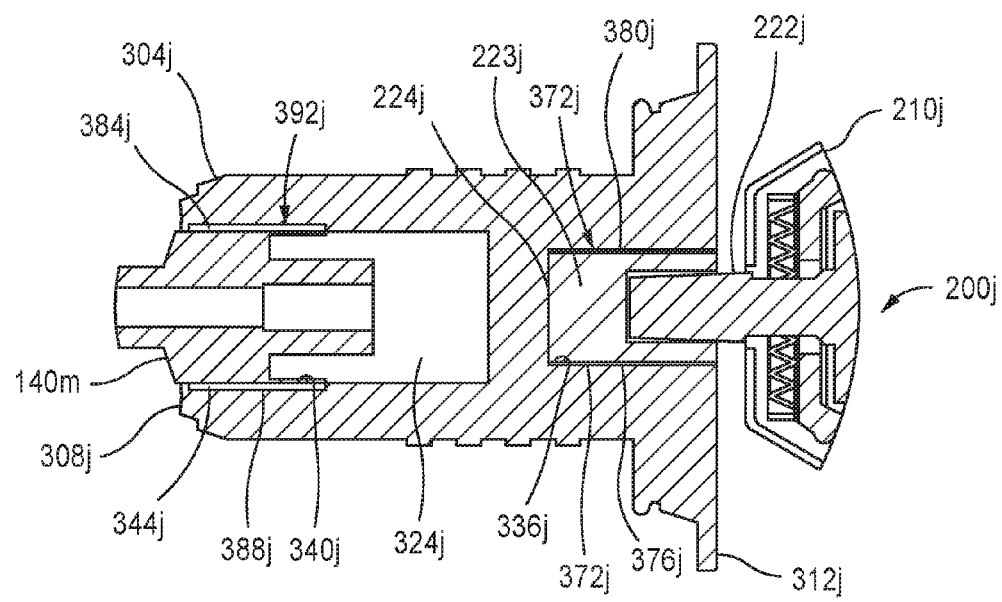

FIGS. 9A-9C depict various views of a seventh embodiment 300g of the present couplers in combination with a powered driver 200g and an IO device 100j that is configured for obtaining a sample of bone and/or bone marrow (e.g., similar in some respects to IO devices 100a and/or 100b). In the embodiment shown, coupler 300g comprises a drive hub 304f having a first end 308f and a second end 312f including a recess 336f configured to receive driveshaft 222g of driver 200g. In this embodiment, second end 312g is configured such that if driveshaft 222g is inserted into recess 336g, an interference fit between drive hub 304g and driveshaft 222g will resist rotation of the drive hub relative to the driveshaft (and/or resist removal of the drive hub from driveshaft). For example, in the embodiment shown, driveshaft 222g comprises one or more barbs 348g (e.g., an annular barb surrounding the perimeter of the driveshaft, or one or more discrete barbs disposed around the driveshaft) with a transverse dimension between outermost portions of barb(s) 348g that is larger than a corresponding transverse dimension of recess 336g such that as driveshaft 222g is inserted into recess 336g, drive hub 304g will deflect slightly and impart a compressive force on barb(s) 348g. In the embodiment shown, driveshaft 222g is substantially rigid (e.g., comprises a metal such as stainless steel). Drive hub 304g can comprise, for example, a resilient material such as a resilient polymer, or any other material permitting the described function. In some embodiments, the driveshaft and the recess have similar cross-sectional shapes. For example, in the embodiment shown (FIG. 5D), driveshaft 222g has an annular barb 348g with a circular cross-sectional shape and recess 336g has a circular cross-sectional shape. In other embodiments, the driveshaft and recess can have dissimilar cross-sectional shapes (e.g., driveshaft 222g can have a plurality of discrete barbs) and recess 336g can have a circular cross-sectional shape. To facilitate insertion of driveshaft 222g into recess 336g, one or both of driveshaft 222g and recess 336g can be tapered (e.g., driveshaft 222g can have a transverse dimension that is relatively smaller at distal end 224g and increases along a portion of driveshaft 222g approaching housing 210g, as shown, and/or recess 336g can have a relatively larger transverse dimension (e.g., diameter) at second end 312g that increases along a portion of recess 336g approaching first end 308g).

Drive hub 304g differs from drive hub 304f, for example, in that recess 336g is defined by a cylindrical wall 352g that is, in turn, at least partially (e.g., up to entirely, as shown) surrounded by a second (e.g., annular) recess 356g that permits wall 352g to flex to facilitate insertion of driveshaft. Drive hub 304g further differs from drive hub 304f, for example, in that first end 308g includes a second recess 340g that is sized to receive a hub (e.g., first hub 140j) of IO device 100g, and first end 308g is configured such that if hub 140j is inserted into recess 340g, an interference fit between drive hub 308g and hub 140j will resist rotation of IO device 100j relative to drive hub 304g. As described above, drive hub 304g can comprise, for example, a resilient material such as a resilient polymer, or any other material permitting the described function. In some embodiments, hub 140j and recess 340g have dissimilar cross-sectional shapes. For example, in the embodiment shown, hub 140j has a hexagonal cross-sectional shape and recess 340g has a circular cross-sectional shape. In other embodiments, the driveshaft and recess can have similar cross-sectional shapes (e.g., hub 140j can have a circular cross-sectional shape). To facilitate insertion of hub 140j into recess 340g, one or both of hub 140j and recess 340g can be tapered (e.g., hub 140j can have a transverse dimension that is relatively smaller at second end 142 and increases along a portion of hub 140j approaching first end 141, and/or recess 340g can have a relatively larger transverse dimension (e.g., diameter) at first end 308g that increases along a portion of recess 340g approaching second end 312g). In the embodiment shown, drive hub 304g also includes a recess 324g configured to receive a portion of hub 140j (e.g., a hose fitting with an annular barb, as shown; or Luer-lock fitting threads 148 as in hub 140a). In other embodiments, recess 324g can be sized to receive a second hub (not shown but similar, for example, to second hub 150*a*). In the embodiment shown, recess 324*g* is defined by a cylindrical wall 360*g* that is, in turn, at least partially (e.g., up to entirely, as shown) surrounded by a second (e.g., annular) recess 364*g* that permits wall 360*g* to flex to facilitate insertion of driveshaft.

FIGS. 10A-10D depict various views of an eighth embodiment 300*h* of the present couplers in combination with a powered driver 200*h* and an IO device 100*k* that is configured to provide access to an interior of a bone (e.g., similar in some respects to IO device 100*c*). In the embodiment shown, coupler 300*h* comprises a drive hub 304*h* having a first end 308*h* and a second end 312*h* including a recess 336*h* configured to receive driveshaft 222*h* of driver 200*h*. In this embodiment, second end 312*h* is configured such that if driveshaft 222*h* is inserted into recess 336*h*, an interference fit between drive hub 304*h* and driveshaft 222*h* will resist rotation of the drive hub relative to the driveshaft (and/or resist removal of drive hub 304*h* from driveshaft 222*h*). For example, in the embodiment shown, driveshaft 222*h* is substantially rigid (e.g., comprises a metal such as stainless steel), and drive hub 304*h* includes a plurality of tabs or ribs 344*h* (e.g., with a triangular cross-sectional shape, as shown) extending into recess 336*h*. In this embodiment, tabs 344*e* are configured to deform if the driveshaft is inserted into the recess. In the embodiment shown, recess 336*h* has at least one transverse dimension that is larger than a transverse dimension of driveshaft 222*h*; however, tabs 344*h* extend inward and a transverse distance between opposing tabs 344*h* is less than a transverse dimension of driveshaft 222*h*, such that tabs 344*h* will deflect and/or compress and impart a compressive force on driveshaft 222*h*. Drive hub 304*h* can comprise, for example, a resilient material such as a resilient polymer, or any other material permitting the described function. In the embodiment shown, first end 308*h* is configured to be coupled to IO device 100*k* (e.g., to resist rotation of the device relative to the drive hub). For example, in the embodiment shown, drive hub 304*h* is unitary with a portion of hub assembly 130*k* (e.g., unitary with second hub 150*k*).

Coupler 300*h* differs from coupler 300*e*, for example, in the drive hub 304*h* defines a recess 336*h* that has a depth that is at least 50% greater (e.g., 100% greater) than the length of driveshaft 222*h* that is received in recess 336*h*, resulting in added length of sidewall 352*h* to increase flexibility of sidewall 352*h* and thereby facilitate insertion of driveshaft 222*h* into recess 352*h*. Driveshaft 222*h* differs from driveshaft 222*e*, for example, in that driveshaft 222*h* (e.g., distal end 224*h*) comprises one or more (e.g., a plurality of, as shown) projections 368*h* extending outward relative to an axis of rotation of the driveshaft. In the embodiment shown, projections 368*h* are configured to be aligned with tabs 344*h*, as shown, to deform tabs 344*h* to create the interference fit between the driveshaft and the drive hub. In the embodiment shown, recess 336*h* has a circular cross-sectional shape. However, in other embodiments, recess 336*h* has a cross-sectional shape that is similar to the cross-sectional shape of driveshaft 222*h* (having a circular central portion and one or more peripheral portions (e.g., corresponding to projections 368*h*) extending outwardly from the circular central portion; and, in such embodiments, tabs 344*h* can each extend into the peripheral portion(s) of the recess). While not shown in FIGS. 10A-10D, other embodiments can comprise a second recess in first end 308*h* with tabs extending into the recess to form an interference fit with a hub of an IO device (e.g., similar to coupler 100*d*).

FIGS. 11A-11D depict various views of a ninth embodiment 300*i* of the present couplers in combination with a powered driver 200*i* and an IO device 1001 that is configured to provide access to an interior of a bone (e.g., similar in some respects to IO device 100*c*). In the embodiment shown, coupler 300*i* comprises a drive hub 304*i* having a first end 308*i* and a second end 312*i* including a recess 336*i* configured to receive driveshaft 222*i* of driver 200*i*. In the embodiment shown, coupler 300*i* further comprises an adhesive 372*i* disposed in the recess and configured to adhere to driveshaft 222*i* if driveshaft 222*i* is inserted into recess 336*i* (e.g., to resist (e.g., interfere with) removal of driveshaft 222*i* from recess 336*i*). In the embodiment shown, recess 336*i* has a cross-sectional shape corresponding to the cross-sectional shape of driveshaft 222*i* such that if the driveshaft is inserted into the second recess, the drive hub will resist rotating relative to the driveshaft. For example, in the embodiment shown, recess 336*i* and driveshaft 222*i* each has a cross-sectional shape of a circle with a portion removed to result in two opposing flat sides 376*i* and 380*i*, respectively. Adhesive 372*i* can comprise a double-sided tape and/or a liquid or gel adhesive disposed in the recess (e.g., at sides 376*i* and/or at the end of distal end of recess 336*i* (farthest from second end 312*i*)). In other embodiments, the driveshaft and recess can have dissimilar cross-sectional shapes (e.g., recess 336*i* can have a circular cross-sectional shape). To facilitate insertion of driveshaft 222*i* into recess 336*i*, one or both of driveshaft 222*i* and recess 336*i* can be tapered (e.g., driveshaft 222*i* can have a transverse dimension that is relatively smaller at distal end 224*i* and increases along a portion of driveshaft 222*i* approaching housing 210*i*, and/or recess 336*i* can have a relatively larger transverse dimension (e.g., diameter) at second end 312*i* that increases along a portion of recess 336*i* approaching first end 308*i*). In the embodiment shown, first end 308*i* is configured to be coupled to IO device 1001 (e.g., to resist rotation of the IO device relative to the drive hub). For example, in the embodiment shown, drive hub 304*i* is unitary with a portion of hub assembly 1301 (e.g., unitary with second hub 1501).

FIGS. 12A-12D depict various views of a tenth embodiment 300*j* of the present couplers in combination with a powered driver 200*j* and an IO device 100*m* that is configured for obtaining a sample of bone and/or bone marrow (e.g., similar in some respects to IO devices 100*a* and/or 100*b*). In the embodiment shown, coupler 300*j* comprises a drive hub 304*j* having a first end 308*j* and a second end 312*j* including a recess 336*j* configured to receive driveshaft 222*j* of driver 200*j*. In the embodiment shown, coupler 300*j* further comprises an adhesive 372*j* disposed in the recess and configured to adhere to driveshaft 222*j* if driveshaft 222*j* is inserted into recess 336*j* (e.g., to resist removal of driveshaft 222*j* from recess 336*j*). In the embodiment shown, recess 336*j* has a cross-sectional shape corresponding to the cross-sectional shape of driveshaft 222*j* such that if the driveshaft is inserted into the second recess, the drive hub will resist rotating relative to the driveshaft. For example, in the embodiment shown, recess 336*j* and driveshaft 222*j* each has a cross-sectional shape of a circle with a portion removed to result in two opposing flat sides 376*j* and 380*j*, respectively. Further, in this embodiment driveshaft 222*d* comprises an enlarged cap member 223*j* (on which flats 380*j* are disposed) that can comprise a resilient material (e.g., a resilient polymer) to further facilitate insertion of driveshaft 222*j* into recess 336*j*. Adhesive 372*j* can comprise a double-sided tape and/or a liquid or gel adhesive disposed in the recess (e.g., at sides 376*j* and/or at the end of distal end of recess 336*j* (farthest from second end 312*j*)). In other embodiments, the driveshaft and the corresponding recess can have dissimilar cross-sectional shapes (e.g., recess 336j can have a circular cross-sectional shape). To facilitate insertion of driveshaft 222j into recess 336j, one or both of driveshaft 222j and recess 336j can be tapered (e.g., driveshaft 222j can have a transverse dimension that is relatively smaller at distal end 224j and increases along a portion of driveshaft 222j approaching housing 210j, and/or recess 336j can have a relatively larger transverse dimension (e.g., diameter) at second end 312j that increases along a portion of recess 336j approaching first end 308j).

Drive hub 304j differs from drive hub 304i, for example, in that first end 308j includes a second recess 340j that is sized to receive a hub (e.g., first hub 140m) of IO device 100m. In the embodiment shown, coupler 300j further comprises an adhesive 384j disposed in recess 340j and configured to adhere to hub 140m if hub 140m is inserted into recess 340j (e.g., to resist removal of IO device 100m from recess 340j). In the embodiment shown, recess 340j has a cross-sectional shape corresponding to the cross-sectional shape of hub 140m such that if hub 140m is inserted into the second recess, the drive hub will resist rotating relative to hub 140m. For example, in the embodiment shown, recess 340j and hub 140m each has a cross-sectional shape of a circle with a portion removed to result in two opposing flat sides 388j and 392j, respectively. Adhesive 384j can comprise a double-sided tape and/or a liquid or gel adhesive disposed in the recess (e.g., at sides 388j). In other embodiments, hub 140m and the corresponding recess can have dissimilar cross-sectional shapes (e.g., recess 340j can have a circular cross-sectional shape). To facilitate insertion of hub 140m into recess 340j, one or both of hub 140m and recess 340j can be tapered (e.g., hub 140m can have a transverse dimension that is relatively smaller at second end 142 and increases along a portion of hub 140m approaching first end 141, and/or recess 340j can have a relatively larger transverse dimension (e.g., diameter) at first end 308j that increases along a portion of recess 340j approaching second end 312j). Coupler 300j further differs from coupler 300i, for example, in that drive hub 304j includes a recess 324j that is sized to receive a second hub (not shown, but similar to second hub 150a of IO device 100a) in combination with first hub 140m of IO device 100m.

Figure 13A:
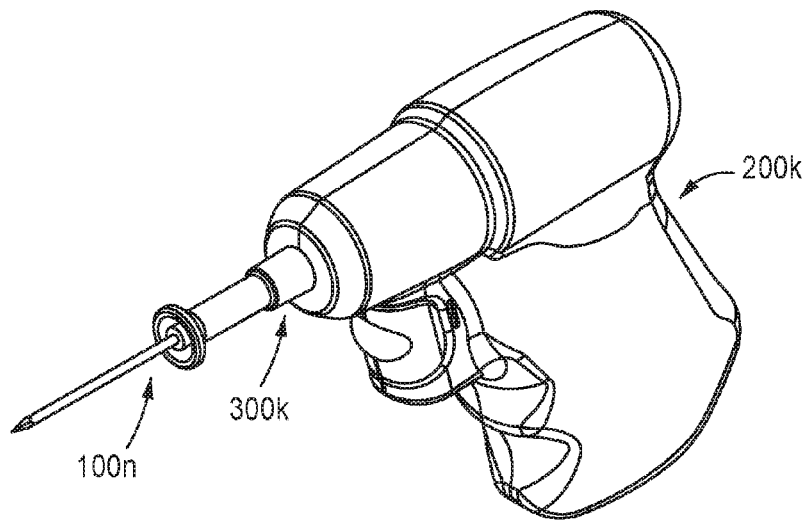
FIGS. 13A-13C depict various views of an eleventh embodiment of the present couplers in combination with a powered driver and an IO device.
Figure 13B:
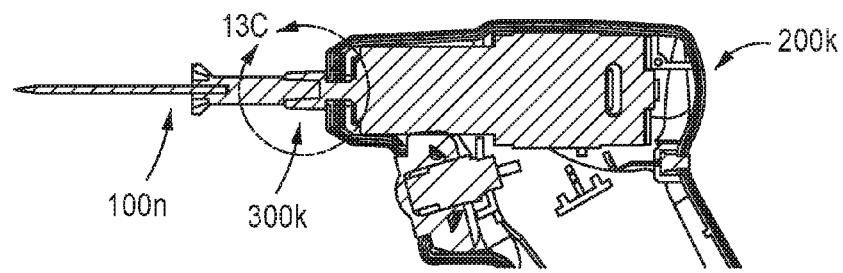
Figure 13C:
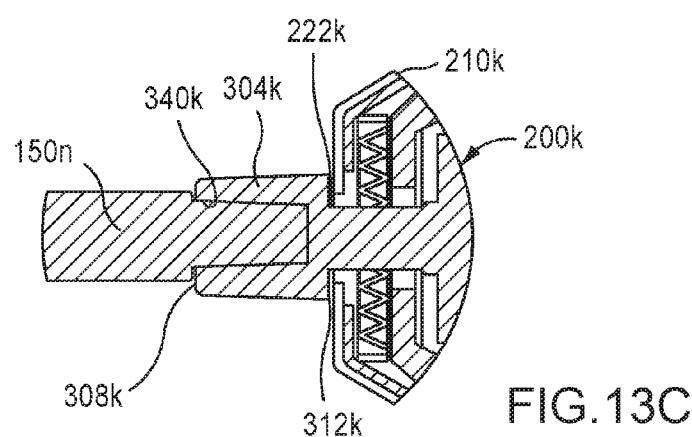

FIGS. 13A-13C depict various views of an eleventh embodiment 300k of the present couplers in combination with a powered driver 200k and an IO device 100n that is configured to provide access to an interior of a bone (e.g., similar in some respects to IO device 100c). In the embodiment shown, coupler 300k comprises a drive hub 304k having a first end 308k and a second end 312k configured to be coupled in fixed relation to driveshaft 222k of driver 200k (e.g., second end 312k is unitary with driveshaft 222k in the embodiment shown). In this embodiment, first end 308k includes a recess 340k configured to receive a portion of hub assembly 130n (e.g., hub 150n) of IO device 100n. In the embodiment shown, recess 340k has a cross-sectional shape (e.g., hexagonal) corresponding to the cross-sectional shape (e.g., hexagonal) of the portion of the IO device such that if the portion of the IO device is inserted into the recess, the drive hub will resist rotation of the IO device relative to the drive hub. To facilitate insertion of hub 150n into recess 340k, one or both of hub 150n and recess 340k can be tapered (e.g., hub 150n can have a transverse dimension that is relatively smaller at second end 142 and increases along a portion of hub 150n approaching first end 141, and/or recess 340k can have a relatively larger transverse dimen-sion (e.g., diameter) at first end 308k that increases along a portion of recess 340k approaching second end 312k).

Figure 14A:
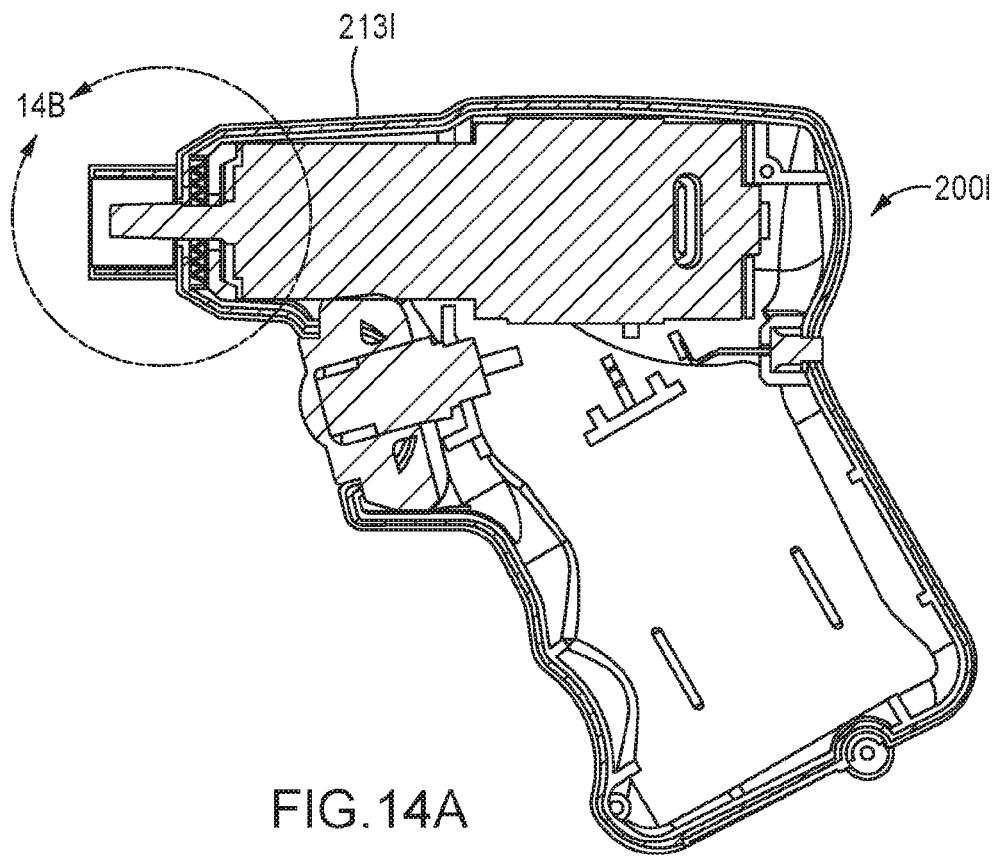
FIGS. 14A-14B depict side cross-sectional views of a powered driver for use with at least some embodiments of the present couplers.
Figure 14B:
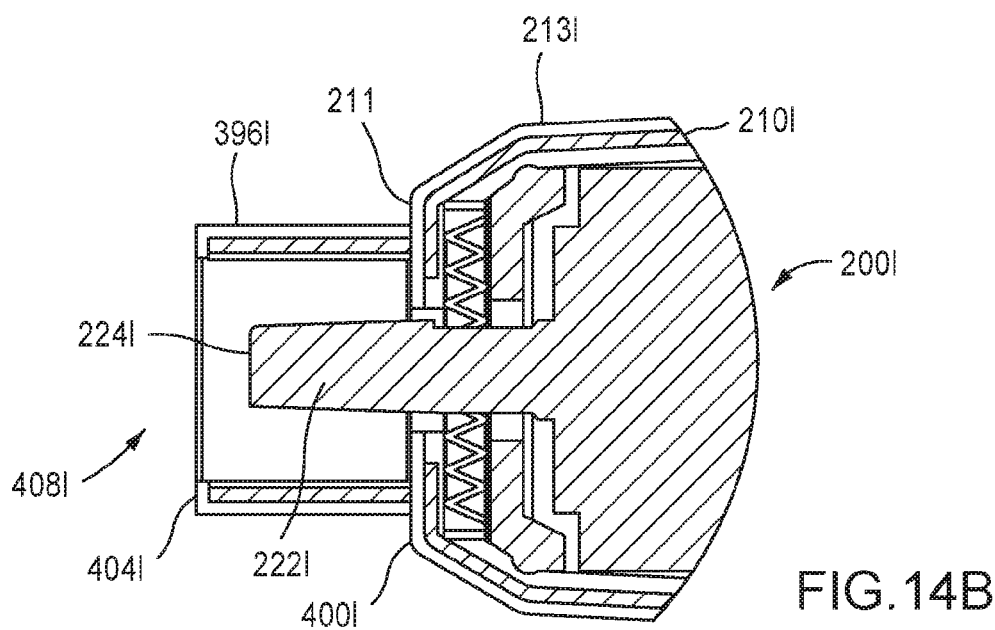

FIGS. 14A-14B depict side cross-sectional views of a powered driver 200l for use with at least some embodiments of the present couplers. In the embodiment shown, driver 200l comprises: a housing 210l having a body portion 213l and a shroud portion 396l. In this embodiment, body portion 213l has a sidewall 400l defining distal end 211 of the body portion, and shroud portion 396l has a cylindrical sidewall 404l extending from distal end 211 of the body portion. In the embodiment shown, shroud portion 396l has an open distal end 408l. In the embodiment shown, driveshaft 222l has a distal end 224l extending from body portion 213l (e.g., past distal end 211 and into shroud portion 396l). In this embodiment, driver 200l is configured to be coupled to an IO device (e.g., 100c) having a hub (e.g., 140c and/or 150c) with a recess 186 sized to receive distal end 224l of the driveshaft, such that the distal end of the driveshaft extends into recess 186 and the hub (e.g., 140c and/or 150c) of the IO device is at least partially disposed in the shroud portion of the housing. For example, in this embodiment, if IO device 100c is coupled to driver 200l, first end 141 of hub 140c is even with or extends outwardly past distal end 408l.

Figure 15A:
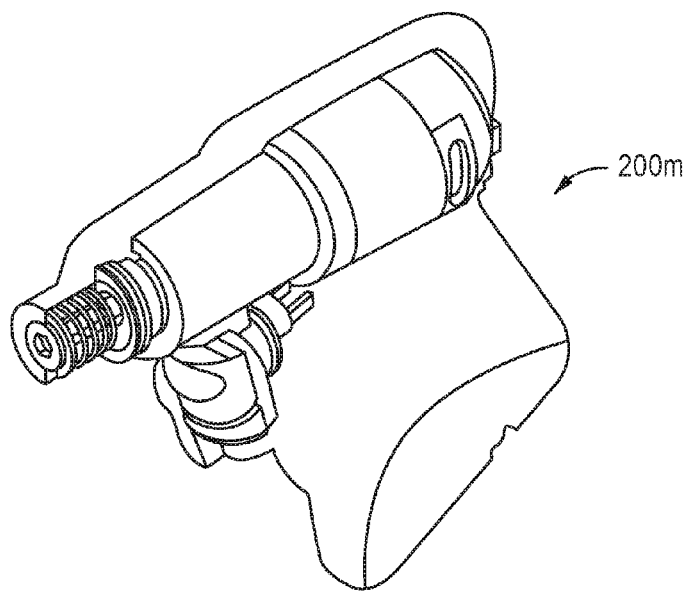
FIGS. 15A-15C depict various views of embodiment of a powered driver 200m for use with at least some embodiments of the present couplers.
Figures 15B, 15C:
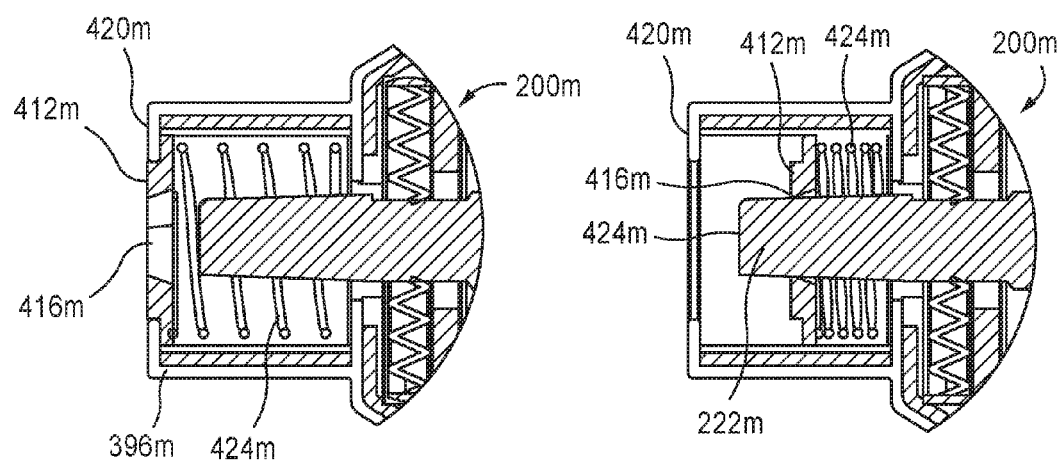

FIGS. 15A-15C depict various views of another embodiment of a powered driver 200m for use with at least some embodiments of the present couplers. Driver 200m is similar in many respects to driver 200l, and therefore the differences in driver 200m will primarily be described here. In the embodiment shown, driver 200m comprises a plate 412m having an opening 416m that is disposed in a shroud portion 396m with driveshaft 222m aligned with opening 416m such that the plate is movable with shroud portion 396m along a length of the driveshaft. Shroud portion 396m that is similar to shroud portion 396l, with the exception that shroud portion 396m comprises a lip 420m extending inward toward the driveshaft and configured to prevent the plate from exiting the shroud portion, as shown. In this embodiment, driver 200m also comprises a spring 424m disposed between plate 412m and distal end 211 of body portion 213m of housing 210m such that the spring biases the plate in a direction toward open end 408m of the shroud portion.

Figure 16A:
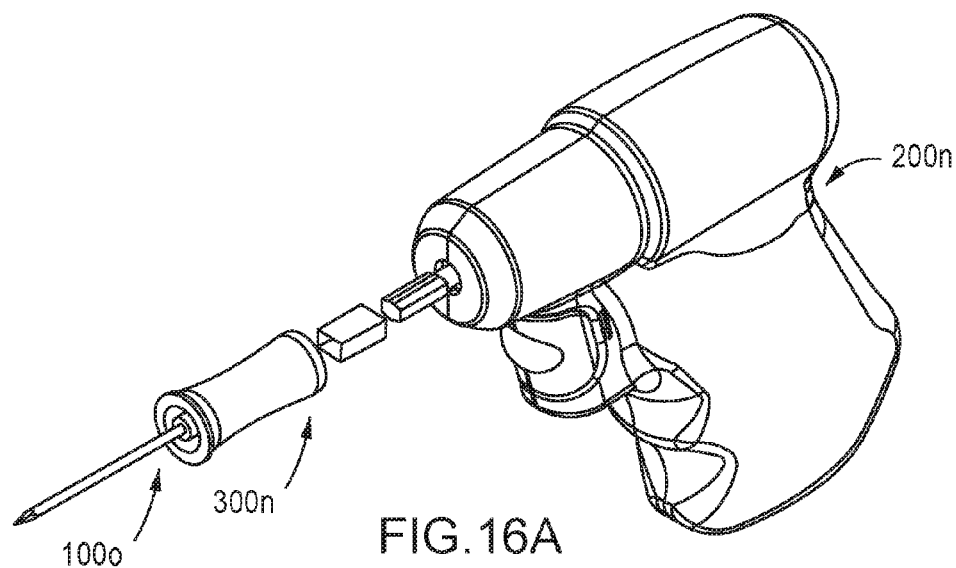
FIGS. 16A-16C depict various views of a twelfth embodiment of the present couplers in combination with a powered driver and an IO device.
Figure 16B:
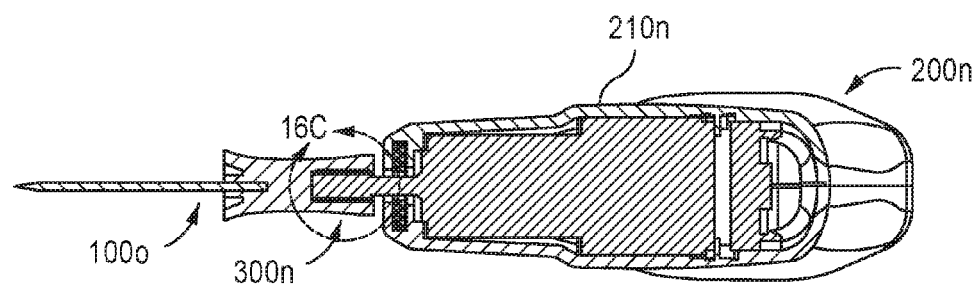
Figure 16C:
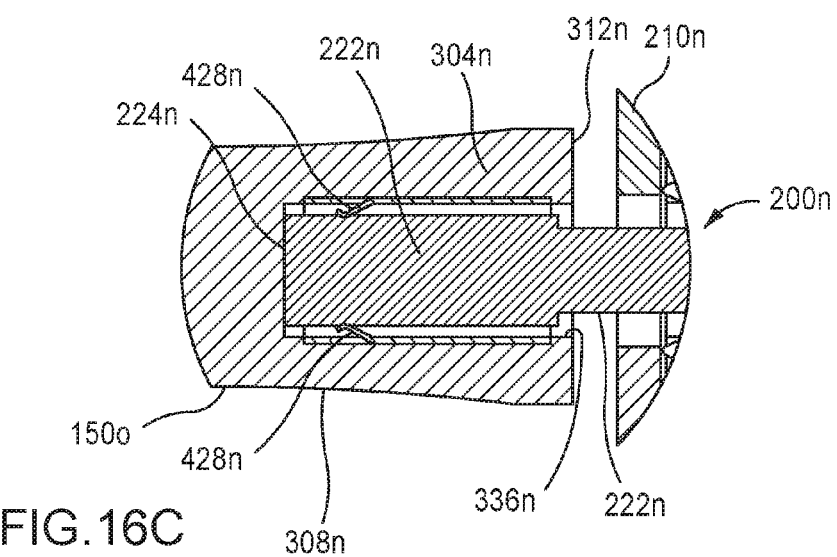
Figure 17A:
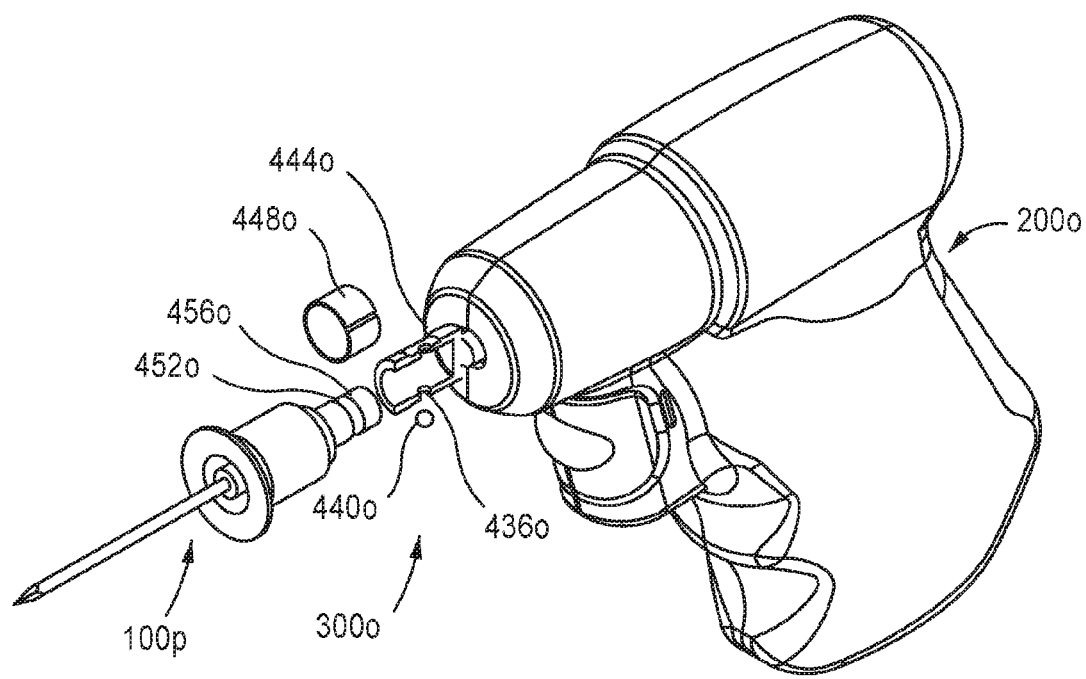
FIGS. 17A-17D depict various views of a thirteenth embodiment of the present couplers in combination with a powered driver and an IO device.
Figure 17B:
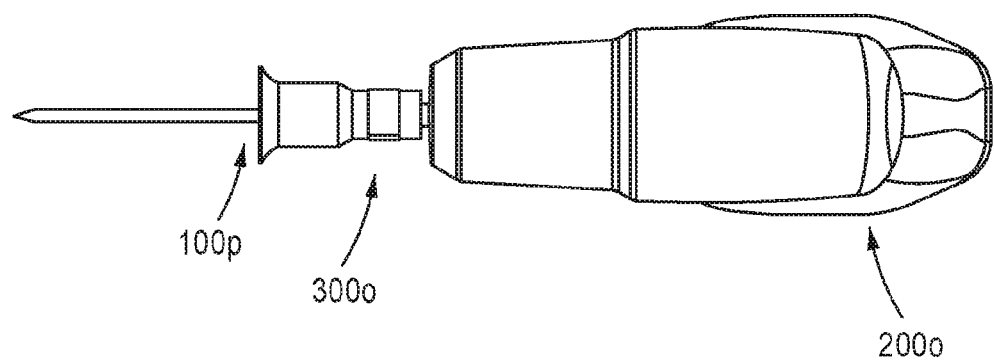
Figure 17C:
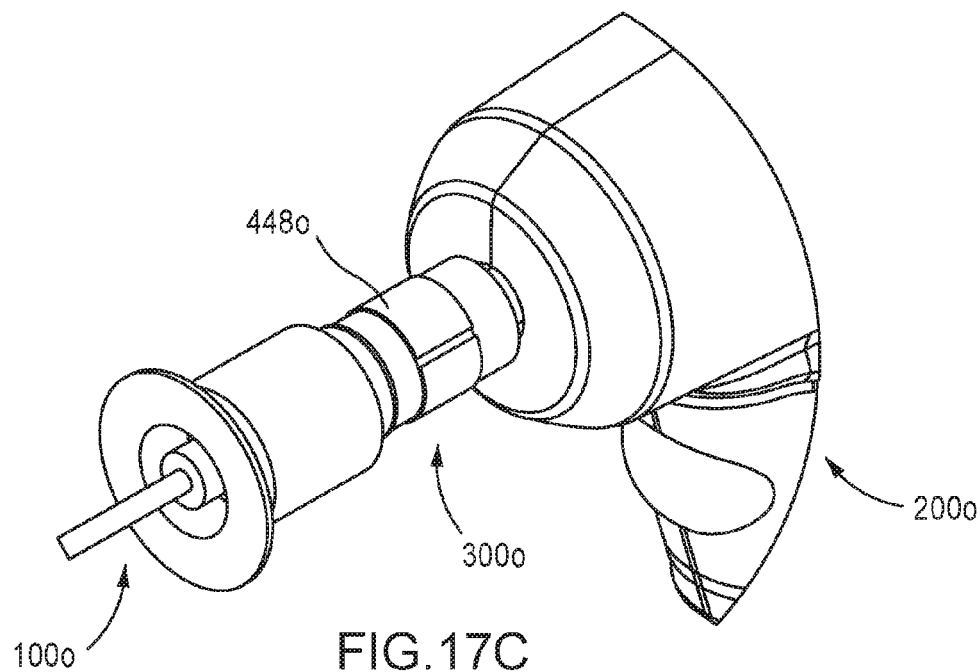
Figure 17D:
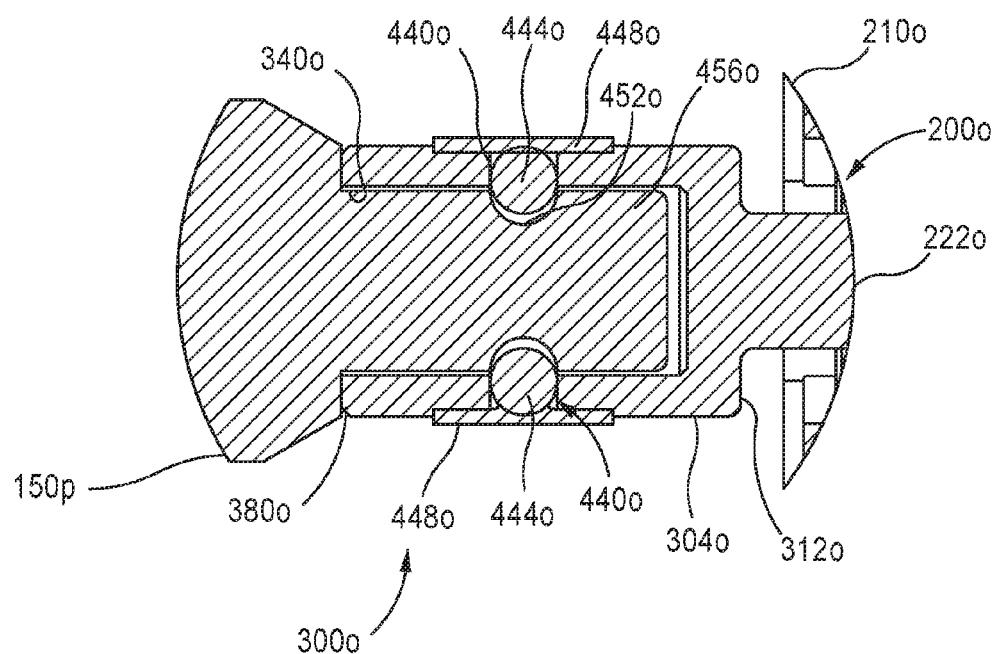

FIGS. 16A-16C depict various views of a twelfth embodiment 300n of the present couplers in combination with a powered driver 200n and an IO device 100o that is configured to provide access to an interior of a bone (e.g., similar in some respects to IO device 100c). In the embodiment shown, coupler 300n comprises a drive hub 304n having a first end 308n and a second end 312n including a recess 336n configured to receive a driveshaft 222n of a driver 200n. In the embodiment shown, coupler 300n further comprises one or more (e.g., two, as shown) resilient clips 428n biased toward an axis of rotation of the drive hub (e.g., and of driveshaft 222n). For example, in this embodiment, coupler 300n comprises a hollow sleeve 332n configured to be disposed around recess 336n such that driveshaft 222n, if inserted into the recess, will also be disposed in the hollow sleeve. In this embodiment, resilient clips 428n are unitary with sleeve 432n (e.g., comprise a single piece of sheet metal). As described above for other embodiments, recess 336n has a cross-sectional shape corresponding to the cross-sectional shape of driveshaft 222n such that if the driveshaft is inserted into the recess, drive hub 304n will resist rotating relative to the driveshaft. For example, in this embodiment, both of recess 336n and driveshaft 222n have non-circular (e.g., elongated) cross-sectional shapes. In the embodiment shown, first end 308n is configured to be coupled to IO device 100o (e.g., to resist rotation of the IO device relative to the drive hub). For example, in the embodiment shown, drive hub 304n is unitary with a portion of a hub assembly (e.g., unitary with second hub 150o).

FIGS. 17A-17D depict various views of a thirteenth embodiment 300o of the present couplers in combination with a powered driver 200o and an IO device 100p that is configured to provide access to an interior of a bone (e.g., similar in some respects to IO device 100c). In the embodiment shown, coupler 300o comprises a drive hub 304o having a first end 308o and a second end 312o configured to be coupled in fixed relation to a driveshaft 222o of driver 200o (e.g., drive hub 304o can be unitary with driveshaft 222o, as shown). In this embodiment, first end 308o includes a recess 340o configured to receive a hub (e.g., second hub 150p) of IO device 100p. In the embodiment shown, drive hub 304o has a sidewall 436o with at least one (e.g., two, as shown) opening 440o extending through the sidewall in communication with recess 340o. In this embodiment, each opening 440o has an inner cross-sectional area at recess 340o that is smaller than an outer cross-sectional area spaced apart from the inner cross-sectional area. In the embodiment shown, coupler 300o also comprises a ball 444o movably disposed in each opening 440o; and a resilient c-clip 448o disposed around the drive hub such that c-clip 448o biases ball(s) 444o toward a rotational axis of the drive hub (and of the driveshaft). In the embodiment shown, ball(s) 444o each has a maximum cross-sectional area that is larger than the inner cross-sectional area of the respective opening 440o to prevent the ball from falling into recess 340o if driveshaft 222o is not disposed in recess 340o. In this embodiment, second end 312o of drive hub 304o is configured such that if a hub (e.g., second hub 150p) of IO device 100p (which, in this embodiment, has at least one detent 452o configured to align with openings 440o) is inserted into recess 340o, the c-clip will: (i) allow ball(s) 444o to move away from the rotational axis of the drive hub until detent(s) 452o align with ball(s) 444o, and (ii) press ball(s) 444o into detent(s) 452o when detent(s) 452o align with ball(s) 444o to resist removal of the driveshaft from the recess. In some embodiments, hub 150p and/or recess 340o have non-circular cross-sectional shapes (e.g., to resist rotation of hub 150p relative drive hub 304o). In the embodiment shown, drive hub 304o has a circular outer cross-sectional shape. In the embodiment shown, hub 150p includes a projection 456o that includes detent(s) 452o.

Figure 18A:
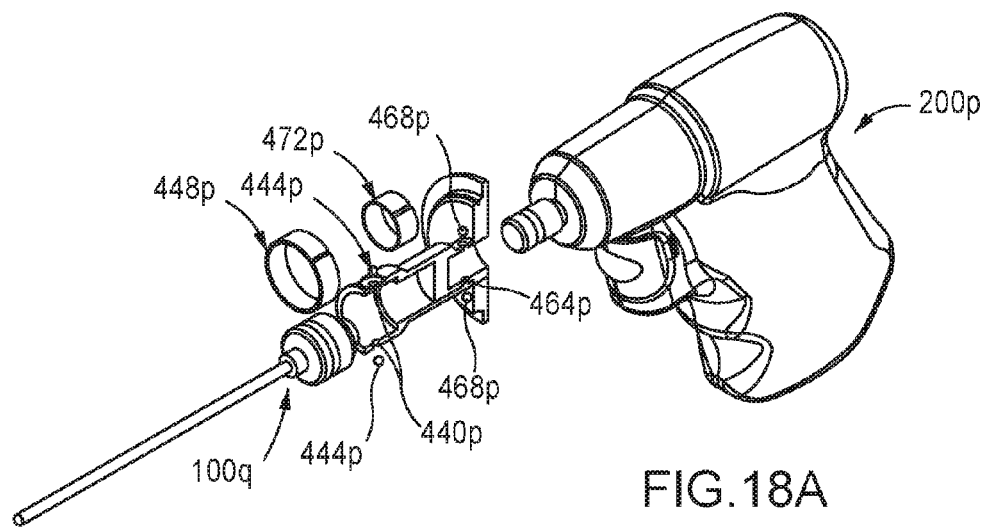
FIGS. 18A-18C depict various views of a fourteenth embodiment of the present couplers in combination with a powered driver and an IO device.
Figure 18B:
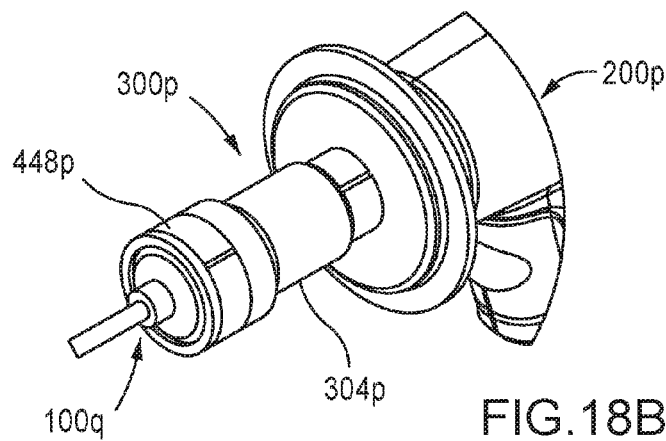
Figure 18C:
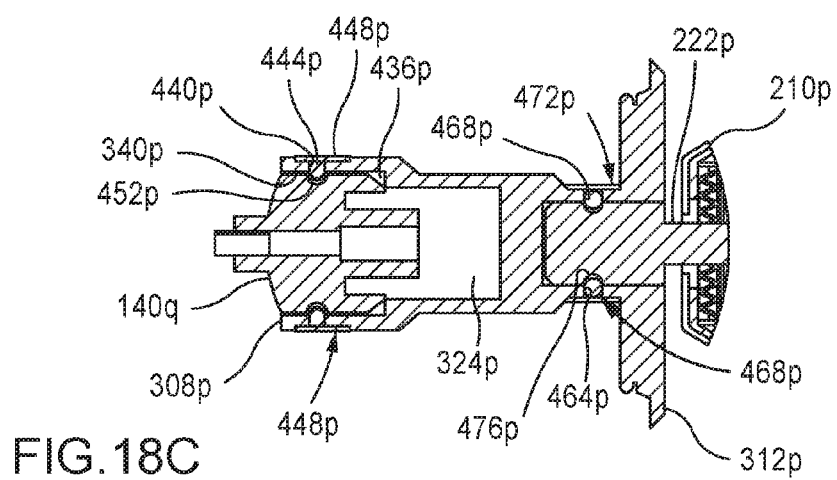

FIGS. 18A-18C depict various views of a fourteenth embodiment 300p of the present couplers in combination with a powered driver 200p and an IO device 100q that is configured for obtaining a sample of bone and/or bone marrow (e.g., similar in some respects to IO devices 100a and/or 100b). In the embodiment shown, coupler 300p comprises a drive hub 304p having a first end 308p and a second end 312p configured to be coupled in fixed relation to a driveshaft 222p of driver 200p (e.g., drive hub 304p can be unitary with driveshaft 222p, as shown). In this embodiment, first end 308p includes a recess 340p configured to receive a hub (e.g., first hub 140q) of IO device 100q. In the embodiment shown, drive hub 304p has a sidewall 436p with at least one (e.g., two, as shown) opening 440p extending through the sidewall in communication with recess 340p. In this embodiment, each opening 440p has an inner cross-sectional area at recess 340p that is smaller than an outer cross-sectional area spaced apart from the inner cross-sectional area. In the embodiment shown, coupler 300p also comprises a ball 444p movably disposed in each opening 440p; and a resilient c-clip 448p disposed around the drive hub such that c-clip 448p biases ball(s) 444p toward a rotational axis of the drive hub (and of the driveshaft). In the embodiment shown, ball(s) 444p each has a maximum cross-sectional area that is larger than the inner cross-sectional area of the respective opening 440p to prevent the ball from falling into recess 340p if hub 140q is not disposed in recess 340p. In this embodiment, second end 312p of drive hub 304p is configured such that if a hub (e.g., first hub 140q) of IO device 100q (which, in this embodiment, has at least one detent 452q configured to align with openings 440p) is inserted into recess 340p, the c-clip will: (i) allow ball(s) 444p to move away from the rotational axis of the drive hub until detent(s) 452p align with ball(s) 444p, and (ii) press ball(s) 444p into detent(s) 452p when detent(s) 452p align with ball(s) 444p to resist removal of hub 140q from the recess. In some embodiments, hub 140q and/or recess 340p have non-circular cross-sectional shapes (e.g., to resist rotation of hub 140q relative to drive hub 304p). In the embodiment shown, drive hub 304p has a circular outer cross-sectional shape.

Coupler 300p differs from coupler 300o, for example, in that first end 308p includes a recess 336p configured to receive driveshaft 222p of driver 200p. In the embodiment shown, drive hub 304p has a sidewall 460p with at least one (e.g., two, as shown) opening 464p extending through the sidewall in communication with recess 336p, with each opening 464p having an inner cross-sectional area at recess 336p that is smaller than an outer cross-sectional area spaced apart from the inner cross-sectional area (e.g., at the outer surface of sidewall 460p). In the embodiment shown, coupler 300p also comprises at least one (e.g., two, as shown) second ball 468p each movably disposed in an opening 464p; and a second resilient c-clip 472p disposed around the drive hub such that the c-clip biases ball(s) 468p toward a rotational axis of the drive hub (and of the driveshaft). In the embodiment shown, ball(s) 468p each has a maximum cross-sectional area that is larger than the inner cross-sectional area of the respective opening 464p to prevent the ball from falling into recess 336p if driveshaft 222p is not disposed in recess 340p. In this embodiment, second end 312p of the drive hub is configured such that if driveshaft 222p (which has at least one detent 4'76p) is inserted into recess 336p, the c-clip will: (i) allow ball(s) 468p to move away from the rotational axis of the drive hub until detent(s) 476p aligns with ball(s) 468p, and (ii) press ball(s) 468p into detent(s) 476p when detent(s) 476p align with ball(s) 468p to resist removal of the driveshaft from the recess. In some embodiments, driveshaft 222p and/or recess 336p have non-circular cross-sectional shapes (e.g., to resist rotation of drive hub 304p relative to driveshaft 222p). In the embodiment shown, drive hub 304p has a circular outer cross-sectional shape. Coupler 300p further differs from coupler 300o, for example, in that drive hub 304p includes a recess 324p that is sized to receive a second hub (not shown, but similar to second hub 150a of IO device 100a).

Figure 19A:
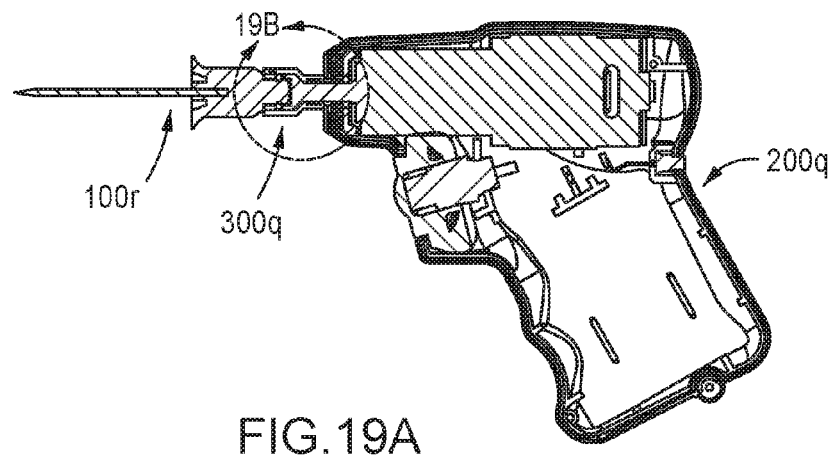
FIGS. 19A-19C depict various views of a fifteenth embodiment of the present couplers in combination with a powered driver and an IO device.
Figure 19B:
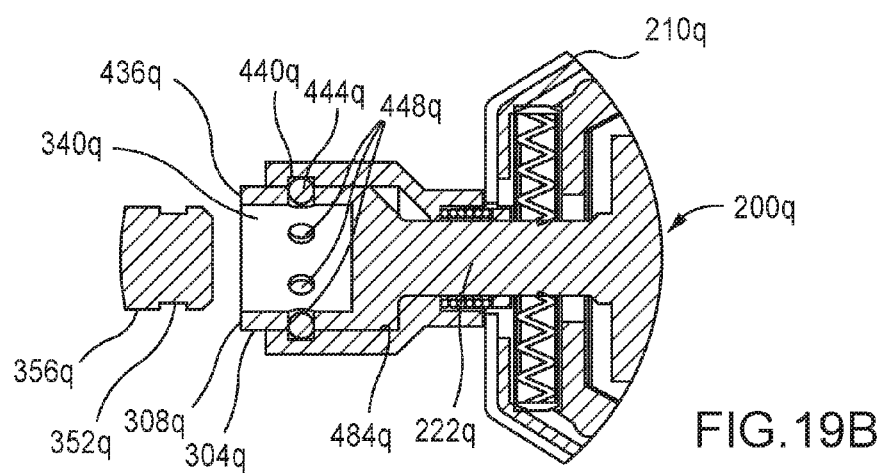
Figure 19C:
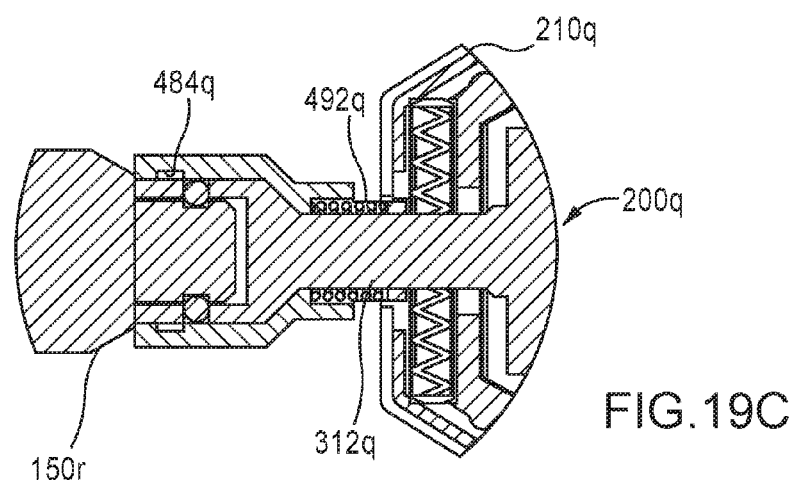

FIGS. 19A-19C depict various views of a fifteenth embodiment 300q of the present couplers in combination with a powered driver 200q and an IO device 100r that is configured to provide access to an interior of a bone (e.g., similar in some respects to IO device 100c). In the embodiment shown, coupler 300q comprises a drive hub 304q having a first end 308q and a second end 312q configured to be coupled in fixed relation to a driveshaft 222q of driver 200q (e.g., drive hub 304q can be unitary with driveshaft 222q, as shown). In this embodiment, first end 308q includes a recess 340q configured to receive a hub (e.g., second hub 150r) of IO device 100r. In the embodiment shown, drive hub 304q has a sidewall 436q with at least one (e.g., two, as shown) opening 440q extending through the sidewall in communication with recess 340q. In this embodiment, each opening 440q has an inner cross-sectional area at recess 340q that is smaller than an outer cross-sectional area spaced apart from the inner cross-sectional area. In the embodiment shown, coupler 300q also comprises a ball 444q movably disposed in each opening 440q; and a collar 480q movably disposed around the drive hub and having an interior surface 484q defining at least one detent 488q adjacent the drive hub. In this embodiment, collar 480q is movable between: (i) a first position (FIG. 19B) in which detent(s) 488q of collar 480q is aligned with opening(s) 440q such that ball(s) 444q can move away from the rotational axis of the drive hub to permit a hub (e.g., 150r) of IO device 100r having a detent 352q to be inserted into or removed from recess 340q (this first position and other such similar positions described in this disclosure may also be characterized as positions that allow the hub to move within the recess without interference from the positive detenting structure (e.g., ball 444q in this embodiment), and (ii) a second position (FIG. 19C) in which detent(s) 488q of collar 480q do not align with opening(s) 440q such that if a hub (e.g., 150r) of IO device 100r having detent(s) 352q is disposed in recess 340q such that detent(s) 352q of hub 150r align with opening(s) 440q, IO device 100r is prevented from being removed from recess 340q (this second position and other such similar positions described in this disclosure may also be characterized as positions that cause the positive detenting structure (e.g., ball 444q in this embodiment) to be sufficiently disposed in the detent (e.g., detent(s) 352q in this embodiment) such that the hub cannot move completely in and out of the recess due to interference with the positive detenting structure). In some embodiments, hub 150r and/or recess 340q have non-circular cross-sectional shapes (e.g., to resist rotation of hub 150r relative to drive hub 304q). In the embodiment shown, hub 150r includes a projection 356q that includes detent(s) 352q. In the embodiment shown, coupler 300q comprises a spring 492q that biases collar 480q toward the second position (FIG. 19C). While not shown in FIGS. 19A-19D, other embodiments can comprise a second recess in second end 312q with openings, balls, and a second collar to engage corresponding detents in a driveshaft of a driver (e.g., similar to coupler 300p).

Figure 20A:
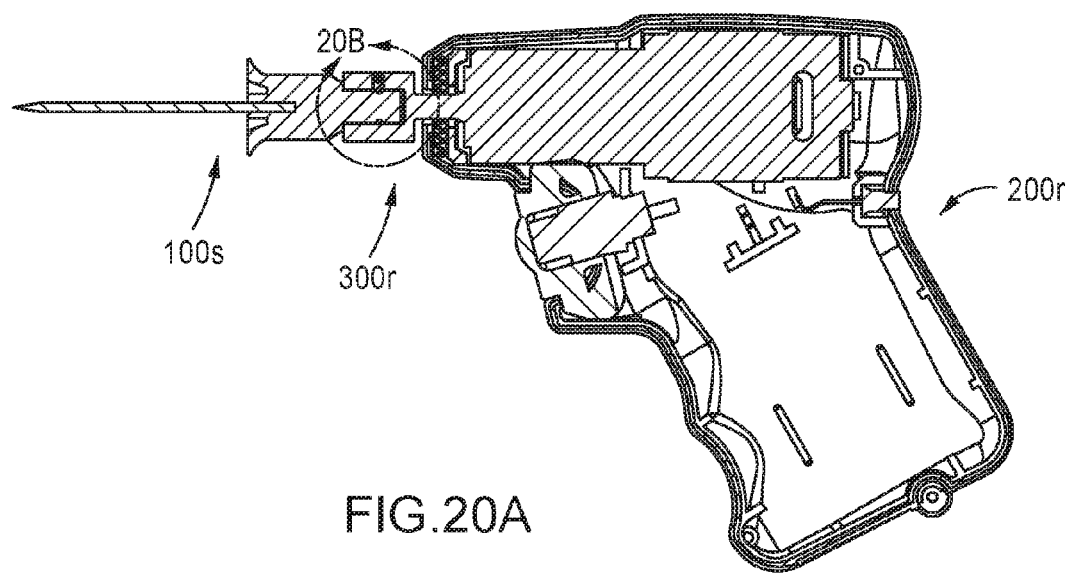
FIGS. 20A-20B depict side cross-sectional views of a sixteenth embodiment of the present couplers in combination with a powered driver and an IO device.
Figure 20B:
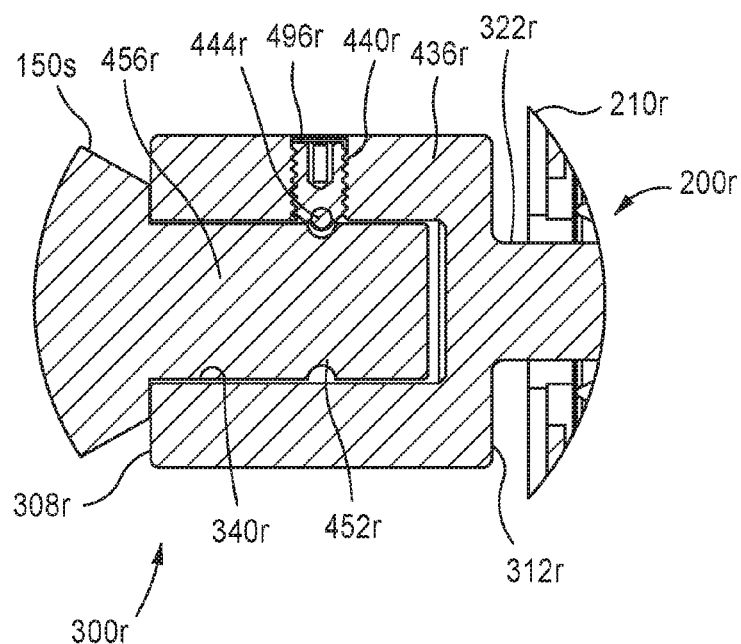

FIGS. 20A-20B depict side cross-sectional views of a sixteenth embodiment 300r of the present couplers in combination with a powered driver 200r and an IO device 100s that is configured to provide access to an interior of a bone (e.g., similar in some respects to IO device 100c). In the embodiment shown, coupler 300r comprises a drive hub 304r having a first end 308r and a second end 312r configured to be coupled in fixed relation to a driveshaft 222r of driver 200r (e.g., drive hub 304r can be unitary with driveshaft 222r, as shown). In this embodiment, first end 308r includes a recess 340r configured to receive a hub 130s (e.g., second hub 150s) of IO device 100s. In the embodiment shown, drive hub 304r has a sidewall 436r with at least one (e.g., two, as shown) opening 440r extending through the sidewall in communication with recess 340r. In the embodiment shown, coupler 300r also comprises at least one set screw 496r with a spring-loaded ball 444r, with set screw(s) 496r disposed in opening(s) 440r such that ball 440r is biased in a direction toward an axis of rotation of the drive hub. In this embodiment, second end 312r of drive hub 304r is configured such that if a hub (e.g., hub 150s) of IO device 100s having at least one detent 452r is inserted into recess 340r: (i) spring-loaded ball(s) 444r will move away from the rotational axis of the drive hub until detent(s) 452r align with ball(s) 444r, and (ii) ball(s) 444r will move into detent(s) 452r when detent(s) align with ball(s) 444r to resist removal of the IO device from recess 340r. In some embodiments, hub 150s and/or recess 340s have non-circular cross-sectional shapes (e.g., to resist rotation of hub 150s relative to drive hub 304r). In the embodiment shown, hub 150s includes a projection 456r that includes detent(s) 452r.

Figure 21A:
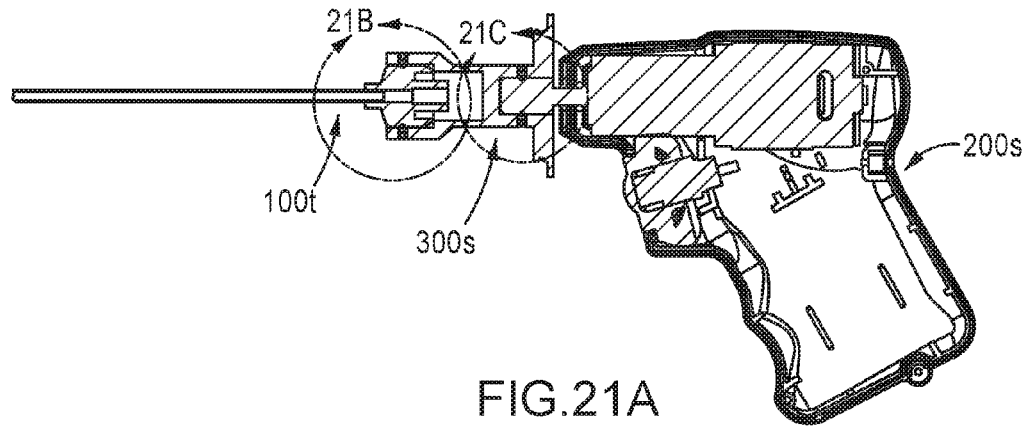
FIGS. 21A-21C depict various views of a seventeenth embodiment of the present couplers in combination with a powered driver and an IO device.
Figure 21B:
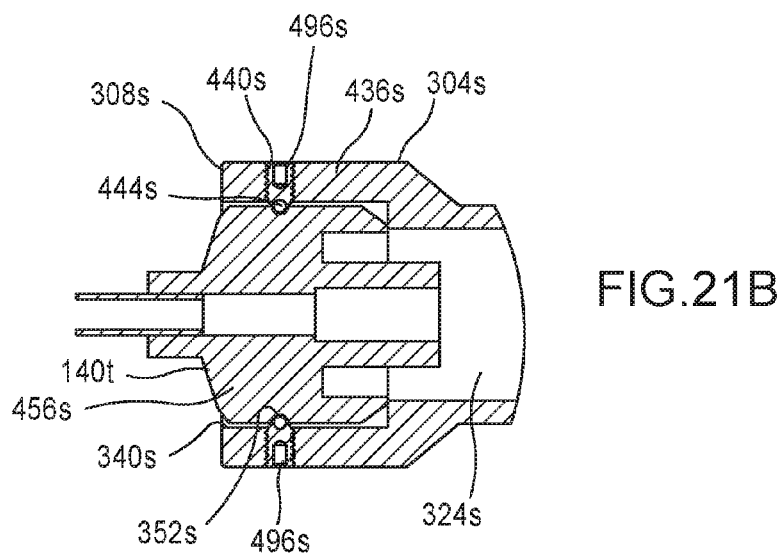
Figure 21C:
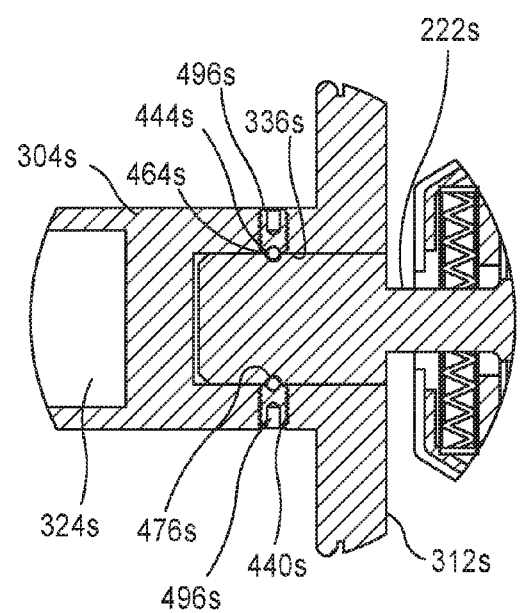

FIGS. 21A-21C depict various views of a seventeenth embodiment 300s of the present couplers in combination with a powered driver 200s and an IO device 100t that is configured for obtaining a sample of bone and/or bone marrow (e.g., similar in some respects to IO devices 100a and/or 100b). In the embodiment shown, coupler 300s comprises a drive hub 304s having a first end 308s and a second end 312s configured to be coupled in fixed relation to a driveshaft 222s of driver 200s. In this embodiment, first end 308s includes a recess 340s configured to receive a hub (e.g., first hub 140t) of IO device 100t. In the embodiment shown, drive hub 304s has a sidewall 436s, a distal portion of which has at least one (e.g., two, as shown) opening 440s extending through the sidewall in communication with recess 340s. In the embodiment shown, coupler 300s also comprises at least one set screw 496s with a spring-loaded ball 444s (these and others like them in this disclosure may also be characterized collectively as a spring-loaded ball plunger and a set screw), with set screw(s) 496s disposed in opening(s) 440s such that ball 444s is biased in a direction toward an axis of rotation of the drive hub. In this embodiment, second end 312s of drive hub 304s is configured such that if a hub (e.g., hub 140t) of IO device 100t having at least one detent 352s is inserted into recess 340s: (i) spring-loaded ball(s) 444s will move away from the rotational axis of the drive hub until detent(s) 352s align with ball(s) 444s, and (ii) ball(s) 444s will move into detent(s) 352s when detent(s) align with ball(s) 444s to resist removal of the IO device from recess 340s. In some embodiments, hub 140t and/or recess 340s have non-circular cross-sectional shapes (e.g., to resist rotation of hub 140t relative to drive hub 304s). In the embodiment shown, hub 140t includes a projection 456s that includes detent(s) 452s.

Coupler 300s differs from coupler 300r, for example, in that second end 312s includes a recess 336s configured to receive driveshaft 222s of driver 200s. In the embodiment shown, a proximal portion of sidewall 3460s (the proximal portion having a cross-sectional area that is smaller than a cross-sectional area of the distal portion referenced above) has at least one (e.g., two, as shown) opening 464s extending through the sidewall in communication with recess 336s. In the embodiment shown, coupler 300s also comprises at least one set screw 496s with a spring loaded ball 444s, with set screw(s) 496s disposed in opening(s) 464s such that ball(s) 444s are biased in a direction toward an axis of rotation of the drive hub. In this embodiment, second end of drive hub 304s is configured such that if driveshaft 222s (which has at least one detent 476s) is inserted into recess 336s: (i) ball(s) 444s of screw(s) 496s will move away from the rotational axis of the drive hub until detent(s) 476s aligns with ball(s) 444s, and (ii) ball(s) 444s of screw(s) 496s will move into detent(s) 476s when detent(s) 476s align with ball(s) 444s to resist removal of driveshaft 222s from recess 336s. In some embodiments, driveshaft 222s and/or recess 336s have non-circular cross-sectional shapes (e.g., to resist rotation of drive hub 304s relative to driveshaft 222s). In the embodiment shown, drive hub 304s has a circular outer cross-sectional shape. Coupler 300s further differs from coupler 300r, for example, in that drive hub 304s includes a recess 324s that is sized to receive a second hub (not shown, but similar to second hub 150a of IO device 100a).

Figure 22A:
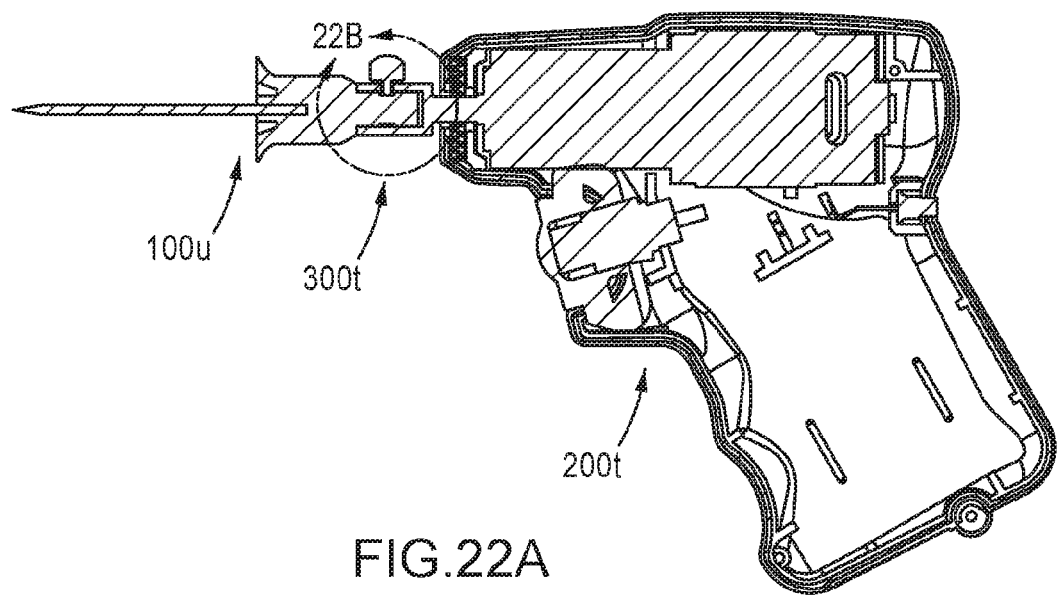
FIGS. 22A-22B depict side cross-sectional views of an eighteenth embodiment of the present couplers in combination with a powered driver and an IO device.
Figure 22B:
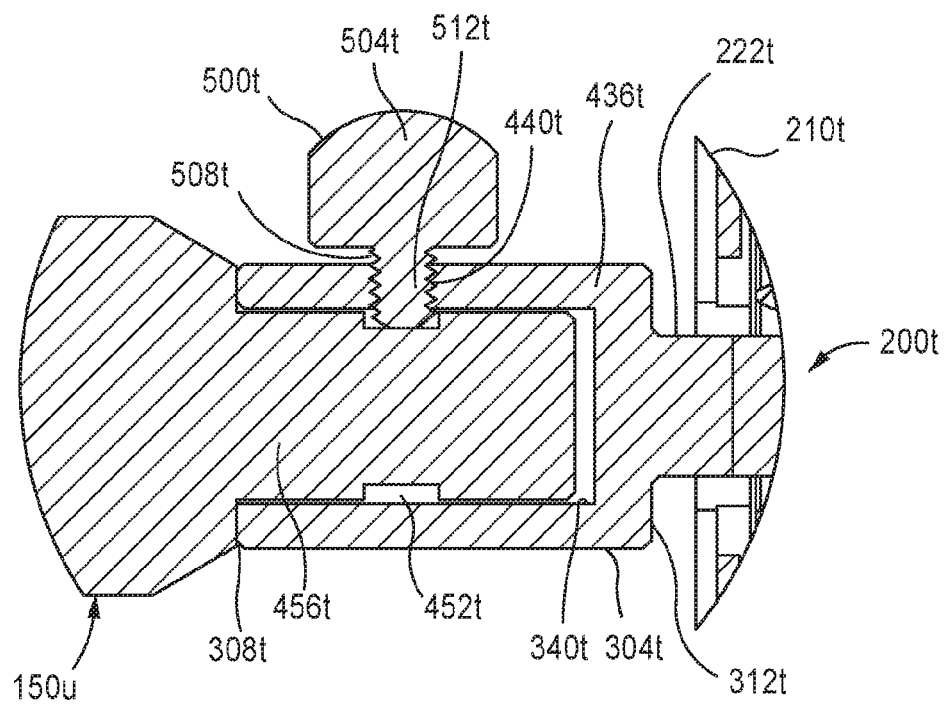

FIGS. 22A-22B depict side cross-sectional views of an eighteenth embodiment 300t of the present couplers in combination with a powered driver 200t and an IO device 100u that is configured to provide access to an interior of a bone (e.g., similar in some respects to IO device 100c). In the embodiment shown, coupler 300t comprises a drive hub 304t having a first end 308t and a second end 312t configured to be coupled in fixed relation to a driveshaft 222t of driver 200t (e.g., drive hub 304t can be unitary with driveshaft 222t, as shown). In this embodiment, first end 308t includes a recess 340t configured to receive a hub (e.g., second hub 150u) of IO device 100u. In the embodiment shown, drive hub 304t has a sidewall 436t with at least one opening 440t extending through the sidewall in communication with recess 340t. In the embodiment shown, coupler 300t also comprises a screw 500t having an enlarged head 504t and a threaded shaft 508t with a distal end 512t, the screw threaded into opening 440t with the distal end facing in a direction toward an axis of rotation of the drive hub. In this embodiment, screw 500t is rotatable between: (i) a first position in which distal end 512t does not extend into recess 340t to permit hub 150u of IO device 100u having a detent 452t to be inserted into or removed from recess 340t; and (ii) a second position in which distal end 512t extends into second recess 340t such that if hub 150u of IO device 100u having detent(s) 452t is disposed in recess 340t such that detent 452t is aligned with opening 440t (and thereby screw 500t), IO device 100u is prevented from being removed from recess 340t (e.g., as shown in FIG. 22B). In some embodiments, hub 150u and/or recess 340t have non-circular cross-sectional shapes (e.g., to resist rotation of hub 150u relative to drive hub 304t). In the embodiment shown, hub 150u includes a projection 456t that includes detent(s) 452t.

Figure 23A:
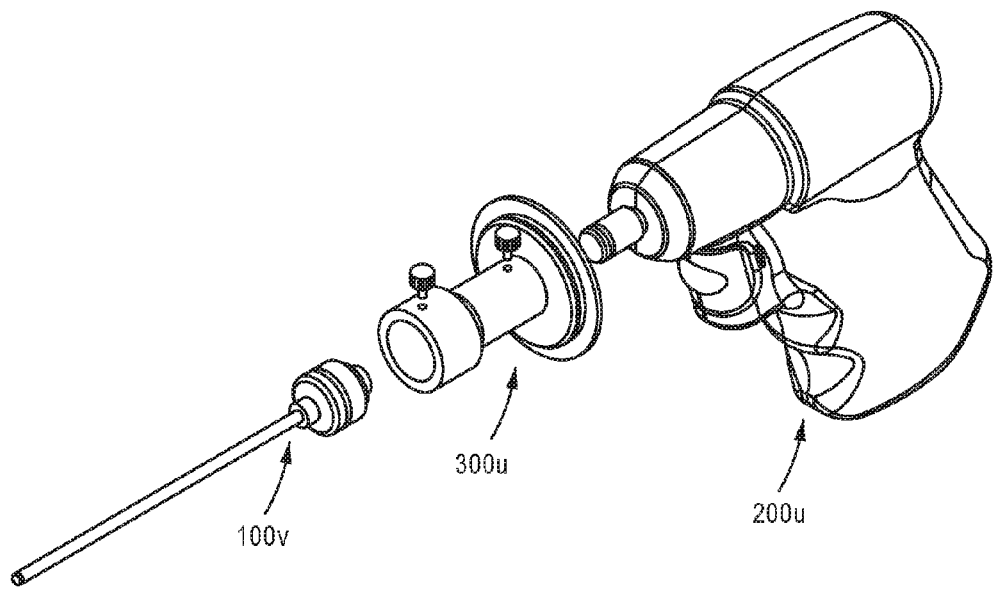
FIGS. 23A-23B depict perspective and side cross-sectional views, respectively, of a nineteenth embodiment of the present couplers in combination with a powered driver and an IO device.
Figure 23B:
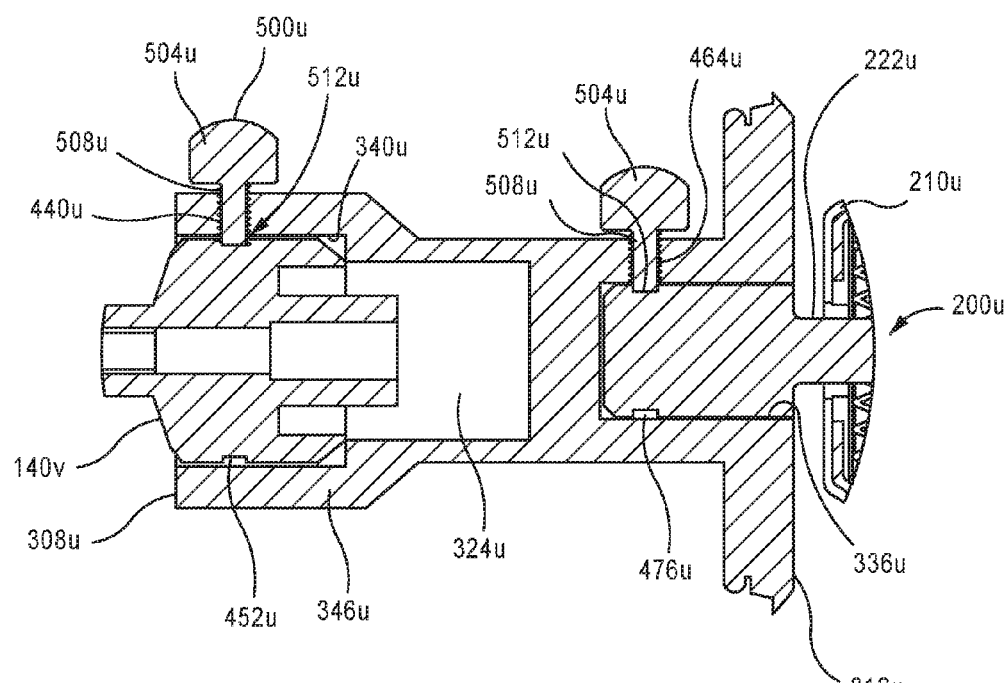

FIGS. 23A-23B depict perspective and side cross-sectional views, respectively, of a nineteenth embodiment 300u of the present couplers in combination with a powered driver 200u and an IO device 100v that is configured for obtaining a sample of bone and/or bone marrow (e.g., similar in some respects to IO devices 100a and/or 100b). In the embodiment shown, coupler 300u comprises a drive hub 304u having a first end 308u and a second end 312u configured to be coupled in fixed relation to a driveshaft 222u of driver 200u (e.g., drive hub 304u can be unitary with driveshaft 222u, as shown). In this embodiment, first end 308u includes a recess 340u configured to receive a hub (e.g., first hub 140v) of IO device 100v. In the embodiment shown, drive hub 304u has a sidewall 436u, a distal portion of which has at least one opening 440u extending through the sidewall in communication with recess 340u. In the embodiment shown, coupler 300u also comprises a screw 500u having an enlarged head 504u and a threaded shaft 508u with a distal end 512u, the screw threaded into opening 440u with the distal end facing in a direction toward an axis of rotation of the drive hub. In this embodiment, screw 500u is rotatable between: (i) a first position in which distal end 512u does not extend into recess 340u to permit hub 130v (e.g., hub 150v) of IO device 100v having a detent 452u to be inserted into or removed from recess 340u; and (ii) a second position in which distal end 512u extends into second recess 340u such that if hub 150v of IO device 100v having detent(s) 452u is disposed in recess 340u such that detent 452u is aligned with opening 440u (and thereby screw 500u), IO device 100v is prevented from being removed from recess 340u (e.g., as shown in FIG. 23B). In some embodiments, hub 150v and/or recess 340u have non-circular cross-sectional shapes (e.g., to resist rotation of hub 150v relative to drive hub 304u). In the embodiment shown, hub 150v includes a projection 456u that includes detent(s) 452u.

Coupler 300u differs from coupler 300t, for example, in that second end 312u includes a recess 336u configured to receive driveshaft 222u of driver 200u. In the embodiment shown, a proximal portion of sidewall 346u (the proximal portion having a cross-sectional area that is smaller than a cross-sectional area of the distal portion referenced above) has at least one (e.g., two, as shown) opening 464u extending through the sidewall in communication with recess 336u. In the embodiment shown, coupler 300u also comprises a second screw 500u having an enlarged head 504u and a threaded shaft 508u with a distal end 512u, the second screw threaded into opening 464u with the distal end facing in a direction toward an axis of rotation of the drive hub. In this embodiment, the second screw is rotatable between: (i) a first position in which distal end 512u does not extend into recess 336u to permit driveshaft 222u (which has a detent 476u) to be inserted into or removed from recess 336u, and (ii) a second position in which distal end 512u extends into recess 336u such that if driveshaft 222u having detent 476u is disposed in recess 336u such that detent 476u is aligned with opening 464u (and thereby screw 500u), driveshaft 222u is prevented from being removed from recess 336u. In some embodiments, driveshaft 222u and/or recess 336u have non-circular cross-sectional shapes (e.g., to resist rotation of drive hub 304u relative to driveshaft 222u). Coupler 300u further differs from coupler 300t, for example, in that drive hub 304u includes a recess 324u that is sized to receive a second hub (not shown, but similar to second hub 150a of IO device 100a).

Figure 24A:
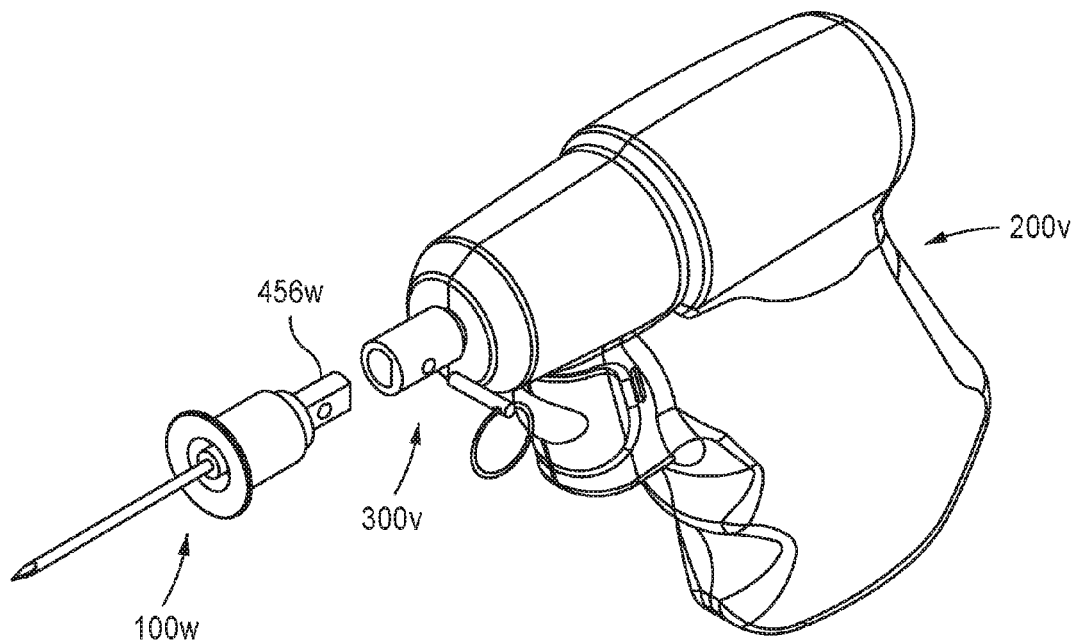
FIGS. 24A-24B depict perspective and side cross-sectional views, respectively, of a twentieth embodiment of the present couplers in combination with a powered driver and an IO device.
Figure 24B:
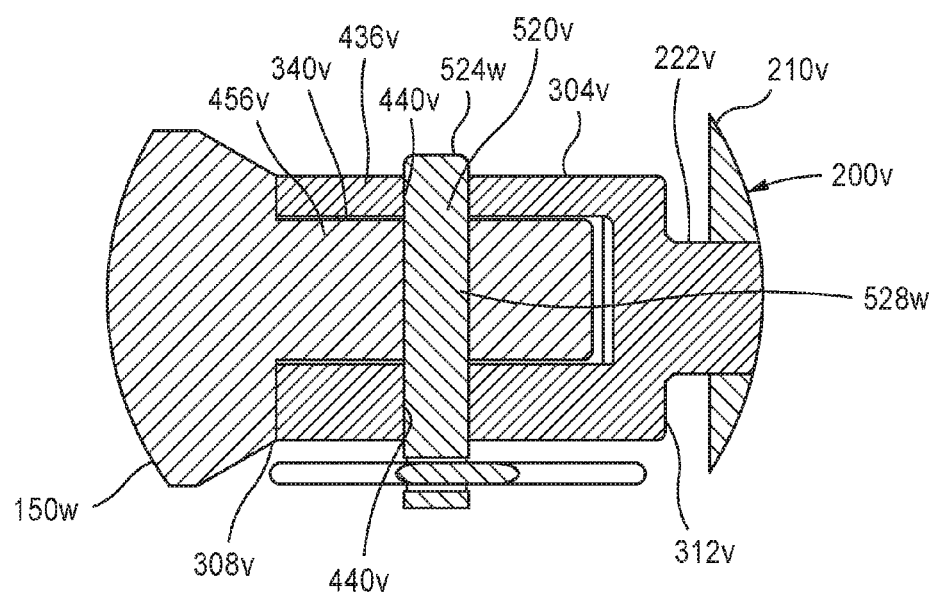

FIGS. 24A-24B depict perspective and side cross-sectional views, respectively, of a twentieth embodiment of the present couplers 300v in combination with a powered driver 200v and an IO device 100w that is configured to provide access to an interior of a bone (e.g., similar in some respects to IO device 100c). In the embodiment shown, coupler 300v comprises a drive hub 304v having a first end 308v and a second end 312v configured to be coupled in fixed relation to a driveshaft 222v of driver 200v (e.g., drive hub 304v can be unitary with driveshaft 222v, as shown). In this embodiment, first end 308v includes a recess 340v configured to receive a hub (e.g., second hub 150w) of IO device 100w. In the embodiment shown, drive hub 304v has a sidewall 436v with at least one (e.g., two, as shown) opening 440v extending through the sidewall in communication with recess 340v. In the embodiment shown, coupler 300v also comprises a pin 520v having a distal end 524v configured to be inserted into opening 440v such that pin 520v extends across a majority (e.g., all) of a width of recess 340v (e.g., and through a second opening 440v on an opposite side of opening 340v, as shown). In this embodiment, pin 520v is movable between: (i) a first position in which distal end 524v does not extend into recess 340v to permit a hub 150w of IO device 100w (which has a transverse passageway 528w) to be inserted into or removed from recess 340v, and (ii) a second position in which pin 520v extends into and across a majority (e.g., all) of recess 340v (as shown in FIG. 24B) such that if hub 150w of IO device 100v having transverse passageway 528w is disposed in recess 340v such that transverse passageway 528w is aligned with opening 440v, pin 520v extends into (e.g., through) transverse passageway 528w to prevent IO device 100w from being removed from recess 340v. In some embodiments, such as the one shown, hub 150w and/or recess 340v have non-circular cross-sectional shapes (e.g., to resist rotation of hub 150w relative to drive hub 304v). In the embodiment shown, hub 150w includes a projection 456v that includes transverse passageway 528w.

Figure 25A:
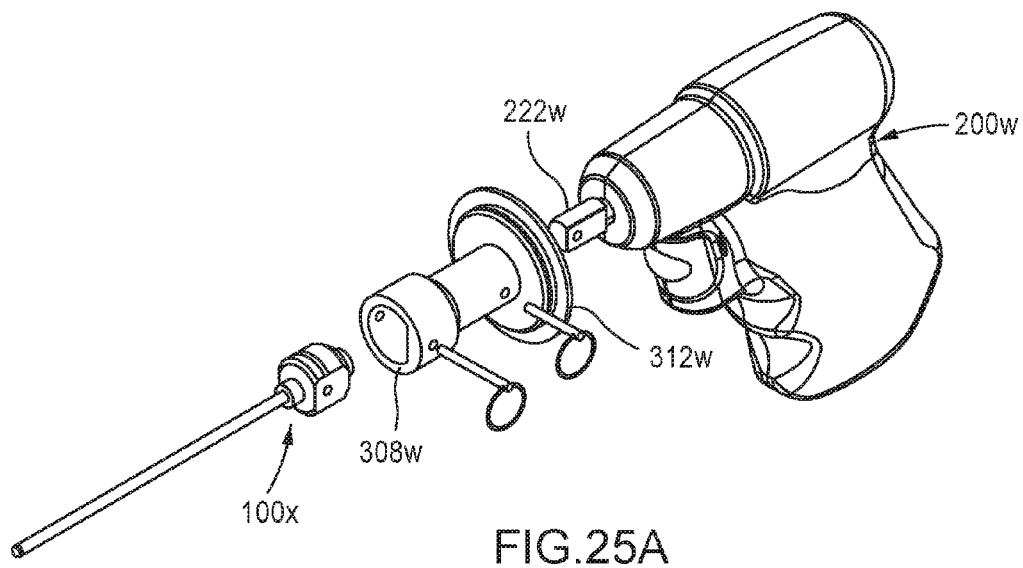
FIGS. 25A-25B depict perspective and side cross-sectional views, respectively, of a twenty-first embodiment of the present couplers in combination with a powered driver and an IO device.
Figure 25B:
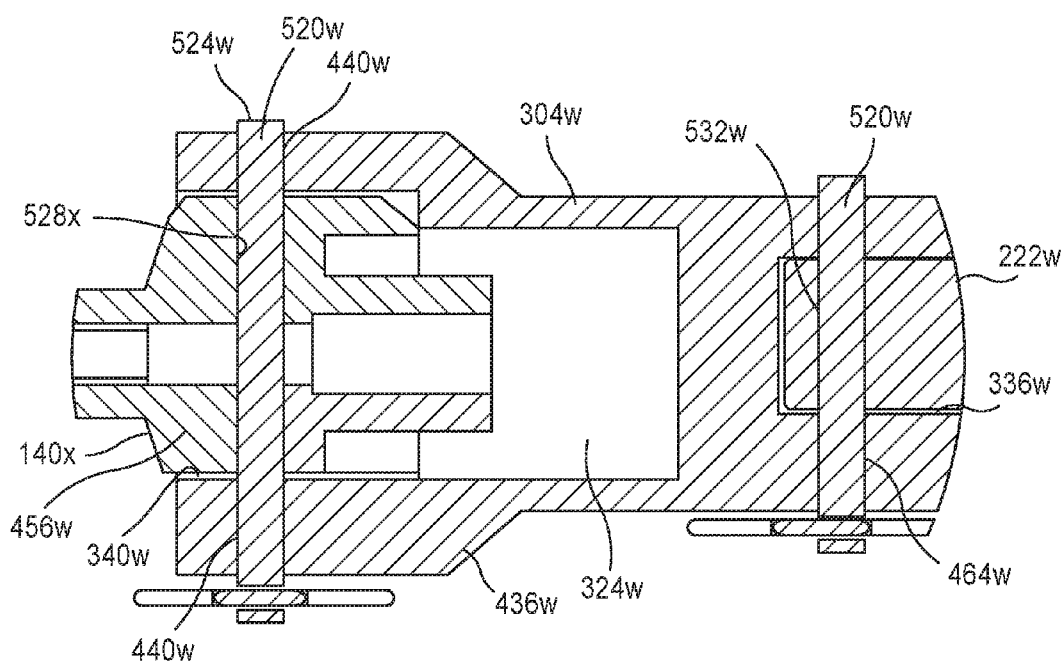

FIGS. 25A-25B depict perspective and side cross-sectional views, respectively, of a twenty-first embodiment 300w of the present couplers in combination with a powered driver 200w and an IO device 100x that is configured for obtaining a sample of bone and/or bone marrow (e.g., similar in some respects to IO devices 100a and/or 100b). In the embodiment shown, coupler 300w comprises a drive hub 304w having a first end 308w and a second end 312w configured to be coupled in fixed relation to a driveshaft 222w of driver 200w. In this embodiment, first end 308w includes a recess 340w configured to receive a hub (e.g., first hub 140x) of IO device 100x. In the embodiment shown, drive hub 304w has a sidewall 436w, a distal portion of which has at least one (e.g., two, as shown) opening 440w extending through the sidewall in communication with recess 340w. In the embodiment shown, coupler 300w also comprises a pin 520w having a distal end 524w configured to be inserted into opening 440w such that pin 520w extends across a majority (e.g., all) of a width of recess 340w (e.g., and through a second opening 440w on an opposite side of opening 340w, as shown). In this embodiment, pin 520w is movable between: (i) a first position in which distal end 524w does not extend into recess 340w to permit a hub 150x (e.g., hub 130x) of IO device 100x (which has a transverse passageway 528x) to be inserted into or removed from recess 340w, and (ii) a second position in which pin 520w extends into and across a majority (e.g., all) of recess 340w (as shown in FIG. 25B) such that if hub 150x of IO device 100x having transverse passageway 528x is disposed in recess 340w such that transverse passageway 528x is aligned with opening 440w, pin 520w extends into (e.g., through) transverse passageway 528x to prevent IO device 100x from being removed from recess 340w. In some embodiments, such as the one shown, hub 150x and/or recess 340w have non-circular cross-sectional shapes (e.g., to resist rotation of hub 150x relative to drive hub 304x). In the embodiment shown, hub 150x includes a projection 456w that includes transverse passageway 528x.

Coupler 300w differs from coupler 300v, for example, in that second end 312w includes a recess 336w configured to receive driveshaft 222w of driver 200w. In the embodiment shown, a proximal portion of sidewall 436w of drive hub 304w (the proximal portion having a cross-sectional area that is smaller than a cross-sectional area of the distal portion referenced above) includes at least one (e.g., two, as shown) opening 464w extending through the sidewall in communication with recess 336w. In the embodiment shown, coupler 300w also comprises a second a pin 520w having a distal end 524w configured to be inserted into opening 464w such that pin 520w extends across a majority (e.g., all) of a width of recess 340w (e.g., and through a second opening 464w on an opposite side of opening 340v, as shown). In this embodiment, pin 520v is movable between: (i) a first position in which distal end 524w does not extend into recess 336w to permit a driveshaft 222w driver 200w (which has a transverse passageway 532w) to be inserted into or removed from recess 336w, and (ii) a second position in which pin 520w extends into and across a majority (e.g., all) of recess 340w (as shown in FIG. 25B) such that if driveshaft 222w of driver 200w having transverse passageway 532w is disposed in recess 336w such that transverse passageway 532w is aligned with opening 464w, pin 520w extends into (e.g., through) transverse passageway 532w to prevent IO device 100x from being removed from recess 336w. In some embodiments, such as the one shown, driveshaft 222w and/or recess 336w have non-circular cross-sectional shapes (e.g., to resist rotation of drive hub 304w relative to driveshaft 222w). Coupler 300w also differs from coupler 300v, for example, in that drive hub 304w includes a recess 324w that is sized to receive a second hub (not shown, but similar to second hub 150a of IO device 100a).

FIGS. 26A-26E depict various views of a twenty-second embodiment 300x of the present couplers in combination with a powered driver 200x and an IO device 100y that is configured to provide access to an interior of a bone (e.g., similar in some respects to IO device 100c). In the embodiment shown, driver 200x is similar in some respects to driver 200l described above with reference to FIGS. 14A-14B. For example, driver 200x comprises a housing 210x having a body portion 213x and a shroud portion 396x. In this embodiment, body portion 213x has a sidewall 400x defining distal end 211 of the body portion, and shroud portion 396x has a cylindrical sidewall 404x extending from distal end 211 of the body portion. In the embodiment shown, shroud portion 396x has an open distal end 408x. In the embodiment shown, driveshaft 222x has a distal end 224x extending from body portion 213x (e.g., past distal end 211 and into shroud portion 396x). However, driver 200x differs from driver 200l, for example, in that shroud portion 396x includes one or more (e.g., two, as shown) projections 536x extending (e.g., in opposite directions) from sidewall 404x (e.g., and away from driveshaft 222x). In this embodiment, projections 536x are shaped as short, circular cylinders.

Figure 26A:
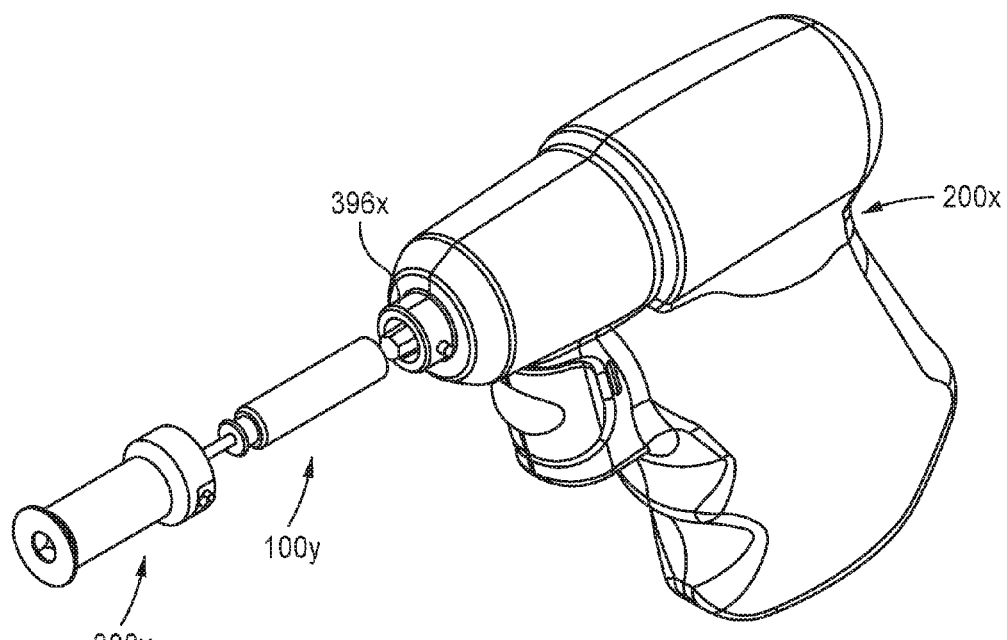
FIGS. 26A-26E depict various views of a twenty-second embodiment of the present couplers in combination with a powered driver and an IO device.
Figure 26B:
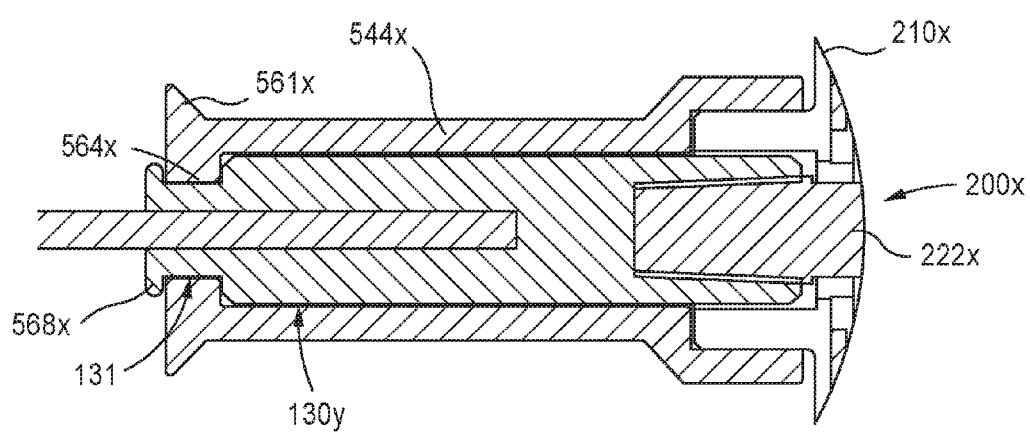
Figure 26C:
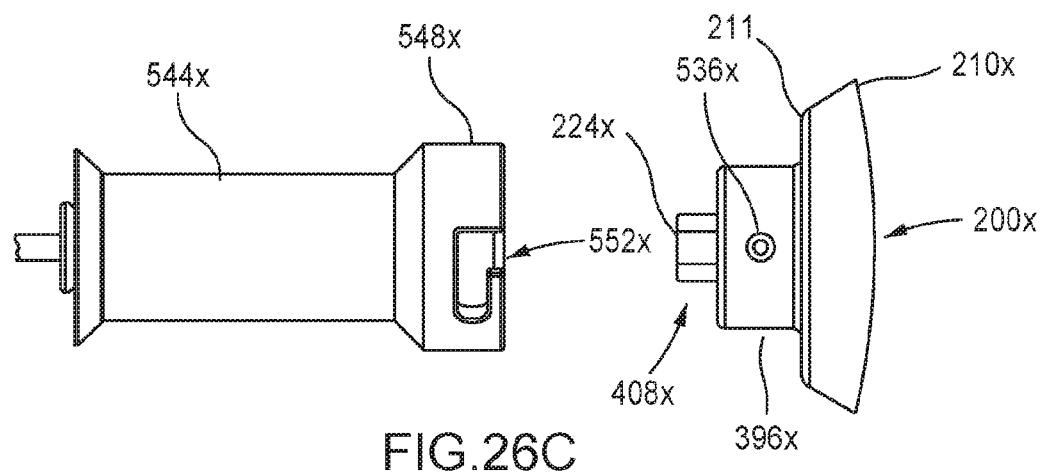
Figure 26D:
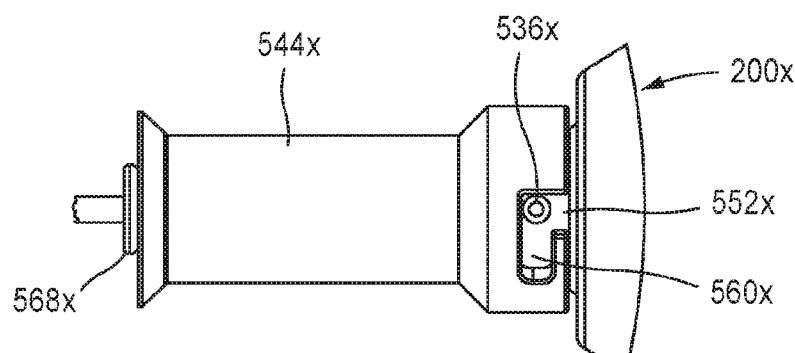
Figure 26E:
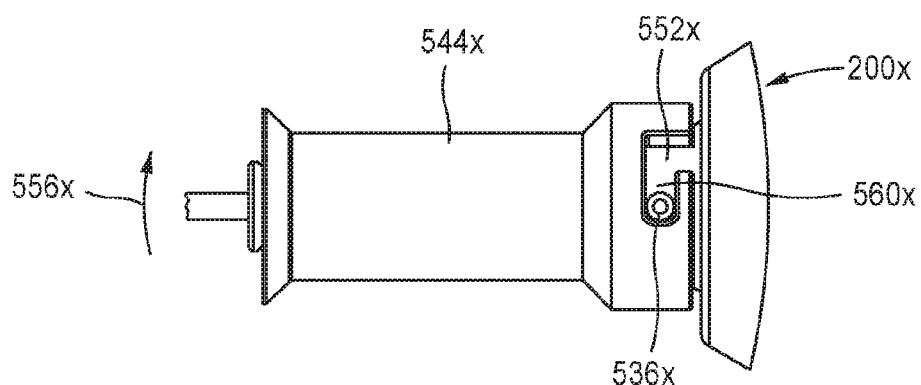

In the embodiment shown, coupler 300x comprises a hollow sleeve 544x configured to be rotatably coupled to a hub (e.g., a first hub and/or a second hub) of IO device 100y. In this embodiment, sleeve 544x includes a proximal portion 548x configured to fit over shroud portion 396x of housing 210x (as shown, for example, in FIG. 26B) to couple the IO device to the driver and resist removal of IO device from the driver. In this embodiment, proximal portion 548x of sleeve 544x comprises one or more (e.g., two, as shown) L-shaped slots 552x each configured to receive a projection 536x if proximal portion 544x of the sleeve is disposed over shroud portion 396x such that sleeve 544x can be rotated in direction 556x relative to shroud portion 396x to resist removal of the IO device from the driver (e.g., to lock the sleeve relative to the driver by seating projections 536x in lateral legs 560x of slots 552x, as shown in FIG. 26E). In this embodiment, distal end 561x of sleeve 544x includes an openings 564x (e.g., with a circular cross-section, as shown) through which a portion of IO device 100y can extend such that the driver can rotate the IO device while sleeve 544x is coupled in fixed relation to the driver. In the embodiment shown, IO device 100y comprises an elongated hub assembly 130y having a first end 131 with a circular cross-section sized to correspond to that of opening 564x (e.g., that is smaller than a portion of hub 130y configured to be disposed immediately inside sleeve 544x). In this embodiment, hub 130y also comprises a flange 568x with a circular cross-section that is larger than opening 564x such that first end 131 can "snap" into opening 564x to (i) maintain its longitudinal position relative to sleeve 544x, (ii) create a tortuous path through opening to reduce the likelihood of contaminants traveling through opening 546x while IO device 100y is coupled to sleeve 544x, and (iii) permit IO device 100y to rotate relative sleeve 544x.

Figure 27A:
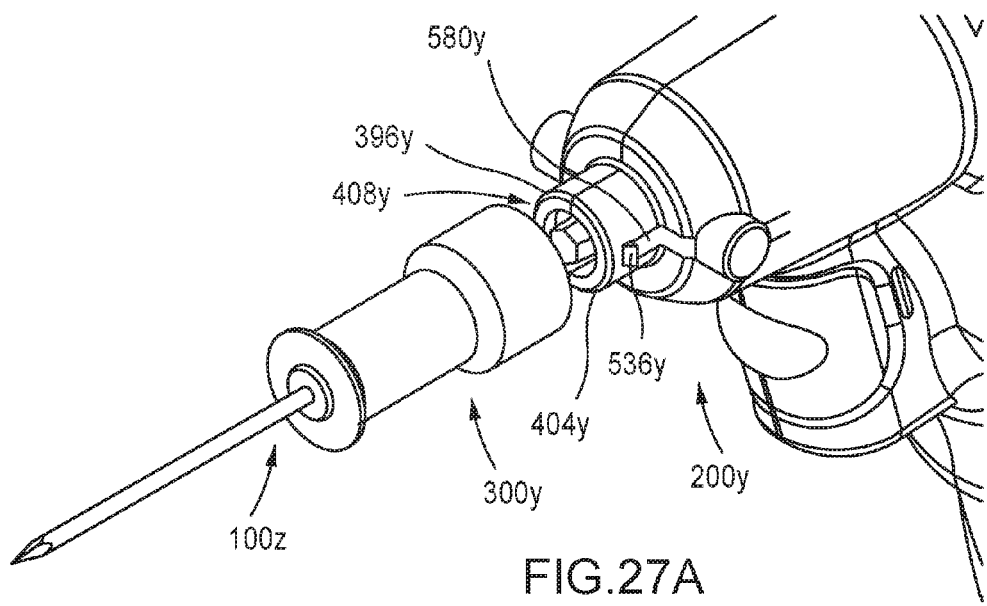
FIGS. 27A-27C depict various views of a twenty-third embodiment of the present couplers in combination with a powered driver and an IO device.
Figure 27B:
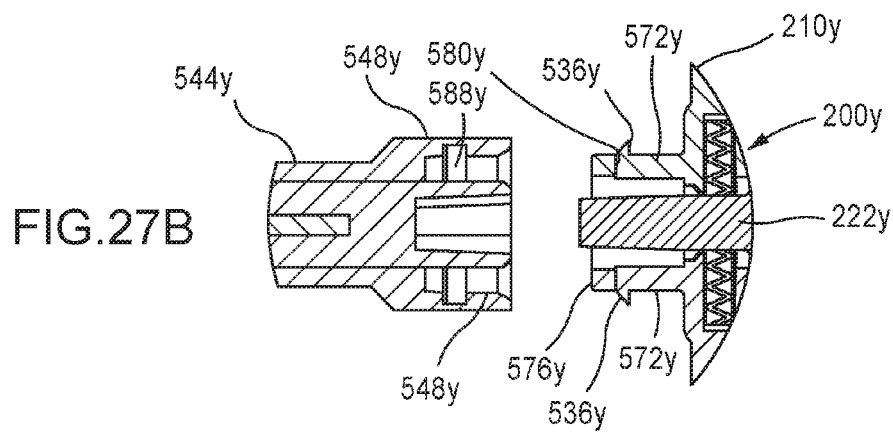
Figure 27C:
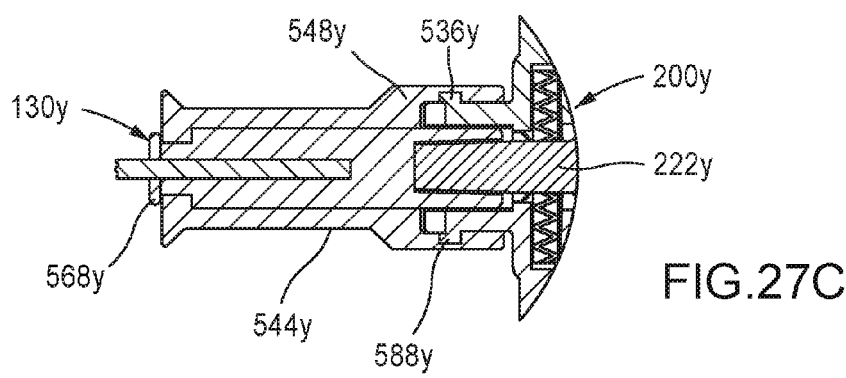

FIGS. 27A-27C depict various views of a twenty-third embodiment 300y of the present couplers in combination with a powered driver 200y and IO device 100z that is configured to provide access to an interior of a bone (e.g., similar in some respects to IO device 100*c*). In the embodiment shown, driver 200*y* is similar in some respects to driver 200*x*. For example, driver 200*y* comprises a housing 210*y* having a body portion 213*y* and a shroud portion 396*y*. In this embodiment, body portion 213*y* has a sidewall 400*y* defining distal end 211 of the body portion, and shroud portion 396*y* has a cylindrical sidewall 404*y* extending from distal end 211 of the body portion. In the embodiment shown, shroud portion 396*y* has an open distal end 408*y*. In the embodiment shown, driveshaft 222*y* has a distal end 224*y* extending from body portion 213*y* past distal end 211 and into shroud portion 396*y*. In the embodiment shown, shroud portion 396*y* includes one or more (e.g., two, as shown) projections 536*y* extending (e.g., in opposite directions) from sidewall 404*y* (e.g., and away from driveshaft 222*y*). Driver 200*y* differs from driver 200*x*, for example, in that shroud portion 396*y* (e.g., sidewall 404*y*) comprises one or more (e.g., two, as shown) resilient portions 572*y* and one or more substantially rigid portions 576*y*, with projections 536*y* extending from resilient portions 572*y* such that the projections are movable relative to driveshaft 222*y*. In this embodiment, resilient portions 572*y* and substantially rigid portions 576*y* comprise the same material, and resilient portions are created by the placement of slots 580*y* between portions 572*y* and 576*y* such that resilient portions 572*y* have less curvature than substantially rigid portions 576*y*, and thereby have less resistance at distal end 408*y* to bending toward driveshaft 222*y* (but still enough resistance to bending to bias resilient portions 572*y* toward a position in which portions 572*y* are substantially aligned with portions 576*y*).

In the embodiment shown, coupler 300*y* comprises a hollow sleeve 544*y* configured to be rotatably coupled to a hub 130*z* (e.g., first hub 140*z* and/or second hub 150*z*) of IO device 100*z*. In this embodiment, sleeve 544*y* includes a proximal portion 548*y* configured to fit over shroud portion 396*y* of housing 210*y* (as shown, for example, in FIG. 27B) to couple the IO device to the driver and resist removal of IO device from the driver. In this embodiment, proximal portion 548*y* includes an interior surface 584*y* defining one or more detents 588*y* configured to receive projections 536*y* of shroud portion 396*y* to resist removal of the IO device from the driver. In this embodiment, sleeve 544*y* can be pressed directly over shroud portion 396*y* (e.g., FIG. 27B to FIG. 27C) such that proximal portion 548*y* will depress projections 536*y* (and resilient portions 572*y*) until detent(s) 588*y* align with detent(s) 588*y*, at which point, resilient portions 572*y* will return to their resting positions and extend projections 536*y* into detent(s) 588*y*. In this embodiment, distal end 560*y* of sleeve 544*y* includes an openings 564*y* (e.g., with a circular cross-section, as shown) through which a portion of IO device 100*z* can extend such that the driver can rotate the IO device while sleeve 544*y* is coupled in fixed relation to the driver. In the embodiment shown, IO device 100*z* comprises an elongated hub assembly 130*z* having a first end 131 with a circular cross-section sized to correspond to that of opening 564*y* (e.g., that is smaller than a portion of hub 130*z* configured to be disposed immediately inside sleeve 544*x*). In this embodiment, hub 130*z* also comprises a flange 568*y* with a circular cross-section that is larger than opening 564*y* such that first end 131 can "snap" into opening 564*y* to (i) maintain its longitudinal position relative to sleeve 544*y*, (ii) create a tortuous path through opening to reduce the likelihood of contaminants traveling through opening 546*y* while IO device 100*z* is coupled to sleeve 544*y*, and (iii) permit IO device 100*z* to rotate relative sleeve 544*y*.

FIGS. 28A-28C depict various views of a twenty-fourth embodiment 300*z* of the present couplers in combination with a powered driver 200*z* and an IO device 100*aa* that is configured to provide access to an interior of a bone (e.g., similar in some respects to IO device 100*c*). In the embodiment shown, driver 200*z* is similar in some respects to driver 200*y*. For example, driver 200*z* comprises: a housing 210*z* having a body portion 213*z* and a shroud portion 396*z*. In this embodiment, body portion 213*z* has a sidewall 400*z* defining distal end 211 of the body portion, and shroud portion 396*z* has a cylindrical sidewall 404*z* extending from distal end 211 of the body portion. In the embodiment shown, shroud portion 396*z* has an open distal end 408*z*. In the embodiment shown, driveshaft 222*z* has a distal end 224*z* extending from body portion 213*z* past distal end 211 and into shroud portion 396*z*). In the embodiment shown, shroud portion 396*z* includes one or more (e.g., two, as shown) projections 536*z* extending (e.g., in opposite directions) from sidewall 404*z* (e.g., and away from driveshaft 222*z*). Driver 200*z* differs from driver 200*y*, for example, in that shroud portion 396*z* (e.g., sidewall 404*z*) comprises one includes two elongated grooves 592*z* in an outer surface of cylindrical sidewall 404*z*, with grooves 592*z* extending in a direction that is substantially perpendicular to the rotational axis of the driveshaft, as shown. In other embodiments, grooves 592*z* can be disposed or orientated at any suitable angle relative to driveshaft 222*z*.

In the embodiment shown, coupler 300*z* comprises a hollow sleeve 544*z* configured to be rotatably coupled to a hub (e.g., a first hub and/or a second hub) of IO device 100*aa*. In this embodiment, sleeve 544*z* includes a proximal portion 548*z* configured to fit over shroud portion 396*z* of housing 210*z* (as shown, for example, in FIG. 28B) to couple the IO device to the driver and resist removal of IO device from the driver. In this embodiment, proximal portion 548*z* of the sleeve comprises two elongated openings 596*z* that are configured to align with grooves 592*z* in shroud portion 396*z* if proximal portion 548*z* is disposed on shroud portion 396*z*. In this embodiment, coupler 300*z* also comprises a resilient U-shaped clip 600*z* having two legs 604*z*, and clip 600*z* is configured to extend over proximal portion 548*z* with legs 604*z* extending through elongated openings 596*z* and into elongated grooves 592*z* to resist removal of the sleeve and IO device from the driver (as shown in FIGS. 28B and 28C).

Figure 29A:
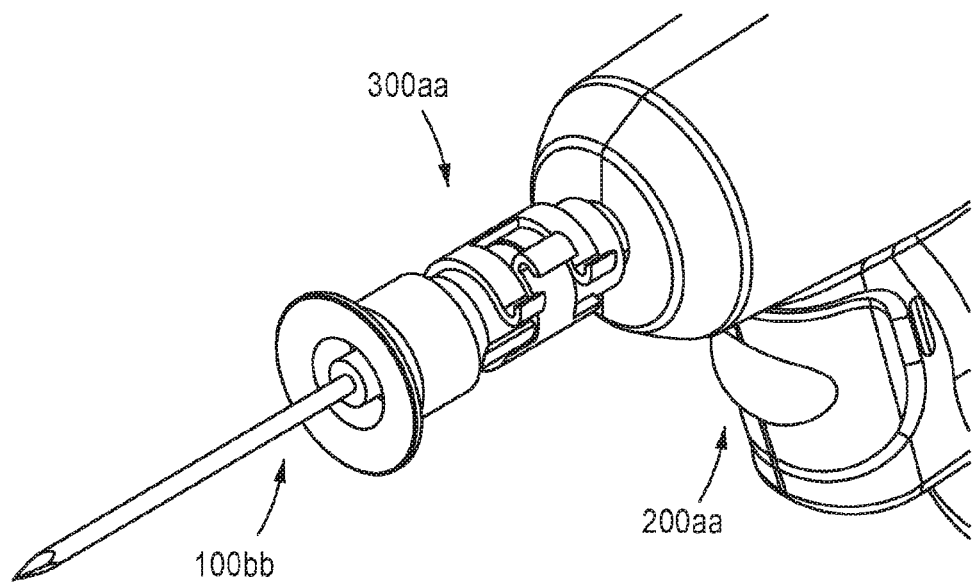
FIGS. 29A-29D depict various views of a twenty-fifth embodiment of the present couplers in combination with a powered driver and an IO device.
Figure 29B:
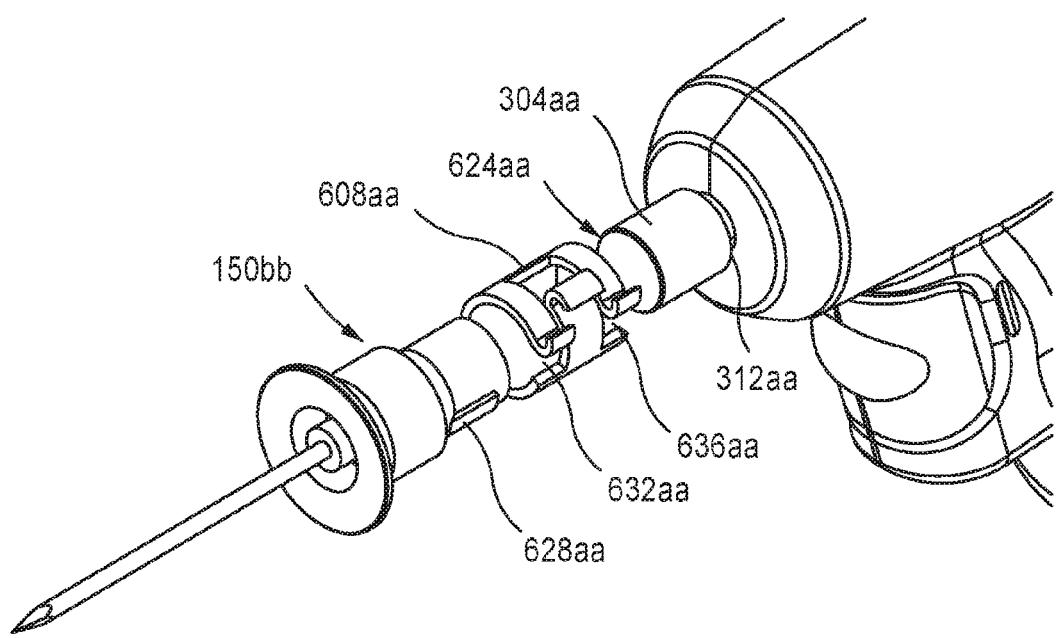
Figure 29C:
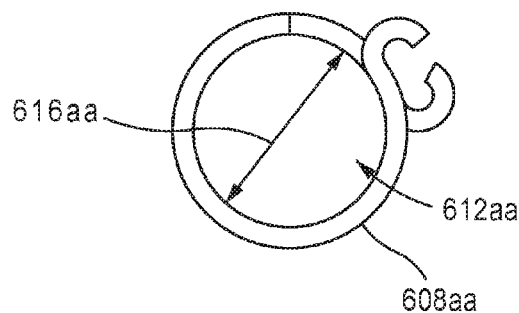
Figure 29D:
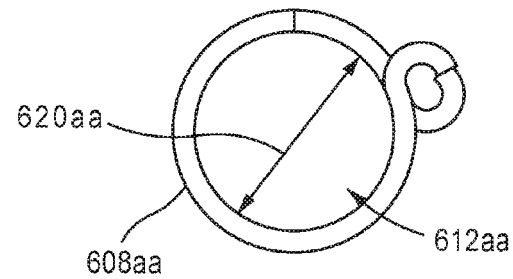

FIGS. 29A-29D depict various views of a twenty-fifth embodiment of the present couplers 300*aa* in combination with a powered driver 200*aa* and an IO device 100*bb* that is configured to provide access to an interior of a bone (e.g., similar in some respects to IO device 100*c*). In the embodiment shown, coupler 300*aa* comprises a drive hub 304*aa* having a first end 308*aa* and a second end 312*aa* configured to be coupled in fixed relation to driveshaft 222*aa* of a driver 200*aa* (e.g., second end 312*aa* is unitary with driveshaft 222*aa* in the embodiment shown). In the embodiment shown, coupler 300*aa* also comprises a resilient clamp 608*aa* having a substantially circular interior 612*aa*, and configured to be movable between (i) a contracted position (FIG. 29C) in which the interior has a first transverse dimension 616*aa*, and (ii) an expanded position (FIG. 29D) in which the interior has a second transverse dimension 620*aa* that is larger than first transverse dimension 616*aa*. In this embodiment, clamp 608*aa* is biased toward the contracted position of FIG. 29C. In the embodiment shown, drive hub 304*aa* has a transverse dimension 624*aa* that is larger than dimension 616*aa* and that is larger than a transverse dimension (e.g., diameter) of driveshaft 222*a*. In this embodiment, first end 308aa of drive hub 304aa is configured to abut IO device 100bb (e.g., a hub 150bb) such that clamp 608aa can be disposed around drive hub 304aa and IO device 100bb (e.g., around hub 150bb) to resist separation of the IO device (and, more specifically, hub 150bb, in this embodiment) from the driver (and, more specifically, drive hub 304aa, in this embodiment), as shown in FIG. 29A.

In the embodiment shown, hub 150bb of IO device 100bb has a cross-section with a circular central portion and a projection 628aa extending from the central portion in a direction away from a rotational axis of the drive hub, as shown. In this embodiment, clamp 608aa includes a slot 632aa between opposing portions of the clamp such that projection 628aa can be aligned with (disposed in) slot 632aa to resist rotation of hub 150bb relative to clamp 608aa. In some embodiments, drive hub 304aa can have a cross-section similar to that of hub 150bb (e.g., having a circular central portion and a projection of the same size(s) as those of hub 150bb), such that the projection of drive hub 304aa can align with (disposed in) a second slot 636aa of clamp 608aa to resist rotation of drive hub 304aa relative to clamp 608aa. In the embodiment shown, drive hub 304a is not configured to receive a portion of IO device 100bb (e.g., adjacent ends of the drive hub and IO device abut each other without overlapping longitudinally, as shown). As shown in FIG. 29A, drive hub 304aa is configured to abut IO device 100bb such that clamp 608aa can be disposed around and in contact with drive hub 304aa and IO device 100bb to resist separation of the IO device from the drive hub.

Figure 30A:
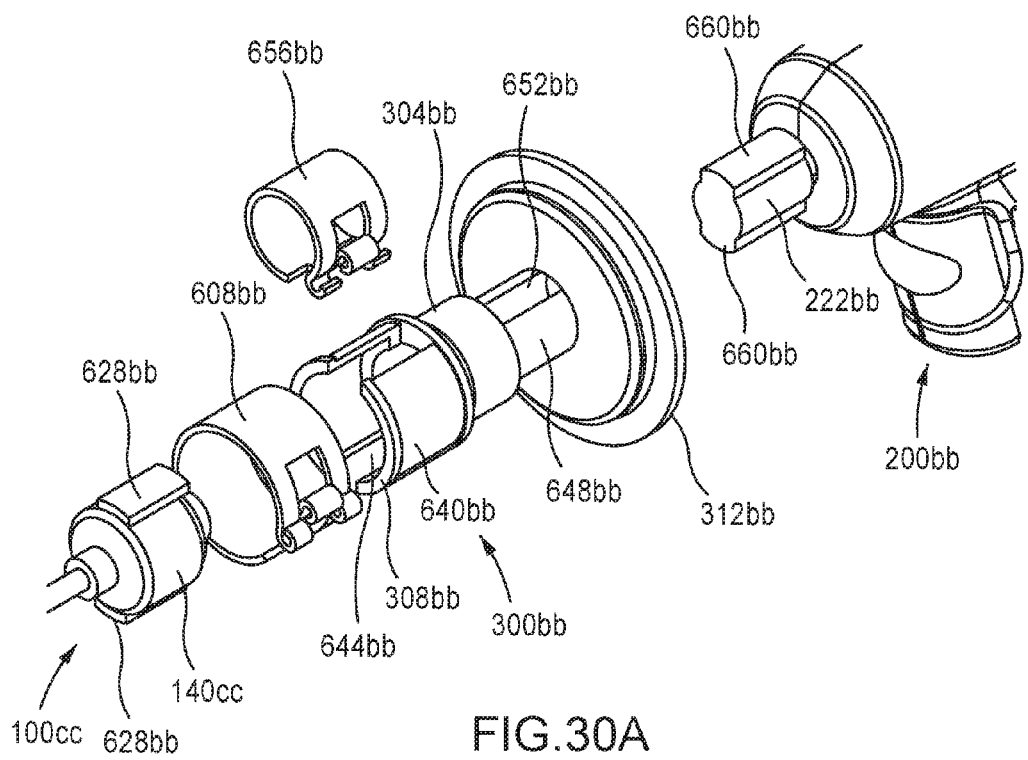
FIGS. 30A-30C depict various views of a twenty-sixth embodiment of the present couplers in combination with a powered driver and an IO device.
Figure 30B:
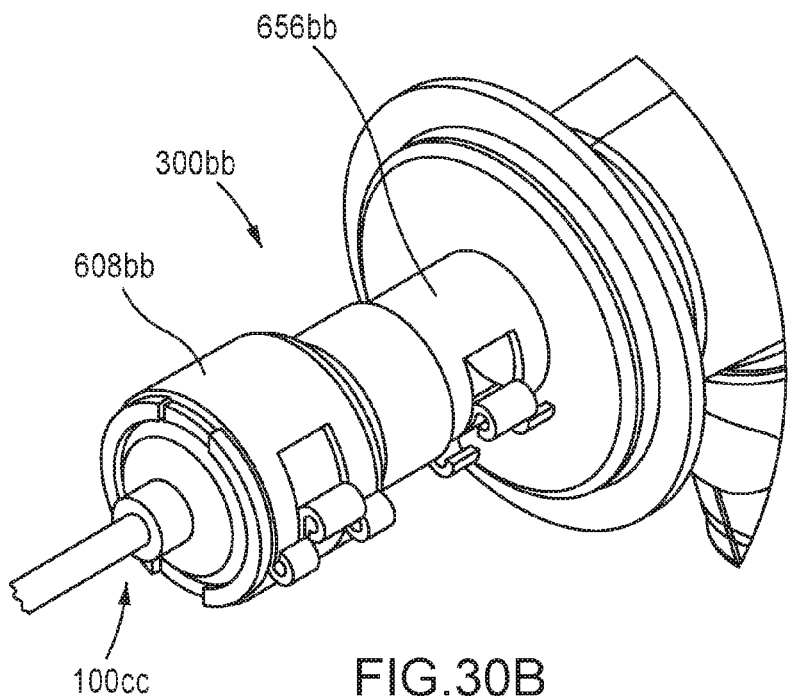
Figure 30C:
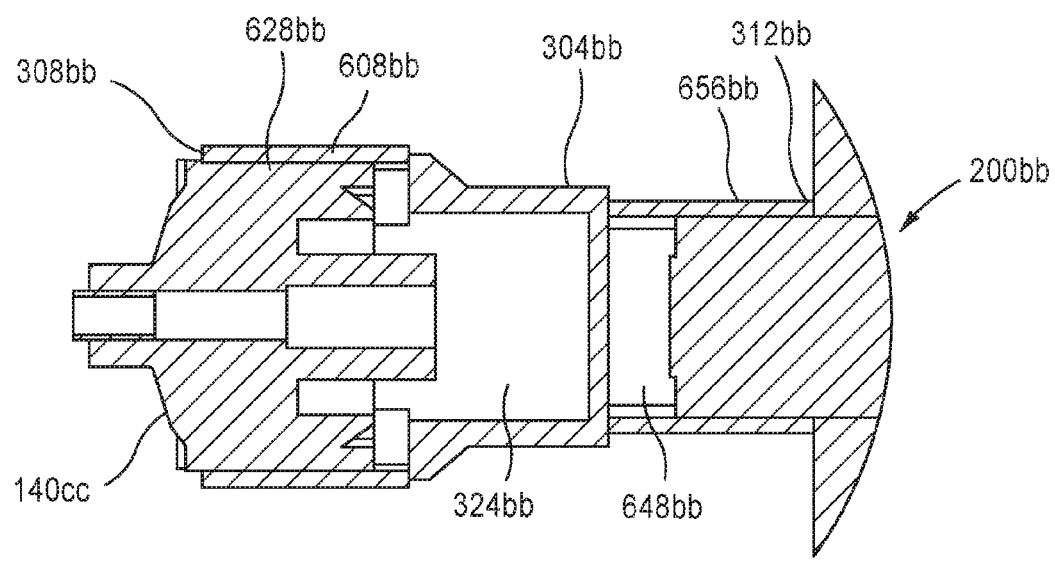

FIGS. 30A-30C depict various views of a twenty-sixth embodiment 300bb of the present couplers in combination with a powered driver 200bb and an IO device 100 cc that is configured for obtaining a sample of bone and/or bone marrow (e.g., similar in some respects to IO devices 100a and/or 100b). In the embodiment shown, coupler 300bb comprises a drive hub 304bb having a first end 308bb and a second end 312bb. In this embodiment, first end 308bb of drive hub 304bb includes a sidewall 640bb defining a recess 340bb configured to receive a hub (e.g., first hub 140 cc) of IO device 100 cc. In this embodiment, sidewall 640bb has at least one (e.g., two, as shown) slot 644bb extending through the sidewall in communication with recess 340bb. Clamp 608bb (which is substantially similar to clamp 608aa described above) is configured to fit over sidewall 640bb and slot 644bb permits the sidewall to flex inwardly to clamp hub 140 cc. In the embodiment shown, hub 140 cc of IO device 100 cc has a cross-section with a circular central portion and projections 628bb extending from the central portion in a direction away from a rotational axis of the drive hub, as shown. In this embodiment, projections 628bb can be aligned with (e.g., disposed in) slots 644bb to resist rotation of hub 140 cc relative to drive hub 304bb. In this embodiment, the transverse dimension of drive hub 304bb is greater than the contracted transverse dimension of clamp 608bb such when clamp 608bb is disposed around first end 308bb of drive hub 304bb, clamp 608bb will contact and apply a compressive force to projections 628bb (as well as to sidewall 640bb) to resist separation of the IO device (and, more specifically, hub 140 cc, in this embodiment) from the driver (and, more specifically, drive hub 304bb, in this embodiment).

In the embodiment shown, second end 312bb of drive hub 304bb includes sidewall 648bb defining a recess 336bb configured to receive driveshaft 222bb of driver 200bb. In this embodiment, sidewall 648bb has at least one (e.g., two, as shown) slot 652bb extending through the sidewall in communication with recess 336bb. Coupler 300bb also comprises a clamp 656bb (which is substantially similar to clamp 608aa described above) that is configured to fit over sidewall 648bb and slot 652bb may permit the sidewall to flex inwardly to clamp hub 140 cc. In the embodiment shown, driveshaft 222bb of driver 200bb has a cross-section with a circular central portion and projections 660bb extending from the central portion in a direction away from a rotational axis of the drive hub, as shown. In this embodiment, projections 660bb can be aligned with (disposed in) slots 652bb to resist rotation of drive hub 304bb relative to driveshaft 222bb. In this embodiment, the transverse dimension of driveshaft 222bb is greater than the contracted transverse dimension of clamp 656bb such that when clamp 656bb is disposed around second end 312bb of drive hub 304bb, clamp 656bb will contact and apply a compressive force to projections 660bb to resist separation of drive hub 304bb from driveshaft 222b. Coupler 300bb also includes a recess 324bb that is sized to receive a second hub (not shown, but similar to second hub 150a of IO device 100a).

Figure 31A:
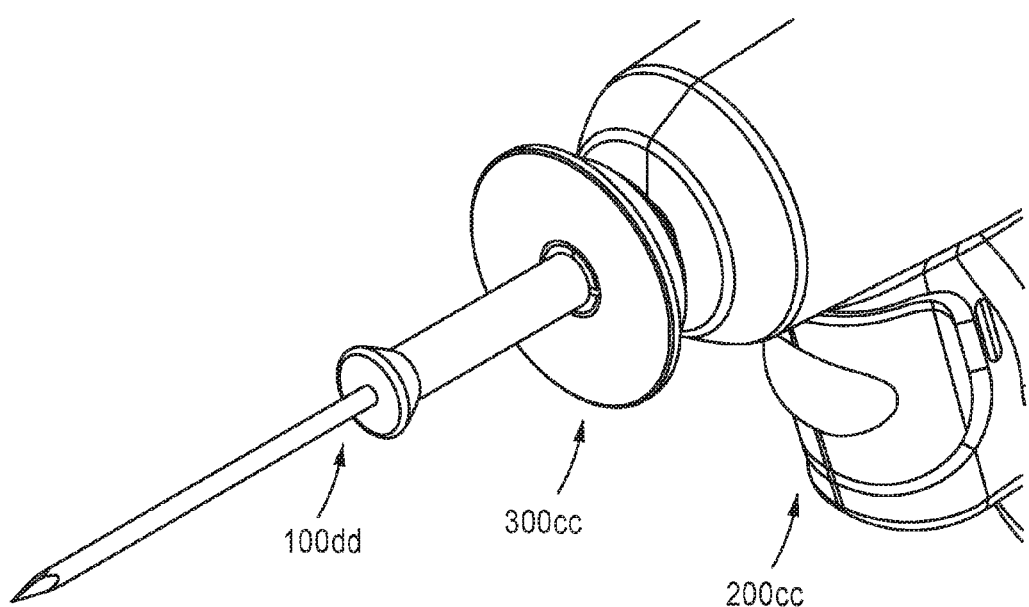
FIGS. 31A-31D depict various views of a twenty-seventh embodiment of the present couplers in combination with a powered driver and an IO device.
Figure 31B:
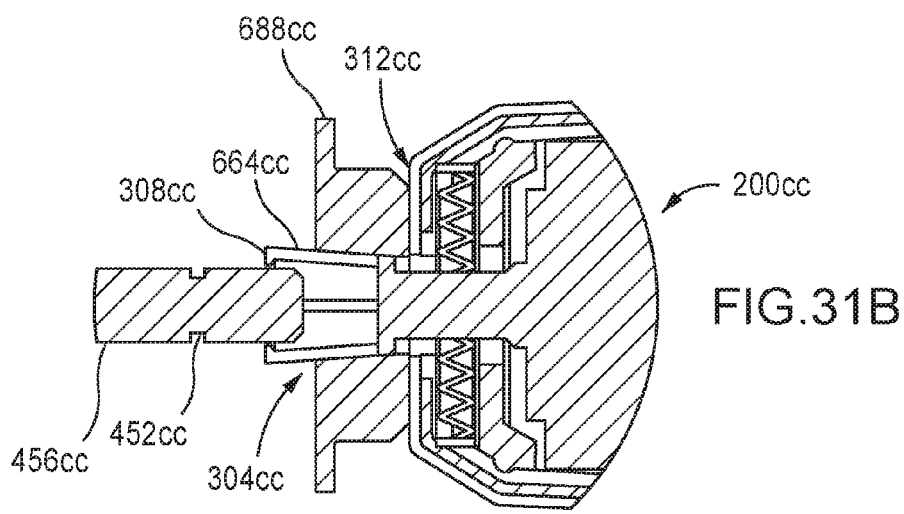
Figure 31C:
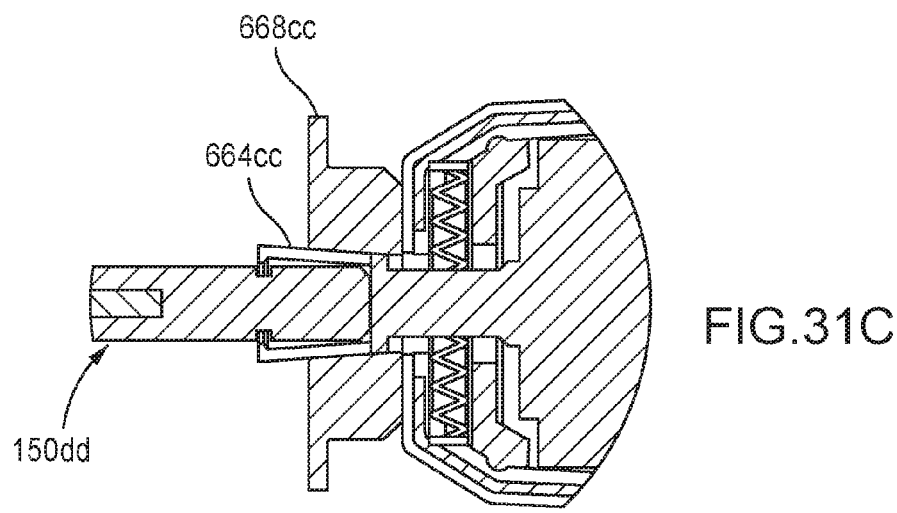
Figure 31D:
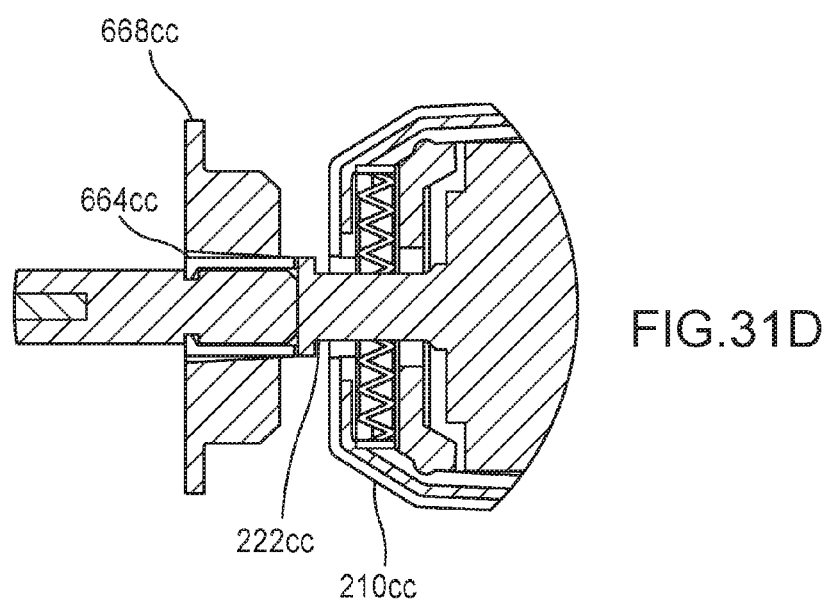

FIGS. 31A-31D depict various views of a twenty-seventh embodiment 300 cc of the present couplers in combination with a powered driver 200cc and an IO device 100dd that is that is configured to provide access to an interior of a bone (e.g., similar in some respects to IO device 100c). In the embodiment shown, coupler 300cc comprises a drive hub 304 cc having a first end 308cc and a second end 312cc configured to be coupled in fixed relation to driveshaft 222cc of driver 200cc (e.g., second end 312cc is unitary with driveshaft 222cc in the embodiment shown). In the embodiment shown, first end 308aa includes a plurality of movable prongs 664cc configured to grasp a hub (e.g., second hub 150dd) of IO device 100dd; and a collar 668cc that is movably disposed around drive hub 304 cc, as shown. In this embodiment, collar 668cc is movable between: (i) a first position (FIGS. 31B and 31C) in which prongs 664cc can move away from the rotational axis of the drive hub to permit IO device 100dd to be inserted into or removed from the prongs, and (ii) a second position (FIG. 31D) in which collar 668cc constrains prongs 664cc such that if hub 150dd is disposed between prongs 664cc, prongs 664cc resist removal of the IO device from the plurality of prongs. In some embodiments, collar 668cc is biased toward the second position (e.g., by a spring (not shown) disposed between collar 668cc and housing 210cc of driver 200cc). In the embodiment shown, hub 150dd of IO device 100dd comprises a projection 456cc with one or more detents 452cc that are configured to receive a portion of prongs 664cc, as shown in FIG. 31D. While not shown in FIGS. 31A-31D, other embodiments can comprise a second plurality of prongs and a second collar at second end 312cc to engage a driveshaft of a driver (e.g., with corresponding detents).

Figure 32A:
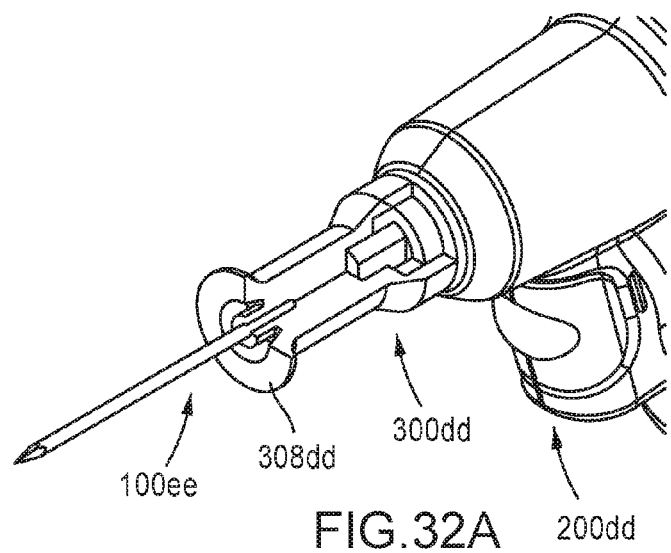
FIGS. 32A-32C depict various views of a twenty-eighth embodiment of the present couplers in combination with a powered driver and an IO device.
Figure 32B:
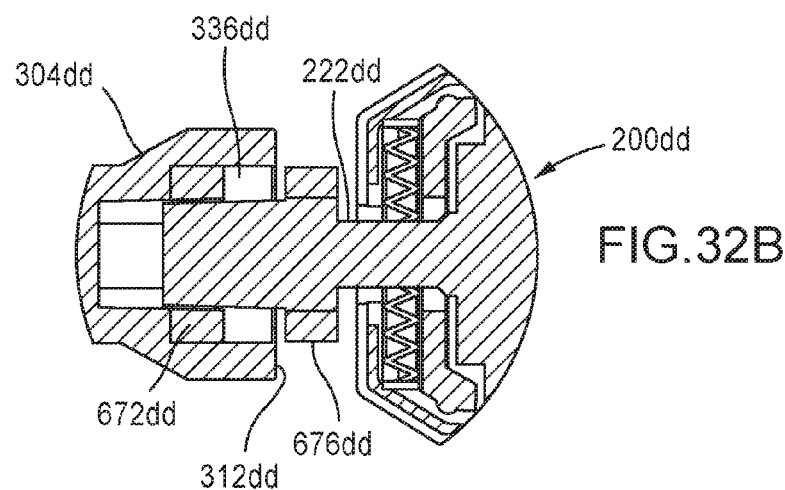
Figure 32C:
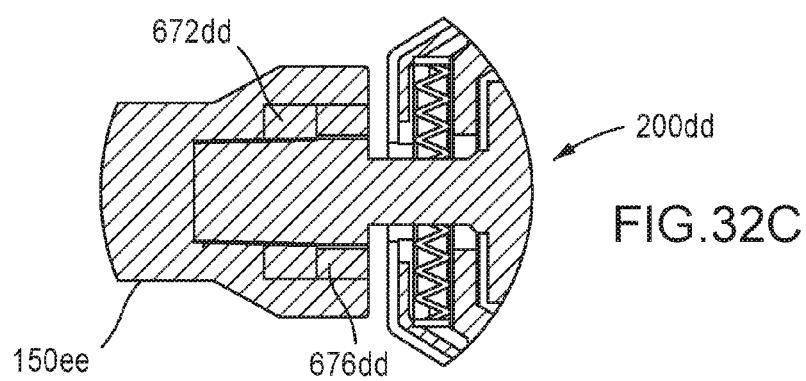

FIGS. 32A-32C depict various views of a twenty-eighth embodiment 300dd of the present couplers in combination with a powered driver 200dd and an IO device 100ee that is configured to provide access to an interior of a bone (e.g., similar in some respects to IO device 100c). In the embodiment shown, coupler 300dd comprises a drive hub 304dd having a first end 308dd and a second end 312dd including a recess 336dd configured to receive driveshaft 222dd of driver 200dd, with recess 336dd having a proximal end at second end 312dd and a distal end closer to first end 308dd. In this embodiment, coupler 300dd also comprises a ring 672dd that comprises at least one of a magnetically-chargeable (e.g., iron) and a magnetically-attractive material (e.g., a permanent magnet). Ring 672dd is disposed around a perimeter of recess 336dd between the proximal and distal ends of the recess, as shown. In this embodiment, driver 200*dd* also comprises a ring 676*dd* that comprises at least one of a magnetically-chargeable (e.g., iron) and a magnetically-attractive material (e.g., a permanent magnet). Ring 676*dd* is disposed around and coupled in fixed relation to driveshaft 222*dd*, as shown. Ring 672*dd* and ring 676*dd* are configured to be magnetically attracted to each other when driveshaft 222*dd* is inserted into recess 336*dd* (FIG. 32C) to resist separation of drive hub 304*dd* from driveshaft 222*dd*. For example, ring 672*dd* and ring 676*dd* can both comprise magnetically-attractive materials, or one can comprise a magnetically-attractive material and the other can comprise a magnetically-chargeable material. In this embodiment, first end 308*dd* of drive hub 304*dd* is configured to be coupled to an intraosseous (IO) device (e.g., to resist rotation of the IO device relative to the drive hub). For example, in the embodiment shown, drive hub 304*dd* is unitary with a portion of the hub assembly of the IO device (e.g., unitary with second hub 150*ee*). In some embodiments, driveshaft 222*dd* and/or recess 336*dd* have non-circular cross-sectional shapes (e.g., to resist rotation of drive hub 304*dd* relative to driveshaft 222*dd*). As shown, recess 336*dd* and ring 672*dd* are configured such that ring 672*dd* defines a step within the recess between the proximal and distal ends of the recess.

Figure 33A:
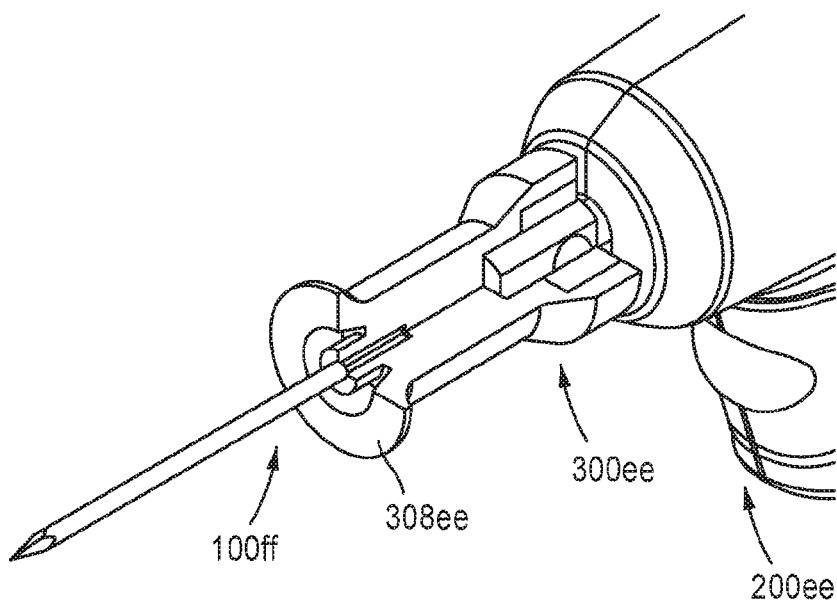
FIGS. 33A-33B depict cutaway perspective and side cross-sectional views, respectively, of a twenty-ninth embodiment of the present couplers in combination with a powered driver and an IO device.
Figure 33B:
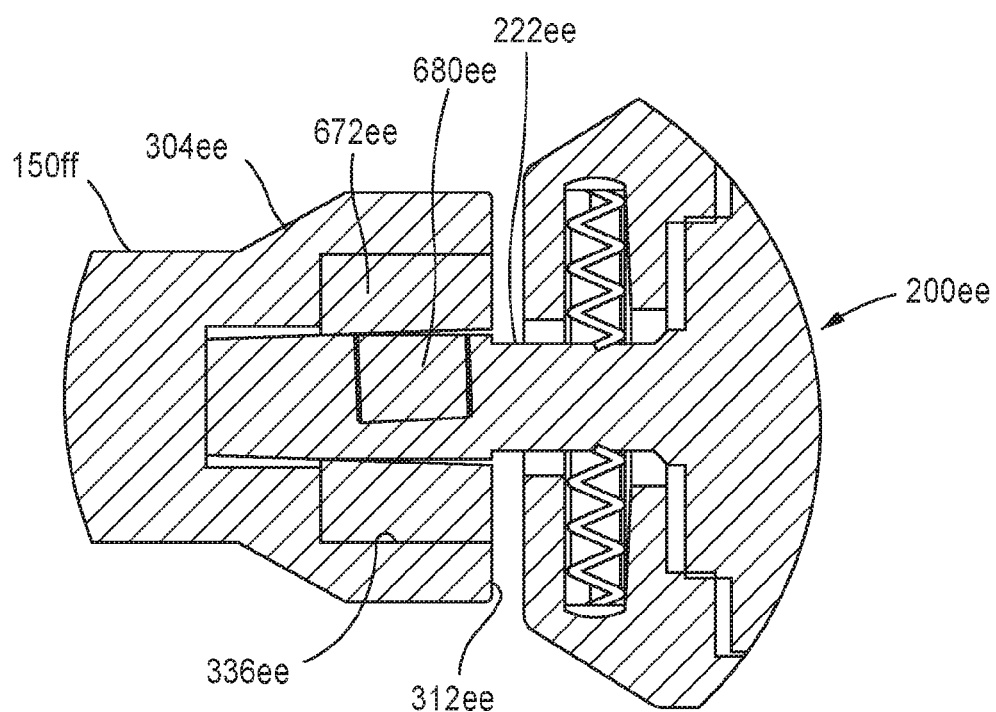

FIGS. 33A-33B depict cutaway perspective and side cross-sectional views, respectively, of a twenty-ninth embodiment 300*ee* of the present couplers in combination with a powered driver 200*ee* and an IO device 100*ff* that is configured to provide access to an interior of a bone (e.g., similar in some respects to IO device 100*c*). In the embodiment shown, coupler 300*ee* comprises a drive hub 304*ee* having a first end 308*ee* and a second end 312*ee* including a recess 336*ee* configured to receive driveshaft 222*ee* of driver 200*ee*, with recess 336*ee* having a proximal end at second end 312*ee* and a distal end closer to first end 308*ee*. In this embodiment, coupler 300*ee* also comprises a ring 672*ee* that comprises at least one of a magnetically-chargeable (e.g., iron) and a magnetically-attractive material (e.g., a permanent magnet). Ring 672*ee* is disposed around a perimeter of recess 336*ee* between the proximal and distal ends of the recess, as shown. In this embodiment, driver 200*ee* also comprises an element 680*ee* that comprises at least one of a magnetically-chargeable (e.g., iron) and a magnetically-attractive material (e.g., a permanent magnet). As shown, element 680*ee* is disposed within the perimeter of driveshaft 222*ee* and spaced apart from the distal end 224*ee* of the driveshaft, as shown. Ring 672*ee* and element 680*ee* are configured to be magnetically attracted to each other when driveshaft 222*ee* is inserted into recess 336*ee* (FIG. 33B) to resist separation of drive hub 304*ee* from driveshaft 222*ee*. For example, ring 672*ee* and element 680*ee* can both comprise magnetically-attractive materials, or one can comprise a magnetically-attractive material and the other can comprise a magnetically-chargeable material. In this embodiment, first end 308*ee* of drive hub 304*ee* is configured to be coupled to an intraosseous (IO) device (e.g., to resist rotation of the IO device relative to the drive hub). For example, in the embodiment shown, drive hub 304*ee* is unitary with a portion of the hub assembly of the IO device (e.g., unitary with second hub 150*ff*). In some embodiments, driveshaft 222*ee* and/or recess 336*ee* have non-circular cross-sectional shapes (e.g., to resist rotation of drive hub 304*ee* relative to driveshaft 222*ee*).

Figure 34A:
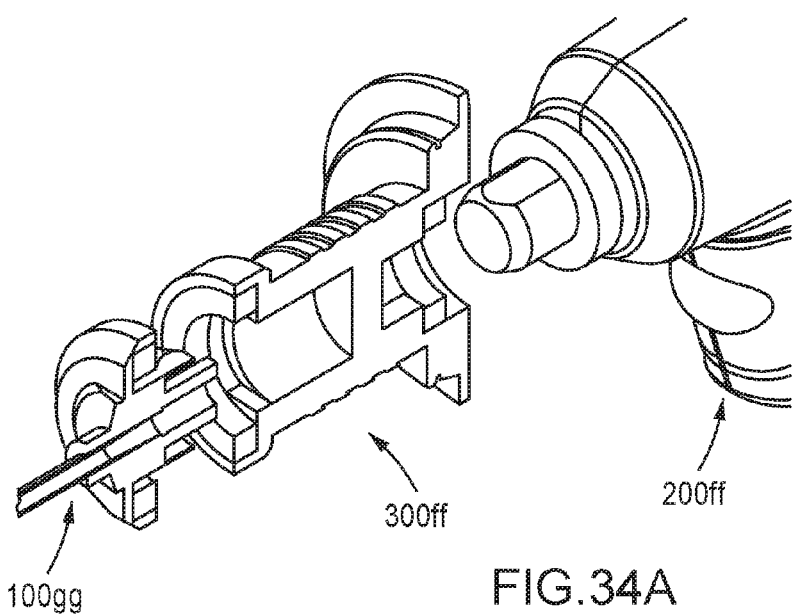
FIGS. 34A-34C depict various views of a thirtieth embodiment of the present couplers in combination with a powered driver and an IO device.
Figure 34B:
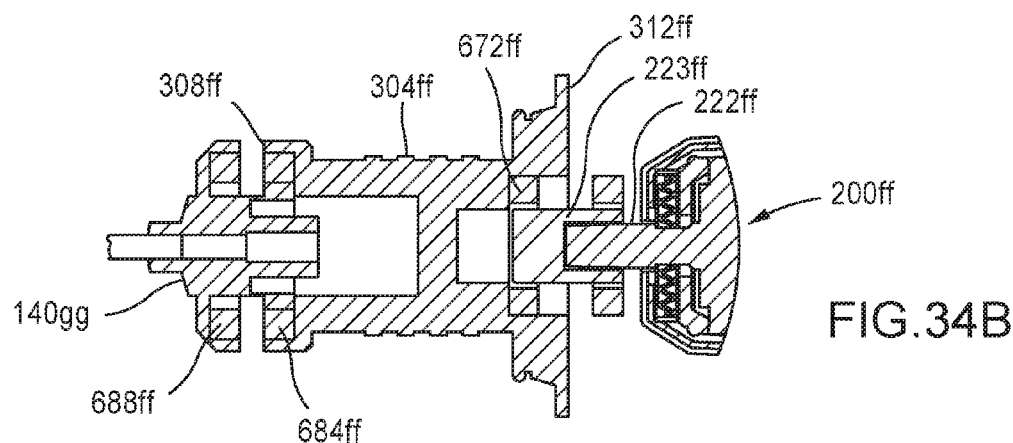
Figure 34C:
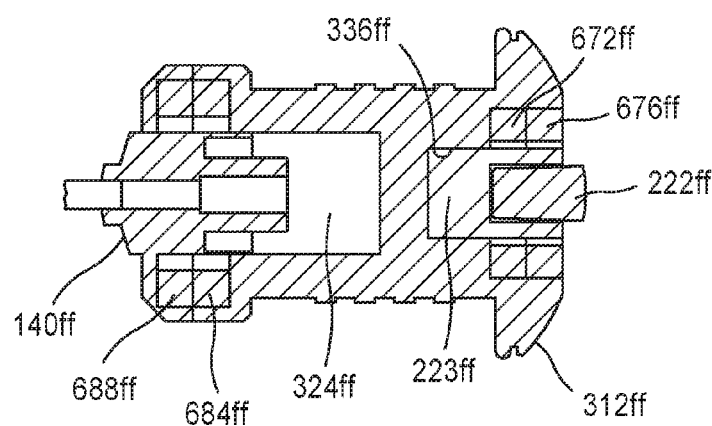

FIGS. 34A-34C depict various views of a thirtieth embodiment 300*ff* of the present couplers in combination with a powered driver 200*ff* and an IO device 100*gg* that is configured for obtaining a sample of bone and/or bone marrow (e.g., similar in some respects to IO devices 100*a* and/or 100*b*). In the embodiment shown, coupler 300*ff* comprises a drive hub 304*ff* having a first end 308*ff* and a second end 312*ff* including a recess 336*ff* configured to receive driveshaft 222*ff* of driver 200*ff*, with recess 336*ff* having a proximal end at second end 312*ff* and a distal end closer to first end 308*ff*. In this embodiment, coupler 300*ff* also comprises a ring 672*ff* that comprises at least one of a magnetically-chargeable (e.g., iron) and a magnetically-attractive material (e.g., a permanent magnet). Ring 672*ff* is disposed around a perimeter of recess 336*ff* between the proximal and distal ends of the recess, as shown. In this embodiment, driver 200*ff* also comprises a ring 676*ff* that comprises at least one of a magnetically-chargeable (e.g., iron) and a magnetically-attractive material (e.g., a permanent magnet). Ring 676*ff* is disposed around and coupled in fixed relation to driveshaft 222*ff*, as shown. Ring 672*ff* and ring 676*ff* are configured to be magnetically attracted to each other when driveshaft 222*ff* is inserted into recess 336*ff* (FIG. 34C) to resist separation of drive hub 304*ff* from driveshaft 222*ff*. For example, ring 672*ff* and ring 676*ff* can both comprise magnetically-attractive materials, or one can comprise a magnetically-attractive material and the other can comprise a magnetically-chargeable material. In some embodiments, driveshaft 222*ff* and/or recess 336*ff* have non-circular cross-sectional shapes (e.g., to resist rotation of drive hub 304*ff* relative to driveshaft 222*ff*). As shown, recess 336*ff* and ring 672*ff* are configured such that ring 672*ff* defines a step within the recess between the proximal and distal ends of the recess. Further, in this embodiment driveshaft 222*ff* comprises an enlarged cap member 223*ff* (on which ring 672*ff* is disposed) that can comprise a resilient material (e.g., a resilient polymer) to further facilitate insertion of driveshaft 222*ff* into recess 336*ff*.

Coupler 300*ff* differs from coupler 300*dd*, for example, in that first end 308*ff* includes a recess 340*ff* configured to receive a hub (e.g., first hub 140*gg*) of IO device 100*gg*, with recess 340*ff* having a distal end at first end 308*ff* and a proximal end closer to second end 312*ff*. In this embodiment, coupler 300*ff* also comprises a ring 684*ff* that comprises at least one of a magnetically-chargeable (e.g., iron) and a magnetically-attractive material (e.g., a permanent magnet). Ring 684*ff* is disposed around a perimeter of recess 340*ff* between the proximal and distal ends of the recess, as shown. In this embodiment, driver 200*ff* also comprises a ring 688*ff* that comprises at least one of a magnetically-chargeable (e.g., iron) and a magnetically-attractive material (e.g., a permanent magnet). Ring 688*ff* is disposed around and coupled in fixed relation to hub 140*gg*, as shown. Ring 684*ff* and ring 680*ff* are configured to be magnetically attracted to each other when hub 140*gg* is inserted into recess 340*ff* (FIG. 34C) to resist separation of hub 140*gg* from drive hub 304*ff*. For example, ring 684*ff* and ring 684*ff* can both comprise magnetically-attractive materials, or one can comprise a magnetically-attractive material and the other can comprise a magnetically-chargeable material. In some embodiments, hub 140*gg* and recess 340*ff* have non-circular cross-sectional shapes (e.g., to resist rotation of hub 140*gg* relative to drive hub 304*ff*). As shown, recess 340*ff* and ring 684*ff* are configured such that ring 684*ff* defines a step within the recess between the proximal and distal ends of the recess. Coupler 300*ff* also includes a recess 324*ff* that is sized to receive a second hub (not shown, but similar to second hub 150*a* of IO device 100*a*).

Figure 35A:
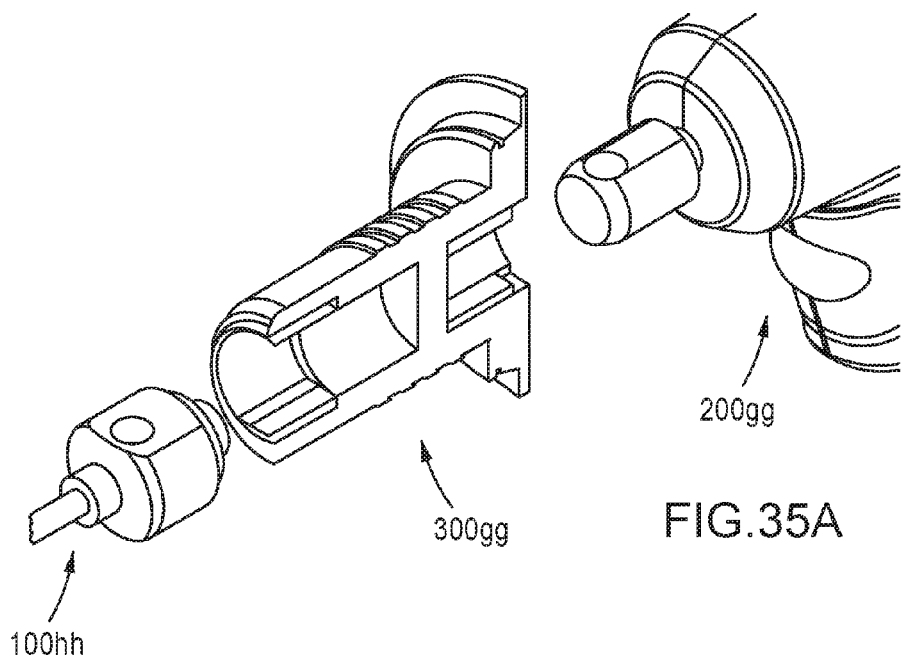
FIGS. 35A-35C depict various views of a thirty-first embodiment of the present couplers in combination with a powered driver and an IO device.
Figure 35B:
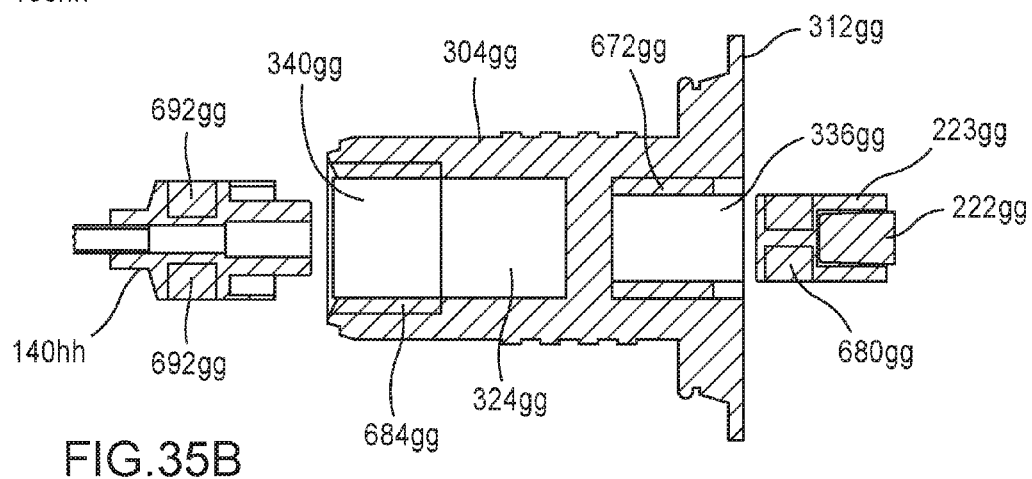
Figure 35C:
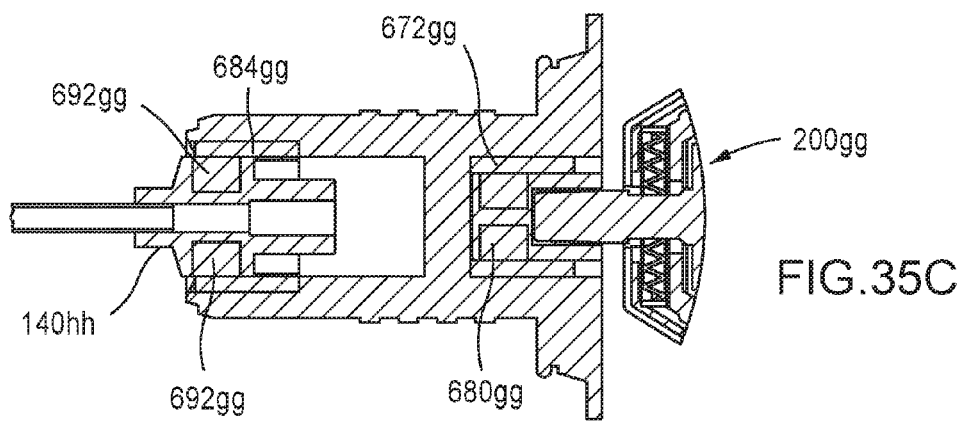

FIGS. 35A-35C depict various views of a thirty-first embodiment 300*gg* of the present couplers in combination with a powered driver 200*gg* and an IO device 100*hh* that is configured for obtaining a sample of bone and/or bone marrow (e.g., similar in some respects to IO devices 100a and/or 100b). In the embodiment shown, coupler 300gg comprises a drive hub 304gg having a first end 308gg and a second end 312gg including a recess 336gg configured to receive driveshaft 222gg of driver 200gg, with recess 336gg having a proximal end at second end 312gg and a distal end closer to first end 308gg. In this embodiment, coupler 300gg also comprises a ring 672gg that comprises at least one of a magnetically-chargeable (e.g., iron) and a magnetically-attractive material (e.g., a permanent magnet). Ring 672gg is disposed around a perimeter of recess 336gg between the proximal and distal ends of the recess, as shown. In this embodiment, driver 200ff also comprises at least one (e.g., two, as shown) element 680gg that comprises at least one of a magnetically-chargeable (e.g., iron) and a magnetically-attractive material (e.g., a permanent magnet). As shown, elements 680gg are disposed within the perimeter of driveshaft 222gg and spaced apart from the distal end 224gg of the driveshaft, as shown. Ring 672gg and elements 680gg are configured to be magnetically attracted to each other when driveshaft 222ff is inserted into recess 336ff (FIG. 35B) to resist separation of drive hub 304gg from driveshaft 222gg. For example, ring 672gg and element 680gg can both comprise magnetically-attractive materials, or one can comprise a magnetically-attractive material and the other can comprise a magnetically-chargeable material. In some embodiments, driveshaft 222gg and/or recess 336gg have non-circular cross-sectional shapes (e.g., to resist rotation of drive hub 304gg relative to driveshaft 222gg). Further, in this embodiment driveshaft 222gg comprises an enlarged cap member 223gg (in which elements 680gg are disposed) that can comprise a resilient material (e.g., a resilient polymer) to further facilitate insertion of driveshaft 222gg into recess 336gg.

Coupler 300gg differs from coupler 300ee, for example, in that first end 308gg includes a recess 340gg configured to receive a hub (e.g., first hub 140hh) of IO device 100hh, with recess 340gg having a distal end at first end 308gg and a proximal end closer to second end 312gg. In this embodiment, coupler 300gg also comprises a ring 684gg that comprises at least one of a magnetically-chargeable (e.g., iron) and a magnetically-attractive material (e.g., a permanent magnet). Ring 684gg is disposed around a perimeter of recess 340gg between the proximal and distal ends of the recess, as shown. In this embodiment, driver 200gg also comprises at least one (e.g., two, as shown) element 692gg that comprises at least one of a magnetically-chargeable (e.g., iron) and a magnetically-attractive material (e.g., a permanent magnet). As shown, elements 692gg are disposed within the perimeter of hub 140hh. Ring 684gg and elements 692gg are configured to be magnetically attracted to each other when driveshaft 222gg is inserted into recess 340gg (FIG. 35B) to resist separation of hub 140hh from drive hub 304gg. For example, ring 684gg and elements 692gg can both comprise magnetically-attractive materials, or one can comprise a magnetically-attractive material and the other can comprise a magnetically-chargeable material. In some embodiments, hub 140hh and/or recess 340gg have non-circular cross-sectional shapes (e.g., to resist rotation of hub 140hh relative to drive hub 304gg). Coupler 300gg also includes a recess 324gg that is sized to receive a second hub (not shown, but similar to second hub 150a of IO device 100a).

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. For example, components may be combined as a unitary structure, and/or connections may be substituted (e.g., threads may be substituted with press-fittings or welds). Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A coupler comprising:
a hollow sleeve having a first end and a second end;
where the first end of the sleeve has a first opening sized to correspond to a portion of a hub of an intraosseous ("IO") device and configured to receive the hub of the IO device;
where the second end of the sleeve has a second opening configured to receive a portion of a driver;
where the sleeve prevents a rotation of a driveshaft of the driver relative to the IO device when the portion of the hub is received in the first opening of the sleeve and the portion of the driver is received in the second opening of the sleeve;
where the hub is configured to rotate relative to the sleeve when the portion of the hub is received in the first opening of the sleeve and the portion of the driver is received in the second opening of the sleeve;
where the portion of the driver comprises a driveshaft and a shroud portion spaced from the driveshaft;
where a projection is disposed on the shroud portion, the projection extending radially outward from the shroud portion;
where the second end of the sleeve comprises a wall defining a L-shaped slot; and
where the projection is configured to be disposed in the L-shaped slot when the portion of the driver is received in the second opening of the sleeve.

2. The coupler of claim 1, where the first opening and the second opening have circular cross-sections; and
where a diameter of circular cross-section of the first opening is smaller than a diameter of the circular cross-section of the second opening.

3. The coupler of claim 2, where the hub of the IO device comprises a flange having a circular cross-section with a diameter larger than the diameter of the circular cross-section of the first opening.

4. The coupler of claim 3, where the flange of the hub of the IO device is configured to maintain a longitudinal position of the hub relative to the sleeve when the portion of the hub is received in the first opening of the sleeve.

5. The coupler of claim 3, where the flange of the hub of the IO device is configured to prevent contaminants from entering the first opening of the sleeve when the portion of the hub is received in the first opening of the sleeve.

6. The coupler of claim 1, where the shroud portion is a cylindrical wall.

7. The coupler of claim 6, where the hub of the IO device comprises a recess, the recess configured to receive a portion of the driveshaft of the driver.

8. The coupler of claim 6, where the hub of the IO device extends at least a longitudinal length of the sleeve.

9. The coupler of claim 1, where the portion of the hub of the IO device has a circular cross-section that is sized to correspond to a circular cross-section of the first opening.

10. The coupler of claim 9, where a different portion of the hub of the IO device disposed adjacent to the portion of the hub received in the first opening of the sleeve has a circular cross-section that is larger than the circular cross-section of the portion of the hub received in the first opening of the sleeve.

11. The coupler of claim 10, where the different portion of the hub of the IO device is disposed within the sleeve.

12. The coupler of claim 1, where the driveshaft of the driver extends a greater length than the shroud portion of the driver in a direction along an axis of rotation of the driveshaft.

\* \* \* \* \*